US010052377B2

(12) United States Patent
Gowans

(10) Patent No.: US 10,052,377 B2
(45) Date of Patent: Aug. 21, 2018

(54) CELLULAR VACCINE AND METHOD OF INDUCING AN IMMUNE RESPONSE IN A SUBJECT

(71) Applicant: ADELAIDE RESEARCH & INNOVATION PTY LTD., Adelaide, South Australia (AU)

(72) Inventor: Eric James Gowans, Malvern (AU)

(73) Assignee: ADELAIDE RESEARCH & INNOVATION PTY LTD, Adelaide (AU)

( * ) Notice: Subject to any disclaimer, the term of this patent is extended or adjusted under 35 U.S.C. 154(b) by 0 days.

(21) Appl. No.: 15/397,214

(22) Filed: Jan. 3, 2017

(65) Prior Publication Data
US 2017/0106081 A1    Apr. 20, 2017

Related U.S. Application Data

(62) Division of application No. 14/401,182, filed as application No. PCT/AU2013/000509 on May 16, 2013, now Pat. No. 9,585,952.

(30) Foreign Application Priority Data

May 16, 2012    (AU) .............................. 2012902010

(51) Int. Cl.
| A61K 35/12 | (2015.01) |
| A61K 39/29 | (2006.01) |
| A61K 31/711 | (2006.01) |
| A61K 39/12 | (2006.01) |
| A61K 39/21 | (2006.01) |
| C12N 7/00 | (2006.01) |
| A61K 35/15 | (2015.01) |
| A61K 39/00 | (2006.01) |

(52) U.S. Cl.
CPC ............ *A61K 39/29* (2013.01); *A61K 31/711* (2013.01); *A61K 35/12* (2013.01); *A61K 35/15* (2013.01); *A61K 39/12* (2013.01); *A61K 39/21* (2013.01); *C12N 7/00* (2013.01); *A61K 2039/515* (2013.01); *A61K 2039/5154* (2013.01); *A61K 2039/5156* (2013.01); *A61K 2039/53* (2013.01); *A61K 2039/605* (2013.01); *A61K 2039/6037* (2013.01); *A61K 2039/6068* (2013.01); *C07K 2319/00* (2013.01); *C07K 2319/40* (2013.01); *C07K 2319/50* (2013.01); *C07K 2319/55* (2013.01); *C12N 2740/16234* (2013.01); *C12N 2770/00034* (2013.01); *C12N 2770/24234* (2013.01)

(58) Field of Classification Search
CPC ............ C12N 7/00; C12N 2770/10034; C12N 2770/10031; C12N 2750/14321; C12N 2750/14322; C12N 2770/23034; C12N 2740/15022; C12N 2740/16222; A61K 39/12; A61K 2039/552; A61K 2039/53; A61K 39/23; A61K 2039/5252; A61K 39/0208; A61K 2039/57; A61K 2300/00; A61K 2039/515; A61K 2039/5154; C07K 16/10; C07K 2319/00; G01N 2333/015
See application file for complete search history.

(56) References Cited

U.S. PATENT DOCUMENTS

| 2005/0003484 A1 | 1/2005 | Hirano et al. |
| 2005/0003533 A1 | 1/2005 | Kalinski et al. |
| 2005/0095230 A1 | 5/2005 | Yoo et al. |
| 2007/0275915 A1 | 11/2007 | Hallenbeck et al. |
| 2009/0142768 A1 | 6/2009 | Podack et al. |

FOREIGN PATENT DOCUMENTS

| CN | 1752211 A | 3/2006 |
| WO | 2002/036172 | 5/2002 |
| WO | 2003/106616 | 12/2003 |
| WO | 2004/084838 | 10/2004 |
| WO | 2004/092386 | 10/2004 |
| WO | 2005/028634 | 3/2005 |
| WO | 2006/044923 | 4/2006 |
| WO | 2006/073970 | 7/2006 |

OTHER PUBLICATIONS

Alencar et al. Infection and Immunity. Oct. 2009, vol. 77 No. 10, pp. 4383-4395.*
Caetano et al. J. Virol. Aug. 2008, vol. 82 No. 15 7567-7577.*
International Search Report and Written Opinion dated Jul. 26, 2013 from International Application No. PCT/AU2013/000509, pp. 1-17.
Pena, J. et al., "Effects on Inmate Immunity of a Therapeutic Dendritic Cell-Based Vaccine for HIV-1 Infection", Viral Immunology, Feb. 2012, vol. 25, No. 1, pp. 37-44.
Routy, J-P. et al., "Immunologic activity and safety of autologous HIV RNA-electroporated dendritic cells in HIV-1 infected patients receiving antiretroviral therapy", Clin. Immunol., Feb. 2010, vol. 134, No. 2, pp. 140-147.
Yu, H. et al., "Strategies for loading dendritic cells with hepatitis C NS5a antigen and inducing protective immunity", Journal of Viral Hepatitis, Jun. 2008, vol. 15, No. 6, pp. 459-470.
Racanelli, V. et al., "Dendritic Cells Transfected with Cytopathic Self-Replicating RNA Induce Crosspriming of CD8+ T Cells and Antiviral Immunity", Immunity, Jan. 2004, vol. 20, No. 1, pp. 47-58.
Sloan, A. E. et al., "Human autologous dendritic cell-glioma fusions: feasibility and capacity to stimulate T cells with proliferative and cytolytic activity", Journal of Neuro-Oncology, Aug.-Sep. 2003, vol. 64, No. 1-2, pp. 177-183.
Wang, H. et al., "Emerging applications of lentiviral vectors in dendritic cell-based immunotherapy", Immunotherapy, Sep. 2010, vol. 2, No. 5, pp. 685-695.

(Continued)

*Primary Examiner* — Bao Q Li
(74) *Attorney, Agent, or Firm* — MH2 Technology Law Group, LLP

(57) ABSTRACT

The present invention relates to methods of inducing or enhancing an immune response against an immunogen in a subject. The invention further includes isolated nucleic acid vaccines, cellular vaccines, fusion proteins, expression vectors, vaccines, and immunogenic compositions for use therein.

11 Claims, 36 Drawing Sheets

(56) References Cited

OTHER PUBLICATIONS

Simon, G.G. et al., "Dendritic Cell Mediated Delivery of Plasmid DNA Encoding LAMP/HIV-1 Gag Fusion Immunogen Enhances T Cell Epitope Responses in HLA DR4 Transgenic Mice", PLOS One, Jan. 2010, vol. 5, No. 1, p. e8574.

Li et al., "Targeting and Amplification of Immune Killing of Tumor Cells by pro-Smac", Int. J. Cancer, 2004, vol. 109, pp. 85-94.

Black et al., "A Single Amino Acid Substitution Abolishes Feedback Inhibition of Vaccinia Virus Thymidine Kinase", The Journal of Biological Chemistry, May 15, 1992, vol. 267, No. 14, pp. 9743-9748.

Elmetwali et al., "CD40 Ligand-Induced Carcinoma Cell Death: A Balance between Activation of TNFR-Associated Factor (TRAF) 3-Dependent Death Signals and Suppression of TRAF6-Dependent Survival Signals", The Journal of Immunology, 2010, vol. 184, pp. 1111-1120.

Rossi et al., "High-Efficiency Lentiviral Vector-Mediated Gene Transfer into Murine Macrophages and Activated Splenic B Lymphocytes", Human Gene Therapy, Mar. 1, 2003, vol. 14, pp. 385-391.

* cited by examiner

| Frequency of apoptotic and necrotic cells within the dead cell population |||| 
|---|---|---|---|
| DNA vaccine | Apoptotic (%) | Primary necrotic (%) | Secondary necrotic (%) |
| CMV-LUC | 41.1 | 3.12 | 42 |
| CMV-LUC-SV40-PRF | 27.7 | 16.1 | 40.1 |
| CMV-LUC-SV40-DTa | 38.9 | 6.44 | 36.8 |
| CMV-LUC-2A-PRF | 22.3 | 22.4 | 29.7 |

Figure 2

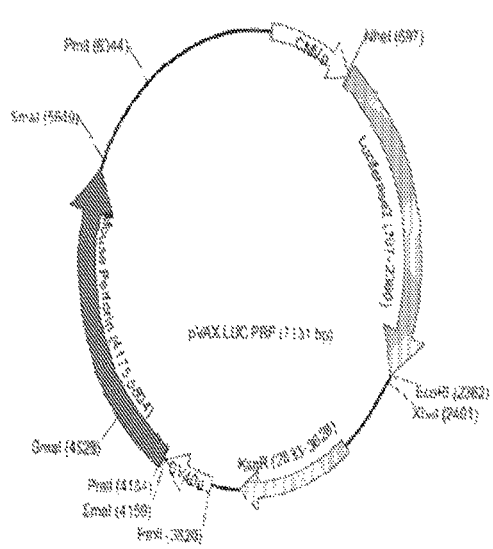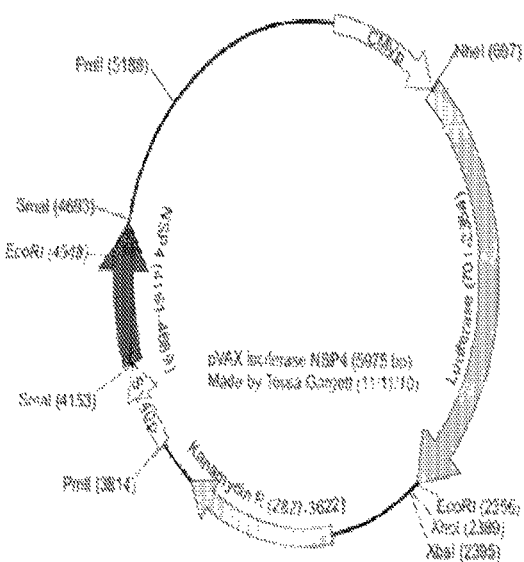
Figure 10                              Figure 9

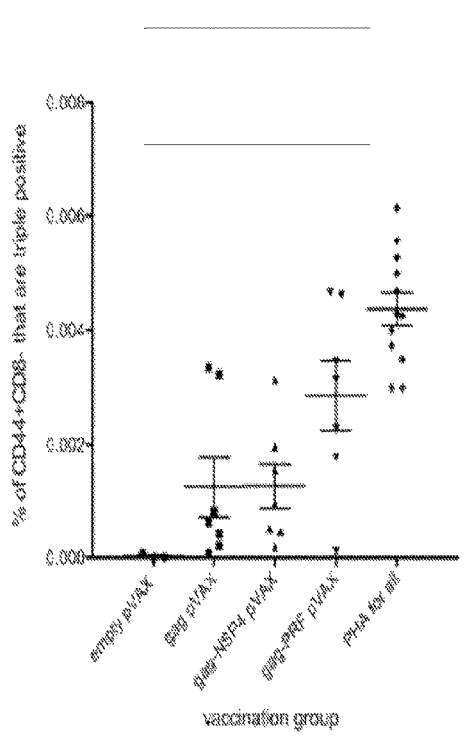 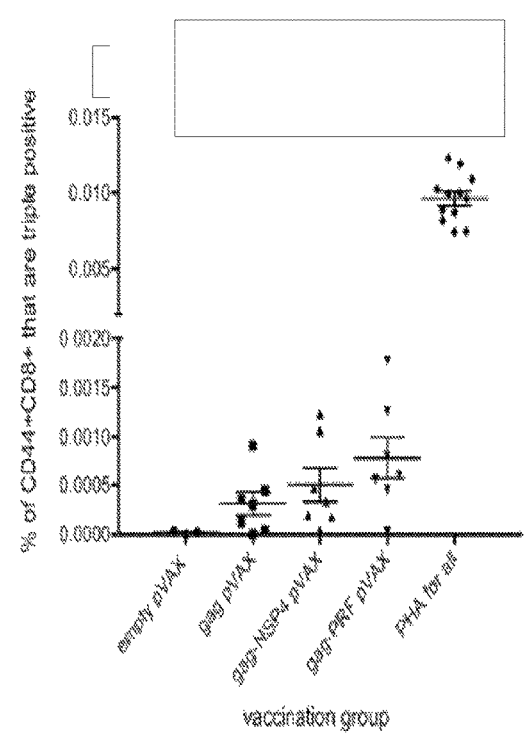
Figure 20
Figure 19

Overview of blood sampling and dosage schedule for HCV immunotherapy trial - Project 30/10

| | | Baseline | | | | | | | | Final dose + 3 days | Final dose + 1 weeks | Final dose + 2 weeks | Final dose + 3 weeks | Final dose + 4 weeks | Final dose + 5 weeks | Final dose + 6 weeks | Final dose + 12 weeks |
|---|---|---|---|---|---|---|---|---|---|---|---|---|---|---|---|---|---|
| | | Week -4 | Week -1 | Week 1 | Week 2 | Week 3 | Week 4 | | | | | | | | | | |
| Patients 1,4,7,10 | | Wk-4 | Wk-1 | Wk 1 | Wk 2 | | | | | Wk 2.5 | Wk 3 | Wk 4 | Wk 5 | Wk 6 | Wk 7 | Wk 8 | Wk 14 |
| Patients 2,5,8,11 | | Wk-4 | Wk-1 | Wk 1 | Wk 2 | Wk 3 | | | | Wk 3.5 | Wk 4 | Wk 5 | Wk 6 | Wk 7 | Wk 8 | Wk 9 | Wk 15 |
| Patients 3,6,9,12 | | Wk-4 | Wk-1 | Wk 1 | Wk 2 | Wk 3 | Wk 4 | | | Wk 4.5 | Wk 5 | Wk 6 | Wk 7 | Wk 8 | Wk 9 | Wk 10 | Wk 16 |
| | | IFN start | PBMC for Mo-DC | Finish IFN Start therapy | | | | | | | | | | | | | |
| Samples | Genotype HLA | | | | | | | | | Haem | Haem | Haem | Haem | Haem | Haem | Haem | Haem |
| | ALT | | | | | | | | | ALT | ALT | ALT | ALT | ALT | ALT | ALT | ALT |
| | IL28B | | | IFN VL | | | | | | Auto | Auto | Auto | Auto | Auto | Auto | Auto | Auto |
| | pre VL | | | | | | | | | | | VL +2Wk | | | | VL +6Wk | VL +12Wk |
| | pre CMI | | | | | | | | | | | CMI +2Wk | | | | CMI +6Wk | CMI |
| Patient | | | | | Dose1 | Dose2 | Dose3 | | | | | | | | | | |
| 1 | | 80mL | 20mL | 10mL | 1 x 10e4 | - | - | | | 10mL | 10mL | 80mL | 10mL | 10mL | 10mL | 80mL | 80mL |
| 2 | | 80mL | 20mL | 10mL | 1 x 10e4 | 1 x 10e4 | - | | | 10mL | 10mL | 80mL | 10mL | 10mL | 10mL | 80mL | 80mL |
| 3 | | 80mL | 20mL | 10mL | 1 x 10e4 | 1 x 10e4 | 1 x 10e4 | | | 10mL | 10mL | 80mL | 10mL | 10mL | 10mL | 80mL | 80mL |
| 4 | | 80mL | 20mL | 10mL | 1 x 10e5 | - | - | | | 10mL | 10mL | 80mL | 10mL | 10mL | 10mL | 80mL | 80mL |
| 5 | | 80mL | 20mL | 10mL | 1 x 10e5 | 1 x 10e5 | - | | | 10mL | 10mL | 80mL | 10mL | 10mL | 10mL | 80mL | 80mL |
| 6 | | 80mL | 20mL | 10mL | 1 x 10e5 | 1 x 10e5 | 1 x 10e5 | | | 10mL | 10mL | 80mL | 10mL | 10mL | 10mL | 80mL | 80mL |
| 7 | | 80mL | 30mL | 10mL | 1 x 10e6 | - | - | | | 10mL | 10mL | 80mL | 10mL | 10mL | 10mL | 80mL | 80mL |
| 8 | | 80mL | 50mL | 10mL | 1 x 10e6 | 1 x 10e6 | - | | | 10mL | 10mL | 80mL | 10mL | 10mL | 10mL | 80mL | 80mL |
| 9 | | 80mL | 35mL | 10mL | 1 x 10e6 | 1 x 10e6 | 1 x 10e6 | | | 10mL | 10mL | 80mL | 10mL | 10mL | 10mL | 80mL | 80mL |
| 10 | | 80mL | 110mL | 10mL | 1 x 10e7 | - | - | | | 10mL | 10mL | 80mL | 10mL | 10mL | 10mL | 80mL | 80mL |
| 11 | 120mL* | 80mL | 110mL | 10mL | 1 x 10e7 | 1 x 10e7 | - | | | 10mL | 10mL | 80mL | 10mL | 10mL | 10mL | 80mL | 80mL |
| 12 | 120mL* | 80mL | 110mL | 10mL | 1 x 10e7 | 1 x 10e7 | 1 x 10e7 | | | 10mL | 10mL | 80mL | 10mL | 10mL | 10mL | 80mL | 80mL |
| | | | | | | 110mL** | | | | | | | | | | | |

Note. * 120mL blood sample necessary to provide Baseline analysis and (cryopreserved) Mo-DC for Dose 2

Viral Load data

| | | | 4Wk IFN | | | Inject #1 | Inject #2 | Inject #3 | | | Weeks after first injection | | | | | | | | | |
|---|---|---|---|---|---|---|---|---|---|---|---|---|---|---|---|---|---|---|---|---|
| Week | Baseline value | | -4 | -3 | -2 | -1 | 0 | 1 | 2 | 3 | 4 | 5 | 6 | 7 | 8 | 9 | 10 | 11 | 12 | 13 | 14 |
| 1 dose LANR0201 | 985,144 | 1 | 100% | | | | 19% | 39% | | | | 140% | | | 85% | | | | 97% | | |
| 2 doses GIUM0202 | 2,212,848 | 2 | 100% | | | | 57% | 77% | | | | | | 125% | | | | | | 75% | |
| 3 doses BURM0203 | 258,343 | 3 | 100% | | | | 19% | | | | | | | | | 148% | | | | | | 64% |
| 1 dose JAMJ0204 | 6,460,191 | 4 | 100% | | | | 0.03% | | | | | | | 16% | | | | | | 77% | | |
| 2 doses CABD0205 | 1,478,340 | 5 | 100% | | | | 23% | | | 61% | | | | | 97% | | | | | | 137% | |
| 3 doses MEEJ0206 | 1,131,121 | 6 | 100% | | | | 0.8% | | | | 14% | | | | | 88% | | | | | | 57% |
| 1 dose JOVN0207 | 1,556,715 | 7 | 100% | | | | 18% | 68% | | | | | 93% | | | | | | | | | |
| 2 doses FIDS0208 | 169,700 | 8 | 100% | | | | 53% | | 211% | | | | | 145% | | | | | | | | |
| 3 doses HANP0209 | 701,519 | 9 | 100% | | | | 9% | 29% | | | | | | | | 32% | | | | | | |
| 1 dose HARF0210 | 2,407,691 | 10 | 100% | | | | 1% | 1% | | | | | 94% | | | | | | | | | |
| 2 doses HARN0211 | 1,791,776 | 11 | 100% | | | | 146% | 123% | | | | | | | | | | | | | | |
| 3 doses SYRR0212 | 886,417 | 12 | 100% | | | | 22% | | | | | | | | | | | | | | | |

Figure 46

HCV Immunotherapy Trial
Viral Load data

| | | | | IFN start | Finish IFN | | |
|---|---|---|---|---|---|---|---|
| | Week | | Baseline value | baseline | Inj #1 | 6wk after inj | 12 wk after inj |
| | | Patient | | -4 | 0 | 6 | 12 |
| 1 dose | LANR0201 | 1 | 985,144 | 100% | 19% | 85% | 97% |
| 2 doses | GIUM0202 | 2 | 2,212,848 | 100% | 57% | 125% | 75% |
| 3 doses | BURM0203 | 3 | 258,343 | 100% | 19% | 148% | 64% |
| 1 dose | JAMJ0204 | 4 | 6,460,191 | 100% | 0.03% | 16% | 77% |
| 2 doses | CABD0205 | 5 | 1,478,340 | 100% | 23% | 97% | 137% |
| 3 doses | MEEJ0206 | 6 | 1,131,121 | 100% | 0.8% | 88% | 57% |
| 1 dose | JOVN0207 | 7 | 1,556,715 | 100% | 18% | 93% | |
| 2 doses | FIDS0208 | 8 | 169,700 | 100% | 53% | 145% | |
| 3 doses | HANP0209 | 9 | 701,519 | 100% | 9% | 32% | |
| 1 dose | HARF0210 | 10 | 2,407,691 | 100% | 1% | 94% | |
| 2 doses | HARN0211 | 11 | 1,791,776 | 100% | 146% | | |
| 3 doses | SYRR0212 | 12 | 886,417 | 100% | 22% | | |

SEQUENCE LISTING

```
<160> NUMBER OF SEQ ID NOS: 14

<210> SEQ ID NO 1
<211> LENGTH: 6607
<212> TYPE: DNA
<213> ORGANISM: Artificial Sequence
<220> FEATURE:
<223> OTHER INFORMATION: Recombinant

<400> SEQUENCE: 1
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgccaccatg aagatgcca     720 aaacattaa gagggccca gcgccattct acccactcga agacgggacc gcggcgagc     780 agctgcacaa agccatgaag cgctacgccc tggtgcccgg caccatcgcc tttaccgacg     840
cacatatcga ggtggacatt acctacgccg agtacttcga gatgagcgtt cggctggcag     900
aagctatgaa gcgctatggg ctgaatacaa accatcggat cgtggtgtgc agcgagaata     960
gcttgcagtt cttcatgccc gtgttgggtg ccctgttcat cggtgtggct gtggcccag    1020 ctaacgacat ctacaacgag cgcgagctgc tgaacagcat gggcatcagc cagcccaccg    1080
tcgtattcgt gagcaagaaa gggctgcaaa agatcctcaa cgtgcaaaag aagctaccga    1140
tcatacaaaa gatcatcatc atggatagca agaccgacta ccagggcttc caaagcatgt    1200
acaccttcgt gacttcccat ttgccacccg gcttcaacga gtacgacttc gtgcccgaga    1260
gcttcgaccg ggacaaaacc atcgccctga tcatgaacag tagtggcagt accggattgc    1320
ccaagggcgt agccctaccg caccgcaccg cttgtgtccg attcagtcat gcccgcgacc    1380
ccatcttcgg caaccagatc atccccgaca ccgctatcct cagcgtggtg ccatttcacc    1440
acggcttcgg catgttcacc acgctgggct acttgatctg cggctttcgg gtcgtgctca    1500
```

-continued

```
tgtaccgctt cgaggaggag ctattcttgc gcagcttgca agactataag attcaatctg    1560
ccctgctggt gcccacacta tttagcttct tcgctaagag cactctcatc gacaagtacg    1620
acctaagcaa cttgcacgag atcgccagcg gcggggcgcc gctcagcaag gaggtaggtg    1680
aggccgtggc caaacgcttc cacctaccag gcatccgcca gggctacggc ctgacagaaa    1740
caaccagcgc cattctgatc accccgaag gggacgacaa gcctggcgca gtaggcaagg     1800
tggtgccctt cttcgaggct aaggtggtgg acttggacac cggtaagaca ctgggtgtga    1860
accagcgcgg cgagctgtgc gtccgtggcc ccatgatcat gagcggctac gttaacaacc    1920
ccgaggctac aaacgctctc atcgacaagg acggctggct gcacagcggc gacatcgcct    1980
actgggacga ggacgagcac ttcttcatcg tggaccggct gaagagcctg atcaaataca    2040
agggctacca ggtagcccca gccgaactgg agagcatcct gctgcaacac cccaacatct    2100
tcgacgccgg ggtcgccggc ctgcccgacg acgatgccgg cgagctgccc gccgcagtcg    2160
tcgtgctgga acacggtaaa accatgaccg agaaggagat cgtggactat gtggccagcc    2220
aggttacaac cgccaagaag ctgcgcggtg gtgttgtgtt cgtggacgag gtgcctaaag    2280
gactgaccgg caagttggac gcccgcaaga tccgcgagat tctcattaag gccaagaagg    2340
gcggcaagat cgccgtgtaa gaattctgca gatatccagc acagtggcgg ccgctcgagt    2400
ctagagggcc cgtttaaacc cgctgatcag cctcgactgt gccttctagt tgccagccat    2460
ctgttgtttg cccctccccc gtgccttcct tgaccctgga aggtgccact cccactgtcc    2520
tttcctaata aaatgaggaa attgcatcgc attgtctgag taggtgtcat tctattctgg    2580
ggggtggggt ggggcaggac agcaagggg aggattggga agacaatagc aggcatgctg    2640
gggatgcggt gggctctatg gcttctactg ggcggtttta tggacagcaa gcgaaccgga    2700
attgccagct ggggcgccct ctggtaaggt tgggaagccc tgcaaagtaa actggatggc    2760
tttctcgccg ccaaggatct gatggcgcag gggatcaagc tctgatcaag agacaggatg    2820
aggatcgttt cgcatgattg aacaagatgg attgcacgca ggttctccgg ccgcttgggt    2880
ggagaggcta ttcggctatg actgggcaca acagacaatc ggctgctctg atgccgccgt    2940
gttccggctg tcagcgcagg ggcgcccggt tctttttgtc aagaccgacc tgtccggtgc    3000
cctgaatgaa ctgcaagacg aggcagcgcg gctatcgtgg ctggccacga cgggcgttcc    3060
ttgcgcagct gtgctcgacg ttgtcactga agcgggaagg gactggctgc tattgggcga    3120
agtgccgggg caggatctcc tgtcatctca ccttgctcct gccgagaaag tatccatcat    3180
ggctgatgca atgcggcggc tgcatacgct tgatccggct acctgcccat tcgaccacca    3240
agcgaaacat cgcatcgagc gagcacgtac tcggatggaa gccggtcttg tcgatcagga    3300
tgatctggac gaagagcatc aggggctcgc gccagccgaa ctgttcgcca ggctcaaggc    3360
gagcatgccc gacggcgagg atctcgtcgt gacccatggc gatgcctgct tgccgaatat    3420
catggtggaa aatggccgct tttctggatt catcgactgt ggccggctgg gtgtggcgga    3480
ccgctatcag gacatagcgt tggctacccg tgatattgct gaagagcttg gcggcgaatg    3540
ggctgaccgc ttcctcgtgc tttacggtat cgccgctccc gattcgcagc gcatcgcctt    3600
ctatcgcctt cttgacgagt tcttctgaat tattaacgct tacaatttcc tgatgcggta    3660
ttttctcctt acgcatctgt gcggtatttc acaccgcata caggtggcac ttttcgggga    3720
aatgtgcgcg gaacccctat ttgtttattt ttctaaatac attcaaatat gtatccgctc    3780
atgagacaat aaccctgata aatgcttcaa taatagcacg tgtgtcagtt agggtgtgga    3840
aagtccccag gctccccagg caggcagaag tatgcaaagc atgcatctca attagtcagc    3900
```

```
aaccaggtgt ggaaagtccc caggctcccc agcaggcaga agtatgcaaa gcatgcatct   3960
caattagtca gcaaccatag tcccgcccct aactccgccc atcccgcccc taactccgcc   4020
cagttccgcc cattctccgc cccatggctg actaattttt tttatttatg cagaggccga   4080
ggccgcctct gcctctgagc tattccagaa gtagtgagga ggcttttttg gaggcctagg   4140
cttttgcaaa aagctcccgg gagcttgtat atccattttc ggatctgatc aagagacagg   4200
atgaggatcg tttcgcatgg cttcgtaccc ctgccatcaa cacgcgtctg cgttcgacca   4260
ggctgcgcgt tctcgcggcc ataacaaccg acgtacggcg ttgcgccctc gccggcaaca   4320
aaaagccacg gaagtccgcc tggagcagaa aatgcccacg ctactgcggg tttatataga   4380
cggtccccac gggatgggga aaccaccac cacgcaactg ctggtggccc tgggttcgcg   4440
cgacgatatc gtctacgtac ccgagccgat gacttactgg cgggtgttgg gggcttccga   4500
gacaatcgcg aacatctaca ccacacaaca ccgcctcgac cagggtgaga tatcggccgg   4560
ggacgcggcg gtggtaatga caagcgccca gataacaatg gcatgccttt atgccgtgac   4620
cgacgccgtt ctggctcctc atatcggggg ggaggctggg agctcacatg ccccgccccc   4680
ggccctcacc ctcatcttcg accgccatcc catcgccgcc ctcctgtgct acccggccgc   4740 gcgataccttt atgggcagca tgaccccca ggccgtgctg gcgttcgtgg ccctcatccc   4800
gccgaccttg cccggcacaa acatcgtgtt ggggccctt ccggaggaca gacacatcga   4860
ccgcctggcc aaacgccagc gccccggcga gcggcttgac ctggctatgc tggccgcgat   4920
tcgccgcgtt tatgggctgc ttgccaatac ggtgcggtat ctgcagggcg gcgggtcgtg   4980
gcgggaggat tggggacagc tttcggggggc ggccgtgccg ccccagggtg ccgagcccca   5040
gagcaacgcg ggcccacgac cccatatcgg ggacacgtta tttaccctgt ttcgggcccc   5100
cgagttgctg gccccccaacg gcgacctgta taacgtgttt gcctgggctt tggacgtctt   5160
ggccaaacgc ctccgtccca tgcatgtctt tatcctggat tacgaccaat cgcccgccgg   5220
ctgccgggac gccctgctgc aacttacctc cgggatggtc cagacccacg tcaccacccc   5280
aggctccata ccgacgatct gcgacctggc gcgcacgttt gcccgggaga tgggggaggc   5340
taactgagcg ggactctggg gttcgaaatg accgaccaag cgacgcccaa cctgccatca   5400
cgagatttcg attccaccgc cgccttctat gaaaggttgg gcttcggaat cgttttccgg   5460
gacgccggct ggatgatcct ccagcgcggg gatctcatgc tggagttctt cgcccacccc   5520
aacttgttta ttgcagctta taatggttac aaataaagca atagcatcac aaatttcaca   5580
aataaagcat ttttttcact gcattctagt tgtggtttgt ccaaactcat caatgtatct   5640
tatcatgtct gtaaacttgt ttattgcagc ttataatggt tacaaataaa gcaatagcat   5700
cacaaatttc acaaataaag cattttttc actgcattc agttgtggtt tgtccaaact   5760
catcaatgta tcttatcatg tctggatctg atcactgctt gagcctagga gatccgcacg   5820
tgctaaaact tcatttttaa tttaaaagga tctaggtgaa gatcctttt gataatctca   5880 tgaccaaaat cccttaacgt gagttttcgt tccactgagc gtcagacccc gtagaaaaga   5940
tcaaaggatc ttcttgagat cctttttttc tgcgcgtaat ctgctgcttg caaacaaaaa   6000
aaccaccgct accagcggtg gtttgtttgc cggatcaaga gctaccaact cttttccga   6060 aggtaactgg cttcagcaga gcgcagatac caaatactgt ccttctagtg tagccgtagt   6120
taggccacca cttcaagaac tctgtagcac cgcctacata cctcgctctg ctaatcctgt   6180
taccagtggc tgctgccagt ggcgataagt cgtgtcttac cgggttggac tcaagacgat   6240
```

| | |
|---|---|
| agttaccgga taaggcgcag cggtcgggct gaacgggggg ttcgtgcaca cagcccagct | 6300 |
| tggagcgaac gacctacacc gaactgagat acctacagcg tgagctatga aaagcgcca | 6360 |
| cgcttcccga agggagaaag gcggacaggt atccggtaag cggcagggtc ggaacaggag | 6420 |
| agcgcacgag ggagcttcca gggggaaacg cctggtatct ttatagtcct gtcgggtttc | 6480 |
| gccacctctg acttgagcgt cgattttgt gatgctcgtc agggggggcgg agcctatgga | 6540 |
| aaaacgccag caacgcggcc ttttacggt tcctgggctt ttgctggcct tttgctcaca | 6600 |
| tgttctt | 6607 |

<210> SEQ ID NO 2
<211> LENGTH: 5981
<212> TYPE: DNA
<213> ORGANISM: Artificial Sequence
<220> FEATURE:
<223> OTHER INFORMATION: Recombinant

<400> SEQUENCE: 2

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| ctatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgccaccatg gaagatgcca | 720 |
| aaaacattaa gaagggccca cgccattct cccactcga agacgggacc gccggcgagc | 780 |
| agctgcacaa agccatgaag cgctacgccc tggtgcccgg caccatcgcc tttaccgacg | 840 |
| cacatatcga ggtggacatt acctacgccg agtacttcga gatgagcgtt cggctggcag | 900 |
| aagctatgaa gcgctatggg ctgaatacaa accatcggat cgtggtgtgc agcgagaata | 960 |
| gcttgcagtt cttcatgccc gtgttgggtg ccctgttcat cggtgtggct gtggccccag | 1020 |
| ctaacgacat ctacaacgag cgcgagctgc tgaacagcat gggcatcagc cagcccaccg | 1080 |
| tcgtattcgt gagcaagaaa gggctgcaaa agatcctcaa cgtgcaaaag aagctaccga | 1140 |
| tcatacaaaa gatcatcatc atggatagca agaccgacta ccagggcttc caaagcatgt | 1200 |
| acaccttcgt gacttcccat ttgccacccg gcttcaacga gtacgacttc gtgcccgaga | 1260 |
| gcttcgaccg ggacaaaacc atcgccctga tcatgaacag tagtggcagt accggattgc | 1320 |
| ccaagggcgt agccctaccg caccgcaccg cttgtgtccg attcagtcat gcccgcgacc | 1380 |
| ccatcttcgg caaccagatc atccccgaca ccgctatcct cagcgtggtg ccatttcacc | 1440 |
| acggcttcgg catgttcacc acgctgggct acttgatctg cggctttcgg gtcgtgctca | 1500 |
| tgtaccgctt cgaggaggag ctattcttgc gcagcttgca agactataag attcaatctg | 1560 |
| ccctgctggt gccacactta tttagcttct tcgctaagag cactctcatc gacaagtacg | 1620 |
| acctaagcaa cttgcacgag atcgccagcg gcggggcgcc gctcagcaag gaggtaggtg | 1680 |

```
aggccgtggc caaacgcttc cacctaccag gcatccgcca gggctacggc ctgacagaaa    1740
caaccagcgc cattctgatc accccgaag gggacgacaa gcctggcgca gtaggcaagg     1800
tggtgccctt cttcgaggct aaggtggtgg acttggacac cggtaagaca ctgggtgtga    1860 accagcgcg cgagctgtgc gtccgtggcc ccatgatcat gagcggctac gttaacaacc    1920
ccgaggctac aaacgctctc atcgacaagg acggctggct gcacagcggc gacatcgcct    1980
actgggacga ggacgagcac ttcttcatcg tggaccggct gaagagcctg atcaaataca    2040
agggctacca ggtagcccca gccgaactgg agagcatcct gctgcaacac cccaacatct    2100
tcgacgccgg ggtcgccggc ctgcccgacg acgatgccgg cgagctgccc gccgcagtcg    2160
tcgtgctgga acacggtaaa accatgaccg agaaggagat cgtggactat gtggccagcc    2220
aggttacaac cgccaagaag ctgcgcgtg gtgttgtgtt cgtggacgag gtgcctaaag     2280
gactgaccgg caagttggac gcccgcaaga tccgcgagat tctcattaag gccaagaagg    2340
gcggcaagat cgccgtgtaa gaattctgca gatatccagc acagtggcgg ccgctcgagt    2400
ctagagggcc cgtttaaacc cgctgatcag cctcgactgt gccttctagt tgccagccat    2460
ctgttgtttg cccctccccc gtgccttcct tgaccctgga aggtgccact cccactgtcc    2520
tttcctaata aaatgaggaa attgcatcgc attgtctgag taggtgtcat tctattctgg    2580
ggggtggggt gggcaggac agcaaggggg aggattggga agacaatagc aggcatgctg    2640
gggatgcggt gggctctatg gcttctactg ggcggtttta tggacagcaa gcgaaccgga    2700
attgccagct ggggcgccct ctggtaaggt tgggaagccc tgcaaagtaa actggatggc    2760
tttctcgccg ccaaggatct gatggcgcag gggatcaagc tctgatcaag agacaggatg    2820
aggatcgttt cgcatgattg aacaagatgg attgcacgca ggttctccgg ccgcttgggt    2880
ggagaggcta ttcggctatg actgggcaca acagacaatc ggctgctctg atgccgccgt    2940
gttccggctg tcagcgcagg ggcgcccggt tctttttgtc aagaccgacc tgtccggtgc    3000
cctgaatgaa ctgcaagacg aggcagcgcg gctatcgtgg ctggccacga cgggcgttcc    3060
ttgcgcagct gtgctcgacg ttgtcactga agcgggaagg gactggctgc tattgggcga    3120
agtgccgggg caggatctcc tgtcatctca ccttgctcct gccgagaaag tatccatcat    3180
ggctgatgca atgcggcggc tgcatacgct tgatccggct acctgcccat tcgaccacca    3240
agcgaaacat cgcatcgagc gagcacgtac tcggatggaa gccggtcttg tcgatcagga    3300
tgatctggac gaagagcatc aggggctcgc gccagccgaa ctgttcgcca ggctcaaggc    3360
gagcatgccc gacggcgagg atctcgtcgt gacccatggc gatgcctgct tgccgaatat    3420
catggtggaa aatggccgct tttctggatt catcgactgt ggccggctgg gtgtggcgga    3480
ccgctatcag gacatagcgt tggctacccg tgatattgct gaagagcttg gcggcgaatg    3540
ggctgaccgc ttcctcgtgc tttacggtat cgccgctccc gattcgcagc gcatcgcctt    3600
ctatcgcctt cttgacgagt tcttctgaat tattaacgct tacaatttcc tgatgcggta    3660
ttttctcctt acgcatctgt gcggtatttc acaccgcata caggtggcac ttttcgggga    3720
aatgtgcgcg gaacccctat ttgtttattt ttctaaatac attcaaatat gtatccgctc    3780
atgagacaat aaccctgata aatgcttcaa taatagcacg tgtgtcagtt agggtgtgga    3840
aagtccccag gctccccagg caggcagaag tatgcaaagc atgcatctca attagtcagc    3900
aaccaggtgt ggaaagtccc caggctcccc agcaggcaga gtatgcaaa gcatgcatct    3960 caattagtca gcaaccatag tccgccccct aactccgccc atcccgcccc taactccgcc    4020
```

```
cagttccgcc cattctccgc cccatggctg actaattttt tttatttatg cagaggccga    4080
ggccgcctct gcctctgagc tattccagaa gtagtgagga ggcttttttg gaggcctagg    4140
cttttgcaaa aagctcccgg ggccaccatg aaaagctta ccgacctcaa ctacacattg     4200
agtgtagtca ctctcatgaa tgatacttta cataccataa tggaggatcc tggaatggcg    4260
tattttccat acattgcttc tgtcctaact gtactattta cattacataa ggcctcggtt    4320
ccaaccatga agattgctct taaaacgtca aagtgttcat ataaagtaat caaatactgc    4380
attgtgtcaa ttttaacac tctattgaaa ctggctggat ataagaaaca aattactact     4440
aaagatgaaa ttgaaaggca atggacaga gttgtaaaag aaatgagacg tcagctggaa     4500
atgattgata agctaaccac tagagagatt gagcaagtcg aactacttaa acgaattcat    4560
gatatgttga taattaaacc agttgacaaa attgatatgt cacaagaatt taatcagaaa    4620
tatttcaaaa cgctaaatga ttgggctgaa ggtgaaaatc catatgaacc aaaagaggtg    4680
actgcatcat tgtgacccgg gagatggggg aggctaactg agcggactc tggggttcga     4740 aatgaccgac caagcgacgc ccaacctgcc atcacgagat ttcgattcca ccgccgcctt    4800
ctatgaaagg ttgggcttcg gaatcgtttt ccgggacgcc ggctggatga tcctccagcg    4860
cggggatctc atgctggagt tcttcgccca ccccaacttg tttattgcag cttataatgg    4920
ttacaaataa agcaatagca tcacaaattt cacaataaa gcatttttt cactgcattc     4980 tagttgtggt ttgtccaaac tcatcaatgt atcttatcat gtctgtaaac ttgtttattg    5040
cagcttataa tggttacaaa taaagcaata gcatcacaaa tttcacaaat aaagcatttt    5100
tttcactgca ttctagttgt ggtttgtcca aactcatcaa tgtatcttat catgtctgga    5160
tctgatcact gcttgagcct aggagatccg cacgtgctaa aacttcattt ttaatttaaa    5220
aggatctagg tgaagatcct tttgataat ctcatgacca aaatcccta acgtgagttt      5280 tcgttccact gagcgtcaga ccccgtagaa aagatcaaag gatcttcttg agatcctttt    5340
tttctgcgcg taatctgctg cttgcaaaca aaaaaaccac cgctaccagc ggtggtttgt    5400
ttgccggatc aagagctacc aactctttt ccgaaggtaa ctggcttcag cagagcgcag     5460
ataccaaata ctgtccttct agtgtagccg tagttaggcc accacttcaa gaactctgta    5520
gcaccgccta catacctcgc tctgctaatc ctgttaccag tggctgctgc cagtggcgat    5580
aagtcgtgtc ttaccgggtt ggactcaaga cgatagttac cggataaggc gcagcggtcg    5640
ggctgaacgg ggggttcgtg cacacagccc agcttggagc gaacgaccta ccgaactg      5700 agatacctac agcgtgagct atgagaaagc gccacgcttc ccgaagggag aaaggcggac    5760
aggtatccgg taagcggcag ggtcggaaca ggagagcgca cgagggagct tccaggggga    5820
aacgcctggt atctttatag tcctgtcggg tttcgccacc tctgacttga gcgtcgattt    5880
ttgtgatgct cgtcaggggg gcggagccta tggaaaaacg ccagcaacgc ggccttttta    5940
cggttcctgg gcttttgctg gccttttgct cacatgttct t                        5981
```

<210> SEQ ID NO 3
<211> LENGTH: 1137
<212> TYPE: DNA
<213> ORGANISM: Artificial Sequence
<220> FEATURE:
<223> OTHER INFORMATION: Recombinant

<400> SEQUENCE: 3

```
tttcgcatgg cttcgtaccc ctgccatcaa cacgcgtctg cgttcgacca ggctgcgcgt     60
tctcgcggcc ataacaaccg acgtacggcg ttgcgccctc gccggcaaca aaaagccacg    120
```

```
gaagtccgcc tggagcagaa aatgcccacg ctactgcggg tttatataga cggtccccac        180
gggatgggga aaaccaccac cacgcaactg ctggtggccc tgggttcgcg cgacgatatc        240
gtctacgtac ccgagccgat gacttactgg cgggtgttgg gggcttccga gacaatcgcg        300
aacatctaca ccacacaaca ccgcctcgac cagggtgaga tatcggcggg ggacgcggcg        360
gtggtaatga caagcgccca gataacaatg gcatgccctt atgccgtgac cgacgccgtt        420
ctggctcctc atatcggggg ggaggctggg agctcacatg ccccgccccc ggccctcacc        480
ctcatcttcg accgccatcc catcgccgcc ctcctgtgct acccggccgc gcgatacctt        540
atgggcagca tgaccccca ggccgtgctg gcgttcgtgg ccctcatccc gccgaccttg         600
cccggcacaa acatcgtgtt gggggccctt ccggaggaca gacacatcga ccgcctggcc        660
aaacgccagc gccccggcga gcggcttgac ctggctatgc tggccgcgat cgccgcgtt        720 tatgggctgc ttgccaatac ggtgcggtat ctgcagggcg cgggtcgtg gcgggaggat         780 tggggacagc tttcggggc ggccgtgccg ccccagggtg ccgagcccca gagcaacgcg        840
ggcccacgac cccatatcgg ggacacgtta tttaccctgt ttcgggcccc cgagttgctg        900
gcccccaacg gcgacctgta taacgtgttt gcctgggctt tggacgtctt ggccaaacgc        960
ctccgtccca tgcatgtctt tatcctggat tacgaccaat cgcccgccgg ctgccgggac       1020
gccctgctgc aacttacctc cgggatggtc cagacccacg tcaccacccc aggctccata       1080
ccgacgatct gcgacctggc gcgcacgttt gcccgggaga tgggggaggc taactga         1137

<210> SEQ ID NO 4
<211> LENGTH: 535
<212> TYPE: DNA
<213> ORGANISM: Artificial Sequence
<220> FEATURE:
<223> OTHER INFORMATION: Recombinant

<400> SEQUENCE: 4
ggccaccatg gaaaagctta ccgacctcaa ctacacattg agtgtagtca ctctcatgaa         60
tgatacttta cataccataa tggaggatcc tggaatggcg tatttttccat acattgcttc        120 tgtcctaact gtactattta cattacataa ggcctcggtt ccaaccatga agattgctct        180
taaaacgtca aagtgttcat ataaagtaat caaatactgc attgtgtcaa tttttaacac        240
tctattgaaa ctggctggat ataaagaaca aattactact aaagatgaaa ttgaaaggca        300
aatggacaga gttgtaaaag aaatgagacg tcagctggaa atgattgata agctaaccac        360
tagagagatt gagcaagtcg aactacttaa acgaattcat gatatgttga taattaaacc        420
agttgacaaa attgatatgt cacaagaatt taatcagaaa tatttcaaaa cgctaaatga        480
ttgggctgaa ggtgaaaatc catatgaacc aaaagaggtg actgcatcat tgtga           535

<210> SEQ ID NO 5
<211> LENGTH: 1660
<212> TYPE: DNA
<213> ORGANISM: Artificial Sequence
<220> FEATURE:
<223> OTHER INFORMATION: Recombinant

<400> SEQUENCE: 5
cgccaccatg gaagatgcca aaaacattaa gaagggccca gcgccattct acccactcga         60
agacgggacc gccggcgagc agctgcacaa agccatgaag cgctacgccc tggtgccgg        120 caccatcgcc tttaccgacg cacatatcga ggtggacatt acctacgccg agtacttcga        180
```

-continued

```
gatgagcgtt cggctggcag aagctatgaa gcgctatggg ctgaatacaa accatcggat      240
cgtggtgtgc agcgagaata gcttgcagtt cttcatgccc gtgttgggtg ccctgttcat      300
cggtgtggct gtggccccag ctaacgacat ctacaacgag cgcgagctgc tgaacagcat      360
gggcatcagc cagcccaccg tcgtattcgt gagcaagaaa gggctgcaaa agatcctcaa      420
cgtgcaaaag aagctaccga tcatacaaaa gatcatcatc atggatagca agaccgacta      480
ccagggcttc caaagcatgt acaccttcgt gacttcccat ttgccacccg gcttcaacga      540
gtacgacttc gtgcccgaga gcttcgaccg ggacaaaacc atcgccctga tcatgaacag      600
tagtggcagt accggattgc caagggcgt agccctaccg caccgcaccg cttgtgtccg       660
attcagtcat gcccgcgacc ccatcttcgg caaccagatc atccccgaca ccgctatcct      720
cagcgtggtg ccatttcacc acggcttcgg catgttcacc acgctgggct acttgatctg      780
cggctttcgg gtcgtgctca tgtaccgctt cgaggaggag ctattcttgc gcagcttgca      840
agactataag attcaatctg ccctgctggt gcccacacta tttagcttct tcgctaagag      900
cactctcatc gacaagtacg acctaagcaa cttgcacgag atcgccagcg gcgggcgcc       960 gctcagcaag gaggtaggtg aggccgtggc caaacgcttc cacctaccag gcatccgcca     1020
gggctacggc ctgacagaaa caaccagcgc cattctgatc cccccgaagg ggacgacaa      1080 gcctggcgca gtaggcaagg tggtgcccttc cttcgaggct aaggtggtgg acttggacac     1140
cggtaagaca ctgggtgtga accagcgcgg cgagctgtgc gtccgtggcc ccatgatcat     1200
gagcggctac gttaacaacc cgaggctac aaacgctctc atcgacaagg acggctggct      1260
gcacagcggc gacatcgcct actgggacga ggacgagcac ttcttcatcg tggaccggct     1320
gaagagcctg atcaaataca agggctacca ggtagcccca gccgaactgg agagcatcct     1380
gctgcaacac cccaacatct tcgacgccgg ggtcgccggc ctgcccgacg acgatgccgg     1440
cgagctgccc gccgcagtcg tcgtgctgga acacggtaaa accatgaccg agaaggagat     1500
cgtggactat gtgccagcc aggttacaac cgccaagaag ctgcgcgtg tgttgtgtt       1560 cgtggacgag gtgcctaaag gactgaccgg caagttggac gcccgcaaga tccgcgagat     1620
tctcattaag gccaagaagg gcggcaagat cgccgtgtaa                          1660
```

<210> SEQ ID NO 6
<211> LENGTH: 1908
<212> TYPE: RNA
<213> ORGANISM: Hepatitis C virus

<400> SEQUENCE: 6

```
gccaccaugg cacccaucac cgccuacagc cagcagacca gaggacugcu gggcugcauc       60
aucaccagcc ugaccggcag agacaagaac cagguggaag cgaggugca ggucgugucu      120 accgccaccc agagcuuucu ggccaccugu gugaacggcg ugcuggac cguguaucac       180 ggcgcuggca gcaagacacu ggccggaccu aagggcccug ugaccagau guacaccaac      240 guggaccagg accucguggg cuggccugcu ccuccuggcg cuagaagccu gaccccuugu     300
accugcggca gcagcgaccu guaccugguc accagacacg ccgacgugau ccccgucaga    360
agaagaggcg acagcagagg cagccugcug agcccuagac ccguguccua ccugaagggc     420
agcucuggcg gaccucugcu guguccuucu ggacacgcug ugggcaucuu cagagccgcc    480
guguguacca gaggcguggc caaagcugug gacuucugc ccgucgagag cauggaaacc     540
accaugcgga gccccguguu caccgacaau agcagcccuc cgccgugcc cgagacauuc    600 caggugcac aucugcacgc cccuaccggc agcggcaaga gcacaaaagu gccugccgcc    660
```

```
uaugccgccc agggcuacaa agugcuggug cugaauccua gcguggccgc cacacugggc      720
uucggcgccu acaugucuaa ggcucacggc accgacccca caucagaaac cggcgugcgg      780
accaucacaa caggcgcccc uaucaccuac ucuaccuacg gcaaguuccu ggccgacggc      840
ggcuguucug gcggagccua cgacaucauc aucgcgacg agugccacag caccgacagc       900
accaccaucc uggcaucgg caccgugcug gaucaggccg aaacagccgg cgcuagacug       960
guggugcugg ccacagcuac accuccaggc agcgugacag ugccccaccc caauaucgag     1020
gaaguggccc ugagcaauau cggcgagauc ccauucuacg caaggccau ccccaucgag      1080 acaaucaagg gcggcagaca ccugaucuuu gccacagca agaagaagug cgacgagcug      1140
gccgccaagc ugucuggccu gggacugaau gcuguggccu acuacagagg ccuggacgug     1200
uccgugaucc ccacaucugg ggacguggug guggugcua ccgacgcccu gaugaccggc      1260
uucaccggcg acuucgacag cgugaucgac ugcaauaccu gcgugaccca gacaguggac     1320
uucagccugg accccaccuu caccaucgaa accaccaccg ugcccagga cgccgugucu      1380 agaagccaga gaagaggcag aaccggcaga ggcagacggg gcaucuacag auucgugacc     1440
ccuggcgaac ggcccagcgg cauguuugau agcagcgugc ugugcgagug cuacgacgcc     1500
ggcugugcuu gguacgagcu gaccccugcc gagacaagcg ugcggcugag agccuaccug     1560
aacaccccug gccugcccgu gugucaggac caccuggaau ucuggagag cguguucaca     1620 ggccugaccc acaucgacgc ccacuuucug agccagacca agcaggccgg cgagaacuuc     1680
ccuuaccuga ccgccuacca ggccaccgug ugugucuaga cacaggcccc uccacccagc    1740
ugggaccaga uguggaagug ccugauccgg cugaagccca cccugcacgg accuaccccu     1800
cugcuguaua cucgggcgc cgugcagaac gaguggugc ugacccaccc caucaccaag      1860
uacaucaugg ccugcaugag cgccgaccug gaagugguca ccugauaa                 1908
```

<210> SEQ ID NO 7
<211> LENGTH: 280
<212> TYPE: DNA
<213> ORGANISM: Mus musculus

<400> SEQUENCE: 7

```
atggccacgt gcctgttcct cctgggcctt ttcctgctgc tgccacgacc tgtccctgct       60
ccctgctaca ctgccactcg gtcagaatgc aagcagaagc acaagttcgt gccaggtgta      120
tggatggctg gggaaggcat ggatgtgact accctccgcc gctccggctc cttcccagtg      180
aacacacaga ggttcctgag gcctgaccgc acctgcaccc tctgtaaaaa ctccctaatg      240
agagacgcca cacagcgcct acctgtggca atcacccact                            280
```

<210> SEQ ID NO 8
<211> LENGTH: 17
<212> TYPE: PRT
<213> ORGANISM: Foot-and-mouth disease virus

<400> SEQUENCE: 8

```
Asn Phe Asp Leu Leu Lys Leu Ala Gly Asp Val Glu Ser Asn Pro Gly
1               5                   10                  15

Pro
```

<210> SEQ ID NO 9
<211> LENGTH: 51
<212> TYPE: DNA
<213> ORGANISM: Foot-and-mouth disease virus

```
<400> SEQUENCE: 9
aacttcgacc tgctgaagct ggccggcgac gtggagagca accccggccc c        51

<210> SEQ ID NO 10
<211> LENGTH: 9
<212> TYPE: PRT
<213> ORGANISM: Artificial Sequence
<220> FEATURE:
<223> OTHER INFORMATION: immunodominant peptide

<400> SEQUENCE: 10

Leu Met Tyr Arg Phe Glu Glu Glu Leu
1               5

<210> SEQ ID NO 11
<211> LENGTH: 20
<212> TYPE: DNA
<213> ORGANISM: Artificial Sequence
<220> FEATURE:
<223> OTHER INFORMATION: MLV F primer

<400> SEQUENCE: 11
gaggtcgggt ggaagtacca                                            20

<210> SEQ ID NO 12
<211> LENGTH: 20
<212> TYPE: DNA
<213> ORGANISM: Artificial Sequence
<220> FEATURE:
<223> OTHER INFORMATION: MLV R primer

<400> SEQUENCE: 12
tgcatcttgg cctttcctt                                             20

<210> SEQ ID NO 13
<211> LENGTH: 20
<212> TYPE: DNA
<213> ORGANISM: Artificial Sequence
<220> FEATURE:
<223> OTHER INFORMATION: RPL13a F primer

<400> SEQUENCE: 13
tagggccaaa ccccgttctg                                            20

<210> SEQ ID NO 14
<211> LENGTH: 20
<212> TYPE: DNA
<213> ORGANISM: Artificial Sequence
<220> FEATURE:
<223> OTHER INFORMATION: RPL13a R primer

<400> SEQUENCE: 14
gccggtggaa gttgggtagg                                            20
```

CELLULAR VACCINE AND METHOD OF INDUCING AN IMMUNE RESPONSE IN A SUBJECT

TECHNICAL FIELD

The invention relates to methods of inducing or enhancing an immune response against an immunogen in a subject. The invention further includes isolated nucleic acid vaccines, cellular vaccines, fusion proteins, expression vectors, vaccines, and immunogenic compositions for use therein.

BACKGROUND ART

There are approximately 33 million individuals with human immunodeficiency virus (HIV) infection worldwide. Many will die as a result of the infection which has already claimed more than 23 million deaths and 2.7 million people are newly infected each year (International AIDS vaccine initiative (IAVI), AIDS vaccine blueprint, A challenge to the field, A road map for progress, 2008, ISBN #0-9792432-8-9). Over 80% of new HIV-1 infections arise in the developing world.

There are approximately 10,000 new cases of hepatitis C virus (HCV) infections in Australia each year, 220,000 HCV-positive individuals in the country (Razali K et al., 2007, Drug Alcohol Depend 91: 228-235), approximately 200 million infected individuals in the world and an estimated 3-4 million new infections each year (Bonner, J. E., Esserman, D., Evon, D. M., 2012, Reliability and validity of a self-efficacy instrument for hepatitis C antiviral treatment regimens, J Viral Hep 19: 316-26). In developing countries, many infections result from poor medical practice (Hauri, A. M, Armstrong, G. L, Hutin Y. J, 2004). The global burden of disease attributable to contaminated injections given in health care settings. Int. J. STD AIDS, 15 (2004), pp. 7-16).

Effective vaccines are necessary to control the spread of these agents. However, existing licensed vaccines often depend on neutralising antibody to induce protection, but neutralising antibody may not effectively control challenge by HCV and HIV. These viruses mutate rapidly and generate neutralising antibody (NAb)-escape mutants. As conventional vaccines elicit NAb, an alternative approach to design vaccines for these viruses is necessary.

There exists a need for alternative vaccines for HIV and HCV. The present invention seeks to overcome, or at least ameliorate, one or more of the deficiencies of the prior art mentioned above, or to provide the consumer with a useful or commercial choice.

The above discussion of the background art is intended to facilitate an understanding of the present invention only. The discussion is not an acknowledgement or admission that any of the material referred to is or was part of the common general knowledge as at the priority date of the application.

SUMMARY OF INVENTION

According to the invention there is provided a method of inducing or enhancing an immune response against an immunogen in a subject. The method includes the steps of:
  expressing the immunogen in a cell, and
  administering the cell to the subject, thereby inducing a pro-inflammatory immune response.

The cell may be a somatic cell.

The method may include the further step of inducing cell death (necrosis) in the cell. The step of inducing cell death (necrosis) may be carried out before or after the step of administering the cell to the subject. The step of inducing cell death may result in lysis of the cell after vaccination. Lysis of the cell may occur in a subject after administration, thereby resulting in induction of a pro-inflammatory immune response upon processing of the lysed cell by the immune system of the subject. Typically, when the method includes the further step of inducing cell death in the cell, the cell is provided as a non-antigen presenting cell, such as a somatic cell. The cell may be selected from the group comprising allogeneic cells, HEK 293T cells and recombinantly expressing Human Leucocyte Antigen (HLA) class I and II molecules and Huh7 cells. Preferably, the somatic cell is either allogeneic or autologous. The cell may also be selected from cells which cannot express HLA proteins such as, but not limited to, CIR cells, K562 and LCL721.221 cells.

Alternatively the cell may be an antigen-presenting cell (APC).

The method may include the further step of the step of expressing the immunogen in the cell may further include the step of presenting the expressed immunogen on the surface of the cell.

When the cell is an APC, the step of expressing the immunogen in the cell may further include the step of presenting the expressed immunogen on the surface of the cell. The step of presenting the expressed immunogen on the surface of the cell may result in processing of the expressed immunogen-presenting APC by the subjects immune system, thereby inducing a pro-inflammatory immune response in the subject. The APC may be selected from the group comprising: allogeneic cells, dendritic cells (DC), macrophages, B cells, Langerhans cells, Kupffer cells. Preferably, the APC is either allogeneic or autologous.

The cell may co-express HLA. The HLA expression by the cell may be the result of a natural process or due to recombinant expression of HLA. That is, the HLA expression may be as a result of HLA expression by the cell by endogenous processes. Alternatively, the HLA expression may occur as a result of recombinant engineering and protein production.

The immunogen may be derived from HCV. When the immunogen is derived from HCV, the cell typically does not co-express HLA.

The immunogen may be derived from HIV. When the immunogen is derived from HIV, the cell may or may not co-express HLA.

In one preferred embodiment, the immune response is against an endogenous antigen so that after cell lyse the antigen is treated as exogenous antigen by the immune system resulting in cross presentation of the antigen. In a further aspect, the invention is a method of inducing or enhancing an immune response against an immunogen in a subject including the steps of:
  expressing the endogenous immunogen in a somatic cell or an APC;
  inducing necrosis in the cell; and
  administering the cell to the subject, thereby inducing a pro-inflammatory immune response.

Further features of the invention provide for the step of administering the cell to the subject, thereby inducing a pro-inflammatory immune response, to be carried out by processing of the immunogen by an APC of the subject via the class II pathway, the presented immunogen detectable by naïve CD4$^+$ T cells.

Still further features of the invention provide for the step of administering the cell to the subject, thereby inducing a pro-inflammatory immune response, to be carried out by processing of the immunogen by the APC via the class I pathway, the presented immunogen detectable by naïve CD8⁺ T cells.

In a further aspect, the invention is a method of inducing or enhancing an immune response against an immunogen in a subject including the steps of:
  expressing the endogenous immunogen in a cell, thereby presenting the
  endogenous immunogen; and
  administering to the subject the endogenous immunogen-presenting cell, thereby inducing a pro-inflammatory immune response.

In one example the cell is an APC.

Further features of the invention provide for the step of expressing an immunogen in an APC, thereby presenting the immunogen, to be carried out by processing of the immunogen by the APC via the class II pathway, the presented immunogen detectable by naïve CD4⁺ T cells.

Still further features of the invention provide for the step of expressing an immunogen in an APC, thereby presenting the immunogen, to be carried out by processing of the immunogen by the APC via the class I pathway, the presented immunogen detectable by naïve CD8⁺ T cells.

The cell of the method of the invention may be selected from the group comprising allogeneic or autologous cells, dendritic cells (DC), peripheral blood mononuclear cells (PBMC), macrophages, B cells, Langerhans cells, Kupffer cells, HEK 293T cells, HEK293T cells recombinantly expressing HLA class I and II molecules and Huh7 cells. Preferably, the APC is allogeneic or autologous.

The immunogen may be of viral origin. As discussed above, the immunogen may be of HIV origin. The immunogen of HIV origin may be presented together with a Human Leucocyte Antigen (HLA) such as, but not limited to, HLA A*0201, HLA B*0702, HLA Cw7, DRB1, DRB3, DRB4 and DRB5. The immunogen, when derived from HIV, may be selected from, but not limited to, the HIV gag and/or env proteins. Alternatively, the immunogen may be derived from SIV, such as the SIV gag and/or env proteins.

In one embodiment, the method of inducing or enhancing an immune response against an HIV protein in a subject includes the steps of:
  expressing HIV protein and human leucocyte antigen (HLA) in a cell;
  inducing necrosis in the cell; and
  administering to the subject the HIV protein and human leucocyte antigen (HLA) expressing cell, thereby inducing a pro-inflammatory immune response against the HIV protein and the HLA proteins.

Preferably, the HLA is selected from the group consisting of: HLA-A*0101, HLA-A*0301 and HLA-A*2901 and HLA DP, DQ and DR.

The HIV antigen may be any HIV-derived protein, such as, but not limited to, gp120 or gag.

In a further embodiment, the method of inducing or enhancing an immune response against an HIV protein in a subject includes the steps of:
  expressing HIV protein in a cell;
  inducing necrosis in the cell; and
  administering to the subject the HIV protein expressing cell, thereby inducing a pro-inflammatory immune response against the HIV protein.

Further features of the invention provide for the step of inducing cell death in the cell to be carried out by inducing necrosis. The step of inducing necrosis in the cell may be carried out by exposing the cell to necrosis-inducing conditions, such as, but not limited to, heating the immunogen-presenting cell to 63° C. for at least 30 min.

Alternatively, the step of inducing cell death in the cell may be carried out by exposing the cell to a necrosis-inducing agent or expressing the necrosis agent in the cell (internal expression in the cell, rather than external exposure to the necrosis agent). Examples of the necrosis-inducing agent may include, but are not limited to, thymidine kinase (TK), perforin, granzyme, caspase, RIP proteins 1&3, adenovirus penton fibre, NSP4, streptolysin O, anthrolysin, PB-F2, and functional fragments thereof.

In another embodiment, the method of inducing or enhancing an immune response against an HIV protein in a subject includes the steps of:
  expressing HIV protein and human leucocyte antigen (HLA) in a cell; and
  administering to the subject the HIV protein and human leucocyte antigen (HLA) expressing APC, thereby inducing a pro-inflammatory immune response against the HIV protein.

Preferably, the cell is an APC.

Alternatively, the immunogen may be of HCV origin. The immunogen when of HCV origin may be selected from, but is not limited to, the following HCV proteins: core, E1/E2, p7, NS2, NS3, NS4A, NS4B, NS5A, NS5B In a further embodiment the method of inducing or enhancing an immune response against an HCV protein in a subject includes the steps of:
  expressing HCV protein in a cell, thereby presenting the HCV protein;
  inducing necrosis in the cell; and
  administering to the subject the HCV protein expressing cell, thereby inducing a pro-inflammatory immune response against HCV.

Further features of the invention provide for the step of inducing cell death in the cell to be carried out by inducing necrosis. The step of inducing necrosis in the cell may be carried out by exposing the cell to necrosis-inducing conditions, such as, but not limited to, heating the immunogen-presenting cell to 63° C. for at least 30 min.

Alternatively, the step of inducing necrosis in the cell may be carried out by exposing the cell to a necrosis-inducing agent or expressing the necrosis agent in the cell (internal expression in the cell, rather than external exposure to the necrosis agent). Examples of the necrosis inducing agent may include, but are not limited to, thymidine kinase (TK), perforin, granzyme, caspase, RIP proteins 1&3, adenovirus penton fibre, NSP4, streptolysin O, anthrolysin, PB-F2, and functional fragments thereof.

The cell may undergo lysis after the step of administering the cell to the subject.

In another embodiment, the method of inducing or enhancing an immune response against an HCV protein in a subject includes the steps of:
  expressing HCV protein in an APC or other somatic cell, thereby presenting the HCV; and
  administering to the subject the HCV protein expressing APC, thereby inducing a pro-inflammatory immune response against HCV.

In a further embodiment, the method of inducing or enhancing an immune response against an HCV protein in a subject includes the steps of:
  expressing HCV protein in the cell; and
  administering to the subject the HCV protein expressing cell, thereby inducing a pro-inflammatory immune response against HCV.

The invention also provides for a nucleic acid vaccine comprising a nucleic acid sequence having:
- a first nucleic acid sequence having a first nucleic acid sequence encoding a polypeptide having cell death inducing activity; and
- a second nucleic acid sequence having a second nucleic acid sequence encoding an immunogenic polypeptide.

The nucleic acid vaccine may be a DNA vaccine.

The first sequence and the second sequence may be bicistronic.

The nucleic acid vaccine may further include one or more promoters, such as, but not limited to, a CMV promoter or a SV40 promoter. The nucleic acid vaccine may also include a viral internal ribosome entry site (IRES), such as but not limited to, the encephalomyocarditis virus (EMCV) IRES.

In one embodiment, the nucleic acid vaccine includes:
- a CMV promoter operatively linked to the first nucleic acid sequence; and
- a SV40 promoter operatively linked to the second nucleic acid sequence.

The nucleic acid vaccine may include the first nucleic acid sequence and the second nucleic acid sequence operably linked for monocistronic expression by way of, for example, by the encephalomyocarditis virus internal ribosome entry site (EMCV IRES) and optionally includes an intervening nucleic acid sequence between the first nucleic acid sequence and the second nucleic acid sequence, the intervening nucleic acid sequence encoding the FMDV 2A protease or other autoprotease sequence.

Thus, in another embodiment, the nucleic acid vaccine includes:
- an EMCV IRES operatively linked to the first nucleic acid sequence.

Alternatively, nucleic acids having a DNA sequence encoding a protease cleavage site may be inserted between the first and second nucleic acid sequence such as, but not limited to, the foot and mouth disease virus 2A protease sequence. It will be appreciated that a vector may be designed to insert the foot and mouth disease virus 2A protease nucleic acid sequence between the upstream first nucleic acid sequence which encodes the immunogen and the downstream second nucleic acid sequence which encodes the polypeptide having necrosis inducing activity. The resultant fusion protein produced would be expected to include the immunogen fused to the protease and the polypeptide having cell death inducing activity. The 2A protease has self-cleaving activity which would be expected to result in the production of the upstream and downstream proteins as independent proteins by co- or post-translational cleavage. The amino acid sequence of the 2A protease as described herein as SEQ ID NO: 8, and the DNA sequence of the 2A protease as described herein as SEQ ID NO: 9.

The invention also provides for a nucleic acid vaccine comprising:
- a first nucleic acid sequence having a first nucleic acid sequence encoding a polypeptide having necrosis inducing activity;
- a second nucleic acid sequence having a second nucleic acid sequence encoding an immunogenic polypeptide and
- an intervening nucleic acid molecule between the first and second nucleic acid sequences, having a nucleic acid sequence encoding a protease.

Further features of the invention provide for the intervening nucleic acid molecule to have the nucleic acid sequence of the foot and mouth disease virus 2A protease, or a functional fragment thereof.

Still further features of the invention provide for the polypeptide having necrosis inducing activity to be selected from, but not limited to, the group comprising thymidine kinase (TK), perforin, granzyme, caspase, RIP proteins 1&3, adenovirus penton fibre, NSP4, streptolysin O, anthrolysin, PB-F2, and functional fragments thereof. The NSP4 protein may be from rotavirus. Alternatively, the cell death-inducing protein may be selected from the group comprising, but not limited to, Anthrolysin O; human or mouse perforin, including wild type and mutant forms (such as, but not limited to, SEQ ID NO 7); Adenovirus penton fibre; Granzyme A or B; Caspase 1; Streptolysin O; the influenza A virus protein PB-F2 and Cholera toxin.

The invention further provides for a nucleic acid vaccine comprising for use in the method of the invention, wherein:
- the first nucleic acid sequence comprises a nucleic acid sequence encoding a polypeptide having cell death inducing activity; and
- the second nucleic acid sequence comprises a nucleic acid sequence encoding an immunogenic polypeptide.

In another embodiment of the invention, the nucleic acid vaccine further comprises:
- a first nucleic acid sequence encoding a polypeptide having necrosis inducing activity; and
- a second nucleic acid sequence encoding an immunogenic polypeptide;
- wherein the first nucleic acid sequence and the second nucleic acid sequence are operably in frame for expression of the polypeptide having necrosis inducing activity and the immunogenic peptide as a fusion protein.

In another embodiment of the invention, the nucleic acid vaccine further comprises:
- a first nucleic acid sequence having a first nucleic acid sequence encoding a polypeptide having necrosis inducing activity;
- a second nucleic acid sequence having a second nucleic acid sequence encoding an immunogenic polypeptide; and
- an intervening nucleic acid sequence between the first and second nucleic acid molecules, having a nucleic acid sequence encoding a protease.

Due to the degeneracy of the DNA code, it will be well understood to one of ordinary skill in the art that substitution of nucleotides may be made without changing the amino acid sequence of the encoded polypeptide. Therefore, the invention includes any nucleic acid sequence for a polypeptide having necrosis inducing activity comprising a nucleic acid sequence encoding a toxic protein (which is capable of inducing cell necrosis) and a nucleic acid sequence encoding an immunogenic polypeptide according to the invention. Moreover, it is understood in the art that for a given protein's amino acid sequence, substitution of certain amino acids in the sequence can be made without significant effect on the function of the peptide. Such substitutions are known in the art as "conservative substitutions." The invention encompasses a nucleic acid sequence according to the invention comprising a first nucleic acid sequence encoding a polypeptide having necrosis inducing activity and a second nucleic acid sequence encoding an immunogenic polypeptide according to the invention that contains conservative substitutions, wherein the function of the cell necrosis inducing polypeptide and immunogenic polypeptide according to the invention is not altered.

The invention extends to a fusion protein comprising:
- a polypeptide having cell necrosis inducing activity; and
- an immunogenic polypeptide.

The invention also provides a fusion protein comprising:
a polypeptide having cell necrosis inducing activity;
an immunogenic polypeptide and
a protease.

Further features of the invention provide for the protease to be the foot and mouth disease virus 2A protease, or a functional fragment thereof.

The invention also provides for a recombinant virus vaccine comprising
the nucleic acid vaccine according to the invention; and
regulatory expression elements operably linked to the nucleic acid sequences of the nucleic acid vaccine for expression of the polypeptide having cell necrosis inducing activity and the immunogenic polypeptide in a host cell.

Further features of the invention provide for the recombinant virus vaccine to be selected from, but not limited to, the group comprising a replication-competent vector and a replication-defective vector, wherein the vector does not induce cell necrosis.

The recombinant virus vaccine may be selected from the group including a baculovirus vector; a replication-defective virus including a virus selected from the group comprising a replication-defective virus derived from human and animal adenoviruses, lentivirus, recVV, MVA, AAV, PAV; a replication-competent virus including a virus selected from the group comprising replication competent viruses derived from human and animal adenoviruses, lentivirus, recVV, MVA, AAV, PAV; and a liposome/lipoplex and an virosome generated from influenza virus or similar viruses.

The invention also provides for an expression vector comprising
the nucleic acid vaccine according to the invention; and
regulatory expression elements operably linked to the nucleic acid sequences of the nucleic acid vaccine for expression of the polypeptide having cell necrosis inducing activity and the immunogenic polypeptide in a host cell.

Further features of the invention provide for the expression vector to be selected from, but not limited to, the group comprising a replication-competent vector and a replication-defective vector, wherein the vector does not induce cell death.

The expression vector may be selected from the group including a baculovirus vector; a replication-defective virus including a virus selected from the group comprising a replication-defective virus derived from human and animal adenoviruses, lentivirus, recVV, MVA, AAV, PAV; a replication-competent virus including a virus selected from the group comprising replication viruses derived from human and animal adenoviruses, lentivirus, recVV, MVA, AAV, PAV; and a liposome/lipoplex and a virosome generated from influenza virus or similar viruses.

The invention encompasses an expression vector of the invention containing DNA that is at least 40% identical; at least 45%; at least 50%; at least 55%; at least 60%; at least 65%; at least 70%; at least 75%; at least 80%; at least 85%; at least 90%; at least 95%; or at least 97% identical; to either SEQ ID NO: 1 or SEQ ID NO: 2. Most preferably, the expression vector will be at least 99% identical to of either SEQ ID NO: 1 or SEQ ID NO: 2.

The invention yet further provides for a pro-inflammatory cellular vaccine comprising a cell; and
the nucleic acid vaccine of the invention;
the fusion protein according of the invention;
the recombinant virus vaccine of the invention; or
the expression vector of the invention;

The invention also provides for an immunogenic composition comprising:
a nucleic acid sequence encoding an immunogenic polypeptide;
a nucleic acid sequence encoding at least one Human Leukocyte Antigen (HLA);
the nucleic acid vaccine according to the invention;
the fusion protein according to the invention;
the recombinant virus vaccine according to the invention;
the expression vector according to the invention; and/or
the pro-inflammatory cellular vaccine according to the invention.

The invention further provides a method of inducing or enhancing an antigen-specific immune response to an antigen in a subject, the method including the step of exposing the subject to the immunogenic composition according to the invention.

The invention also provides for a method of increasing CD4+ T cell levels and/or activity and/or CD8+ T cell levels and/or activity in a subject, the method including the step of exposing the subject to the immunogenic composition according to the invention.

The invention further provides for a method of vaccinating a subject with an immunogen, the method including the step of exposing the subject to the immunogenic composition according to the invention.

The invention also provides for a method of generating a dendritic cell (DC) immune response profile in a subject, the method including the step of exposing the subject to the immunogenic composition according to the invention.

The invention further provides for a method of generating a CD4+ T cell and/or CD8+ T cell immune response profile in a subject, the method including the step of exposing the subject to the immunogenic composition according to the invention.

The invention also provides for a method of inducing an antibody immune response in a subject, the method including the step of exposing the subject to the immunogenic composition according to the invention.

Further features of the invention provide for the step of exposing the subject to the immunogenic composition according to the invention to comprise the following steps:
exposing the subject to a vaccine nucleic acid according to the invention;
exposing the subject to a recombinant virus vaccine according to the invention; and
exposing the subject to a replication-competent or replication-defective recombinant virus vaccine according to the invention.

Still further features of the invention provide for a method of preparing an immunogenic composition, the method including the steps of:
contacting a host cell with the nucleic acid vaccine according to the invention;
expressing the immunogenic polypeptide; and
inducing necrosis in the host cell.

The invention extends to an immunogenic composition prepared according to the method of the invention.

The invention also provides for a method of presenting an immunogenic polypeptide to a subject, the method including the steps of:
contacting a host cell with the nucleic acid vaccine according to the invention;
expressing the immunogenic polypeptide;
inducing necrosis in the host cell; and
exposing the subject to the host cell.

The invention further provides for a method of generating a cytotoxic T cell response against HIV in a subject, the method comprising:
  administrating to the subject a necrotic allogeneic cell or a necrotic autologous cell;
  wherein the necrotic cell comprises a HIV antigen and human leukocyte antigens (HLA);
  wherein the necrotic cell does not comprise live HIV;
  wherein the necrotic cell undergoes necrosis in the subject;
  wherein the necrosis releases viral antigen from the dead or dying necrotic cell;
  wherein the host dendritic cells or other APC phagocytose the viral antigen;
  wherein the host dendritic cells or other APC process and present the viral antigen to naïve $CD4^+$ T cells via the class II pathway to induce T helper cells;
  wherein the host dendritic cells or other APC process and present the viral antigen to naïve $CD8^+$ T cells via the class I cross presentation pathway to induce cytotoxic T lymphocytes; and
  wherein the method generates antibodies and/or cell mediated immunity against HIV antigen and HLA.

The HLA may include a plurality of HLA proteins and/or other cell proteins that are in the HIV lipid envelope.

The invention also provides for a pro-inflammatory cellular vaccine comprising an allogeneic and/or autologous cell comprising HIV antigen and human leukocyte antigen (HLA) and wherein the allogeneic and/or autologous cell does not comprise live HIV.

The invention further provides for a method of generating a cytotoxic T cell response against HCV in a subject, the method comprising:
  administering to the subject a necrotic allogeneic cell or a necrotic autologous cell;
  wherein the necrotic cell comprises HCV antigen;
  wherein the necrotic cell does not comprise live HCV;
  wherein the necrotic cell undergoes necrosis in the subject;
  wherein the necrosis releases the immunogen from the dead or dying necrotic cell;
  wherein host dendritic cells or other APC phagocytose the viral antigen;
  wherein the host dendritic cells or other APC process and present the viral antigen to naïve $CD4^+$ T cells via the class II pathway to induce CD4+ T helper cells; and
  wherein the host dendritic cells or other APC process and present the viral antigen to naïve $CD8^+$ T cells via the class I cross presentation pathway to induce cytotoxic T lymphocytes.

The invention also provides for a pro-inflammatory cellular vaccine comprising an allogeneic and/or autologous cell comprising HCV antigen wherein the cell does not comprise live HCV.

The invention further provides for an isolated antibody capable of binding to the immunogen as produced by one or more of the following:
  the immunogenic composition of the invention;
  the nucleic acid sequence encoding an immunogenic polypeptide of the invention;
  the nucleic acid vaccine of the invention;
  the fusion protein of the invention;
  the recombinant virus vaccine of the invention; or
  the expression vector of the invention.

The invention further provides a method of prophylactically or therapeutically treating an infection in a patient, said method comprising administering to the patient an effective amount of the immunogenic composition according to the invention. Preferably, when the immunogenic composition comprises cells, the dose is selected from the list comprising: between $1 \times 10^2$ to $1 \times 10^9$ cells per dose; between $1 \times 10^3$ to $1 \times 10^8$ cells per dose; between $1 \times 10^4$ to $1 \times 10^7$ cells per dose; and between $1 \times 10^5$ to $1 \times 10^6$ cells per dose. Preferably, when the immunogenic composition comprises a nucleic acid vaccine, fusion protein, recombinant virus vaccine or expression vector, the dose of nucleic acid vaccine, fusion protein, recombinant virus vaccine or expression vector is selected from the list comprising: between 10 µg to 100 mg per dose; between 100 µg to 10 mg per dose; between 300 µg to 5 mg per dose; between 300 µg to 3 mg per dose; and between 500 µg to 1 mg per dose. Preferably the immunogenic composition is administered intramuscularly, intradermally or intravenously. Preferably, the immunogenic composition is administered on a routine selected from the list comprising; three times daily, twice daily, twice weekly, once monthly, twice monthly, every two months, every three months, every sixth months, yearly twice yearly every two years and every five years.

The invention further provides a use of the immunogenic composition of the invention in the manufacture of a medicament for the prophylactically or therapeutically treatment of an infection in a patient.

The invention further provides a pharmaceutical composition comprising the immunogenic composition of the invention, together with an acceptable diluent or carrier.

The invention further provides a therapeutic vaccine comprising the immunogenic composition of the invention.

The invention further provides a prophylactic vaccine comprising the immunogenic composition of the invention.

The invention further provides a dosage form comprising the immunogenic composition of the invention.

The invention further provides a kit comprising the dosage form of the invention sealed in a vial or container. Preferably, the sealed vial or container is labelled with instructions that the kit is used for the prophylactic or therapeutic treatment of an infection in a patient.

The term "immunogenic composition" as used herein comprises the substances of the present invention and optionally one or more pharmaceutically acceptable carriers. The immunogenic compositions can be conveniently administered by any of the routes conventionally used for vaccine administration, for instance, parenterally or by inhalation. The substances may be administered in conventional dosage forms prepared by combining the immunogenic composition with standard pharmaceutical carriers according to conventional procedures. The carrier(s) must be "acceptable" in the sense of being compatible with the other ingredients of the formulation and not deleterious to the recipient thereof. The dosage regimen will be determined by the attending physician and other clinical factors; preferably in accordance with any one of the methods described above. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. Dosage can be varied and delivered as one or multiple doses. The DNA can be delivered as naked DNA or complexed with lipids, liposomes, lipoplexes, virosomes, immunoliposomes, or other commercial or non-commercially available compounds.

The dose administered to the patient, in the context of the present invention, should be sufficient to induce an immune response as detected by conventional assays measuring CD4+ and/or CD8+ response, conventional assays measuring antibody response, and/or effect a beneficial therapeutic response in a subject over time such as, but not limited to, a decrease in viral load or a decrease in other viral associated symptoms.

Some of the vaccines of the invention described above may have application as therapeutic vaccines. That is, some of the vaccines of the invention may be applied as injected therapy for administering to patients already infected with HIV or HCV. In such instances, the use of some of the vaccines of the invention may have application in substantially increasing the immune response to HIV or HCV, and substantially decreasing disease progression.

Some of the vaccine of the invention described above may have application as prophylactic vaccines. That is, some of the vaccines of the invention may be applied as preventative therapy for administering to patients not already infected with HIV or HCV. In such instances, the use of some of the vaccines of the invention may have application in substantially generating an immune response to HIV or HCV in a previously uninfected subject.

The vaccines of the invention described herein may be delivered by various routes of delivery eg. Intranasal, oral, subcutaneous, intradermal, intramuscular, intrathecal, pulmonary, intrarectal, topical, intravaginal, by scarification, intralesionally, intrabuccal, particle bombardment, nanoparticles, ID pulse followed by IN sublingual boost or any other combination.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 2 shows a table of the proportion of apoptotic and necrotic cells within the 'dead cell' population gate. Apoptotic cells were defined as Annexin V+ PI−, secondary necrotic cells were defined as Annexin V+PI+. A third dead cell population that was Annexin V− PI+ was identified as cells that had undergone non-apoptotic cell death, likely primary necrosis.

FIG. 9 shows a plasmid map of the pVAX luciferase-NSP4 plasmid prepared for the bicistronic expression of luciferase and NSP4, according to Example 2.

FIG. 10 shows a plasmid map of the pVAX luciferase-PRF plasmid prepared for the bicistronic expression of luciferase and PRF, according to Example 2.

FIG. 19 shows the frequency of murine CD44$^+$ memory, CD8$^+$ T cells stimulated ex vivo with immunodominant gag peptides after vaccination with pVAXgag, pVAXgag +NSP4 or pVAXgag +PRF as determined by multifunctional cytokine staining followed by flow cytometry, according to Example 4.

FIG. 20 shows the frequency of murine CD44$^+$ memory, CD8$^-$ T cells stimulated ex vivo with immunodominant gag peptides after vaccination with pVAXgag, pVAXgag +NSP4 or pVAXgag +PRF as determined by multifunctional cytokine staining followed by flow cytometry, according to Example 4.

FIG. 39 shows the design of the trial according to Example 6.

FIG. 45 shows a table of the raw HCV viral load data for patients vaccinated in the clinical trial according to Example 6.

FIG. 46 shows a table of the HCV viral load as a percentage of the baseline level for the patients vaccinated in the clinical trial according to Example 6.

Figure 1:
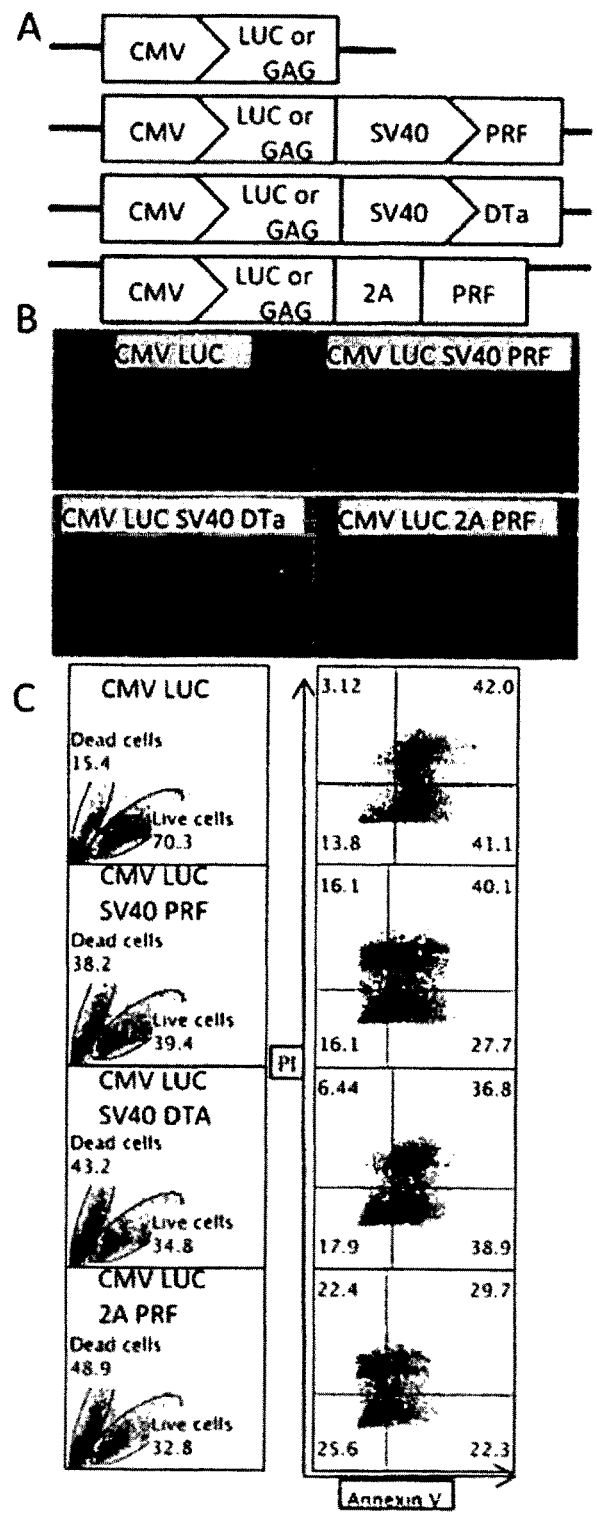
FIG. 1 shows a schematic of the design of DNA vaccines encoding PRF or DTa that induce cell death in vitro according to Example 1. (A) Schematic diagrams of the bicistronic DNA vaccine constructs. All vaccines use the pVAX backbone with a gene encoding an antigen (HIV-1 GAG or firefly luciferase (LUC)) under the control of the CMV promoter and PRF or DTa under the control of the SV40 promoter. An additional construct encodes the antigen and PRF as a polyprotein controlled by the CMV promoter that self-cleaves at the FMDV 2A protease sequence. (B) Phase microscopy images (100×) reveal rounded, detached HEK293T cells at 48 hours post transfection with DNA vaccines encoding DTa or PRF. (C) Flow cytometry to identify dead cells, and Annexin V and PI staining to identify apoptosis (Annexin V+) and necrosis (Annexin V+ PI+) 48 hours post transfection.

SEQ ID NO: 1 is the DNA sequence of pVAX luciferase-TK plasmid.

SEQ ID NO: 2 is the DNA sequence of pVAX luciferase-NSP4.

SEQ ID NO: 3 is the DNA sequence of thymidine kinase (TK).

SEQ ID NO: 4 is the DNA sequence of NSP4.

SEQ ID NO: 5 is the DNA sequence of luciferase.

SEQ ID NO: 6 is the RNA sequence of NS3.

SEQ ID NO: 7 is the DNA sequence of mouse mutant perforin (PRF).

SEQ ID NO: 8 is the amino acid sequence of the 2A protease.

SEQ ID NO: 9 is the DNA sequence of the 2A protease.

Throughout this specification, unless the context requires otherwise, the word "comprise" or variations such as "comprises" or "comprising", will be understood to imply the inclusion of a stated integer or group of integers but not the exclusion of any other integer or group of integers.

DESCRIPTION OF EMBODIMENTS

Introduction
DNA Vaccines

DNA vaccines induce cell-mediated (CMI) and humoral immune responses, and result in antigen expression and processing that mimics viral protein production. DNA vaccines also have practical advantages, as they are highly stable and more easily and rapidly manufactured than protein or recombinant-virus vaccines.

Attempts to improve DNA vaccine immunogenicity have largely focused on the co-expression of immunostimulatory proteins such as cytokines, co-stimulatory molecules CD80 and CD86, and Toll-like receptor ligands. Previously, the improvement of immune responses to vaccines has involved targeting antigen directly to dendritic cells (DC). Protein vaccines have been conjugated to antibody that binds DC surface receptors such as DEC205 and Clec9A. This strategy increased DC antigen presentation and T cell responses following protein vaccination, which has traditionally induced mainly humoral responses. However, such approaches require additional adjuvants such as Poly I:C to ensure DC activation.

In Example 1, the inventors have developed a DNA vaccination strategy for DC targeting of antigen and for providing adjuvant signals for activation via induction of necrosis. Necrosis provides danger signals to the immune system via the release of intracellular factors that act as 'damage-associated molecular-patterns', (DAMPs). DAMPs such as uric acid and HMGB-1 are capable of signaling to DC via diverse receptors. More recently the receptor Clec9A and its ligand F-actin have been identified as a mechanism by which DC sense necrosis and target antigen for cross-presentation. Furthermore, necrosis also leads to NLRP3 inflammasome activation within cells and release of pro-inflammatory cytokines. In addition, tissue damage resulting in release of double-stranded DNA into the extracellular space has been identified as one of the underlying mechanisms of Alum adjuvants. The DNA vaccine described herein encodes an antigen and a cytolytic gene that results in targeted necrosis of antigen-positive cells. As such, this DNA vaccine substantially mimics the effect of a lytic virus, and lytic viruses such as vaccinia are known to be highly immunogenic.

Suicide genes, that generally induce apoptosis of target cells, have been proposed for use as cancer therapies. The inventors have surprisingly found that suicide genes or cytolytic genes which induce necrosis may be used as adjuvants for prophylactic vaccines.

The inventors believe that for optimum protection, vaccines against HIV and HCV require cell mediated immunity (CMI) to be induced in addition to neutralising antibody (NAb) or antibody with other characteristics eg. ADCC activity. CMI is most readily generated by natural infection, live- or recombinant-virus vaccines, or DNA vaccines, resulting in expression of the immunogens.

Innate Immunity Activates Adaptive Immune Responses

Innate immunity is activated by pathogen associated molecular patterns (PAMPs) or DAMPs as a prelude to adaptive immune responses. The most common PAMPs are LPS and dsRNA which bind to recognised pattern recognition receptors (PRR), including toll-like receptors (TLRs) but these PAMPs are not expressed after vaccination with naked DNA or recombinant, replication-defective vaccine vectors eg. RecAd. Consequently, although these vaccines generate viral antigens for uptake by DC, this will not result in mature DC because an additional stimulation signal or DAMP is necessary to "licence" mature, antigen-loaded DC with the capacity to migrate to draining lymph nodes and activate naïve T cells. Necrotic cells in particular are a rich source of DAMPs which include the heat shock proteins (HSP), uric acid, high mobility group box 1 protein (HMGB1) and extracellular ATP, chromatin, nucleosomes, DNA, galectins, thioredoxin, S100 proteins, cathelicidins, and defensins, and act as natural adjuvants. Apoptotic cells, although not generally inflammatory in nature, may develop secondary necrosis. HSP70 and HMGB1 have been used successfully to increase the immunogenicity of viral proteins. One study used a mixture of plasmids which encoded HIV gag and HMGB1, whereas the results described herein used DNA vaccines which encode both proteins in a single vector.

Cell Death and Priming Immune Responses

B lymphocytes express immunoglobulin and class II MHC molecules on their cell surface and are able to produce antibody which recognises the same antigen as that of their immunoglobulin receptor, the B cell receptor. B cells can also act as an APC. The antigen is recognized by the immunoglobulin receptor, phagocytosed, processed and the epitopes presented to a helper T cell in a MHC class II-restricted manner. This results in activation of the T cell and in the production of cytokines which in turn induce the B cell to divide and secrete specific antibodies. In this context, the B cell acts as an APC that can phagocytose antigen, analogous to a Class II APC.

However, in a similar manner to that described above for DC, additional stimuli, provided by PAMPs or DAMPS, are required to activate the B cell. Thus, many antigens are dependent on T cell help in order to elicit an effective antibody response.

Although $CD8^+$ T cells are recognised as the effector cells that eliminate virus-infected cells or secrete cytokines that inhibit virus replication, there is also a need for $CD4^+$ T cell help to prime and expand $CD8^+$ T cells. By mimicking virus-related cell death the invention described herein facilitates the cross presentation of the immunogen and the induction of CD8 T cell responses and also facilitates the induction of CD4 T cell responses by uptake of exogenous immunogen that results from cell lysis.

Dendritic cells (DC) are the major APC able to prime naïve T cells, the primary aim of vaccination. DC phagocytose viral antigens (released from infected or vaccine-targeted necrotic cells), process and present these to naïve $CD4^+$ T cells via the class II pathway (to generate Th) and to naïve $CD8^+$ T cells via the class I pathway (cross presentation) to generate CTL. Cross presentation is proposed to be required for CD8 T cell immunity to viruses, because immunity would otherwise only occur if the virus or a vaccine infected DC to express antigen. If vaccine delivery vehicles are to be successful, they must target DC or otherwise direct the immunogen to DC. It is possible, even likely, that cross presentation is the major mechanism to induce cell mediated immune responses.

Dead cells are highly immunogenic due to release of DAMPs, pro-inflammatory "danger signals". The uptake of viral antigen-positive dead or dying cells by DC and other APC represents a fundamental mechanism to elicit immunity against pathogens or the payload of vaccine delivery vehicles that do not intrinsically infect DC.

Suicide Gene Therapy

Suicide gene therapy has been used to treat various tumours by inducing cell death. The prototype suicide gene is thymidine kinase (TK), usually derived from herpes simplex virus (HSV). In the first step, the gene is delivered for protein expression in the target cell. The second step is to administer a prodrug, ganciclovir (GCV), which is activated by the expressed protein. The HSV TK gene, used in combination with GCV, is one of several approaches to kill cells and can induce necrosis, depending on cell type. GCV, commonly used to treat patients with herpesvirus infections, is a nucleoside analog which is converted to the monophosphate form by the HSV TK, then into the triphosphate form by cellular kinases, prior to incorporation into DNA. This results in DNA chain termination and cell death. Non apoptotic cell death (necrosis) results in expression of HSP70, and DC express receptors for HSP. Thus TK/GCV-induced cell death is likely to result in cross presentation of a protein immunogen in DC and phagocytosis by macrophages. The immune response to tumour cells was more effective after necrosis, characterized by increased levels of HSP70, than after apoptosis, although apoptotic cells also induced anti-tumour immunity. In that study, apoptosis or necrosis was induced in different cell lines by TK/GCV treatment and immunogenicity was increased after co-transfection of the tumour cells with HSP70 cDNA.

Importantly, work in this field has been limited to the use of suicide gene therapy in treating cancers, for the direct destruction of the cancer cell. The invention relates to methods of duplicating the effect of live attenuated viruses which result in the production of endogenous immunogen and thereby during expression of the viral antigen the cell will lyse to result in exogenous protein that will be phagocytosed by antigen presenting cells (including dendritic cells), which will then cross present the phagocytosed antigen.

Other prodrug/activator combinations can be used to convert non-toxic prodrugs into toxic metabolites eg. cytosine deaminase activated by 5-fluorocytosine and purine nucleoside phosphorylase activated by fludarabine. More recently, the use of a suicide protein which is directly cytotoxic and does not require activation was reported. In the study, a protein immunogen and the cytotoxic protein M from the infectious hematopoietic necrosis virus I (IHNV) were co-expressed from DNA after vaccination of fish. Protein M expression was controlled by an inducible promoter viz. the metallothionein promoter by the addition of zinc to the water in which fish were kept. This resulted in elimination of residual DNA after DNA vaccination, but not increased levels of protection against challenge with IHNV. Although these approaches are generally effective in vitro and may have some effect in vivo, they are dependent on the administration of an activation- or inducing-reagent, after vaccination. This adds a degree of complexity to the vaccination process and it is likely that a significant proportion of human vaccines will be non-compliant if this procedure was necessary for a human vaccine to be effective.

EXAMPLE 1

Materials and Methods

DNA Vaccines

All DNA vaccine constructs are based on the pVAX plasmid backbone (Invitrogen). Genes for Firefly luciferase2 (Promega) or codon optimised HIV-1 gag (clade B) were inserted downstream of the CMV promoter. An additional promoter, the SV40 promoter, and a poly-adenylation sequence were inserted into the pVAX backbone and all cytolytic/suicide gene candidates were inserted downstream of this second promoter. All DNA vaccines were purified using the Qiagen Endotoxin-free Mega kit.

Cell Culture

HEK293T cells (human embryonic kidney cell line) were grown in DMEM supplemented with 10% FCS and 1% Pen/Strep, and transfected with DNA using Fugene 6 reagent (Promega). Cell viability was determined by trypan blue staining. Cell death was tracked over time by luciferase assay using firefly luciferase as a reporter and D-Luciferin (Perkin Elmer) substrate. Markers of apoptosis and secondary necrosis were assayed by flow cytometry using Annexin-V (Invitrogen) and PI (BDBiosciences) staining.

Mice

All experiments were approved by the University of Adelaide and the Women’s and Children’s Health Network animal ethics committees. C57BL/6 mice from the University of Adelaide Laboratory Animal Services were maintained under specific-pathogen-free conditions and vaccinated at 6-8 weeks. All interventions were performed under Domitor/Ketamine anesthetic, injected i.p. The anesthetic was reversed with Antisedan i.p. Blood samples were obtained by retro-orbital bleed with haematocrit tubes. Live imaging was performed on isofluorane sedated animals using an IVIS live imager (PerkinElmer) after injection of D-luciferin K+ 3 mg/20 g mouse.

Immunization

C57BL/6 mice received a 50 L dose of DNA vaccine (50 g in saline) injected into the dermal layer of the ear (25 l/ear). Unless otherwise stated, mice received a total of 3 doses of vaccine at 4-week intervals, and peripheral blood samples were taken prior to each vaccination. At 10 days post-final vaccination, the mice were anesthetised and killed, and spleen, peripheral blood and draining lymph nodes collected.

ELISPOT

IFN ELISPOT was performed on red blood cell-depleted splenocytes that were re-stimulated with 2 µg/mL 15-mer, 11a.a overlapping gag peptide pools (NIH AIDS reagent bank #8117) or MHC I and II restricted immunodominant peptides (listed in the HIV molecular immunology database, http://www.hiv.lanl.gov/). Multiscreen-IP HTS plates (Millipore) were coated with anti-mouse IFN (clone AN18, MabTech) and secreted IFN was detected with anti-mouse IFN-biotin (clone R4-6A2, MabTech), streptavidin-AP (Sigma) and SigmaFast BCIP/NBT. Cells for the luciferase ELISPOT were re-stimulated with 2 µg/mL of the immunodominant peptide, LMYRFEEEL.

Flow Cytometry

Multi-colour intracellular cytokine staining was performed on splenocytes re-stimulated with immuno-dominant gag peptides for 12 hours in the presence of Brefeldin A. Staining was performed with BD FACS Cytofix/Cytoperm and BD anti-mouse antibodies (CD3-PercP-Cy5.5, CD8-APC-Cy7, CD44-APC, IL-2-FITC, IFN-Pecy7, TNF-PE, BDbiosciences). Dendritic cell staining was performed on cell suspensions obtained from the auricular draining lymph nodes using BD antibodies (CD8a-APC-Cy7, CD11c-PeCy7, CD80-APC, CD86-PE, MHCII-FITC, BDbiosciences). Cells were analysed on a BD FACS Canto and results analysed with FlowJo software.

ELISA

Corning 96 well EIA/RIA plates were coated with 500 ng/well recombinant luciferase (Promega). Serum samples were incubated for 2 hours at 37° C. and detected with anti-mouse IgG-HRP (GE healthcare) and SigmaFast OPD (Sigma).

EcoHIV Challenge

EcoHIV/NL4-3 challenge and qRT PCR monitoring were performed as described previously (Potash M J, et al. (2005) *Proc Natl Acad Sci USA* 102(10):3760-3765; Roshorm Y, et al. (2009) *Eur J Immunol* 39(7):1831-1840; Suhrbier A, et al. (2013) *PLoS One* In Press). Briefly, EcoHIV stocks were prepared by transfection of pEcoHIV into HEK293T cells. Purified virus supernatant (or conditioned media control) was administered to mice via i.p. injection at a concentration of 1.5 ug p24 (Zeptometrix p24 antigen ELISA). Seven days post EcoHIV challenge, mice were culled, and spleen, peritoneal exudate cells (PEC) and peripheral blood samples were collected. RNA was isolated using the Trizol method and used to generate cDNA (Qiagen Quantitect RT-PCR kit). 50 ng of cDNA was used as template for quantitative real-time PCR using the Quantifast Sybr Green kit (Qiagen) to determine levels of MLV mRNA (5'-GAGGTCGGGTG-GAAGTACCA-3' 5'-TGCA TCTTGGCCTTTTCCTT-3'). Results were normalised to RPL13a expression (5'-TAGGGCCAAACCCCGTTCTG-3' 5'-GCCGGTG-GAAGTTGGGTAGG-3') after validation of primer amplification efficiency, using the CT method of quantification.

Statistical Analysis

Data are presented as the mean+/−SEM. Data analysis and generation of graphs was performed using Graphpad Prism 5.0b and SAS Version 9.3. Nonparametric Kruskal-Wallis test was used in comparing the difference between the multiple vaccine groups (pVAX GAG Standard Vaccine, pVAX GAG DTa (A), pVAX GAG PRF (B) and pVAX GAG 2A PRF(C). If the global test showed significant difference between the groups then Wilcoxon tests were performed to compare the post-hoc difference between Standard Vaccine group vs. A, Standard Vaccine group vs. B and Standard Vaccine group vs. C separately.

Results

DTa and PRF Cause Cell Death In Vitro

DNA vaccines were constructed using the plasmid pVAX, (Invitrogen), which contains either a luciferase (LUC) reporter gene or the HIV-1 GAG gene under the control of the constitutive CMV promoter. To investigate the effect of cell death following DNA vaccination, bi-cistronic constructs were designed to also encode either (i) perforin (PRF), an endogenous mediator that disrupts cellular membranes and causes cell lysis, or (ii) Diphtheria Toxin subunit A (DTa), which inhibits protein synthesis and causes apoptosis. These genes were inserted under the control of the weaker SV40 promoter (FIG. 1A). The SV40 promoter resulted in 10-fold lower expression of luciferase compared to the CMV promoter, permitting lower levels of PRF or DTa expression relative to the antigen expressed from the CMV promoter. An additional construct encoded a LUC-PRF or GAG-PRF polyprotein under the control of the CMV promoter; the two proteins were separated by the FMDV 2A protease to enable autocleavage of the polyprotein. This latter construct allowed investigation of the effects of the cytolytic gene, PRF, when expressed at 10-fold higher levels from the CMV promoter.

The DNA vaccines were first tested for their ability to induce cell death in vitro. After transfection with the bi-cistronic plasmids, HEK293T cells showed visible signs of cell death 48 hours later, and cell death was confirmed by flow cytometry using Annexin V and propidium iodide (PI) staining (FIG. 1B-C). At 48 hours post transfection with CMV-LUC-SV40-PRF or CMV-LUC-SV40-DTa, a significant proportion of cells were shown to be dead as determined by forward and side scatter characteristics (38.2% and 43.2% respectively), compared to cells transfected with CMV-LUC DNA alone (15.4%). When PRF was encoded under the control of the stronger CMV promoter (CMV-LUC-2A-PRF) cell death was more rapid compared with CMV-LUC-SV40-PRF, with 48.9% of cells dead by 48 hours. As the transfection efficiency was generally ~70%, this indicates that a majority of the cells that expressed PRF or DTa were killed. Within these dead cell populations, the proportion of apoptotic (AnnexinV+ PI−) and necrotic (AnnexinV+ PI+) cells varied, as summarised in FIG. 2, reflecting the different mechanisms by which DTa and PRF induced cell death. Transfection with CMV-LUC-SV40-DTa resulted in cells that were primarily apoptotic or secondary necrotic, whereas CMV-LUC-SV40-PRF transfection resulted in a higher proportion of primary and secondary necrotic cells. Cells transfected with CMV-LUC-2A PRF showed the highest proportion of primary necrotic cells.

Live Imaging of Luciferase Allows Tracking of Antigen Expression after Intradermal Vaccination To investigate the effects of cell death after DNA vaccination in vivo, luciferase was used as a model antigen. This allowed live imaging of mice and tracking of antigen expression after vaccination. Female C57BL/6 mice were vaccinated with a single dose of 50 µg DNA via the intradermal (ID) route (ear pinnae dermis) and imaged periodically for luminescence. The inclusion of the PRF or DTa gene changed the kinetics of luciferase expression after vaccination (FIG. 3A-B). Mice that received CMV-LUC DNA demonstrated detectable luminescence to day 35 post-vaccination, although the level of luminescence dropped 100-fold over this period. In contrast, mice that received CMV-LUC-SV40-PRF DNA showed a more rapid decrease in luminescence, which was undetectable by day 35. The CMV-LUC-SV40-DTa and CMV-LUC-2A-PRF groups showed the most rapid decrease in luminescence, and no detectable luminescence was seen in these mice after day 14, indicating luciferase-positive cell clearance (FIG. 3B). In addition, the CMV-LUC-SV40-DTa and CMV-LUC-2A-PRF vaccinated groups demonstrated a 10-fold lower luminescence from day 1 after vaccination, indicating that there was reduced antigen expression in the dermis even at the earliest time-point. Thus the live imaging demonstrated that co-expression of DTa or PRF with luciferase from the DNA vaccine facilitated removal of luciferase-positive cells. The timing of cell death differed between DTa and PRF, and also between different levels of PRF expression controlled by the CMV or SV40 promoters. This indicates that the intrinsic properties of DTa and PRF, as well as the overall level of expression controlled by the promoter, influence the timing of cell death.

All mice that received the ID vaccination showed some irritation (redness and swelling) around the site of injection, however this was observed even for mice that received an injection of saline, and rapidly subsided by days 2-3 post vaccination. No tissue damage was observed macroscopically, or microscopically by histological analysis in any vaccinated group. Thus co-expression of DTa or PRF led to specific killing of luciferase-positive cells without excessive inflammation or tissue damage.

The Luciferase-Specific Immune Response Following Intradermal DNA Vaccination

To examine the immune response to luciferase, vaccinated mice received booster vaccinations of 50 µg DNA at day 35 (at a point when luminescence expression was 100-fold lower in the CMV-LUC control mice (FIG. 3B)). To assess the humoral immune response, serum samples were examined by ELISA to detect luciferase-specific IgG. Mice vaccinated with CMV-LUC, CMV-LUC-SV40-PRF or CMV-LUC-2A-PRF all showed end-point titers of anti-luciferase IgG 1/10,000 (FIG. 3C). Thus the inclusion of PRF in the vaccine did not significantly enhance the luciferase-specific antibody response. Interestingly, CMV-LUC-SV40-DTa vaccination induced lower levels of luciferase-specific IgG (approximately 100-fold) compared to the CMV-LUC control, suggesting that, rather than enhancing immunity, it had an inhibitory effect on the immune response, probably due to a reduction in antigen levels caused by the ability of DTa to inhibit de novo protein synthesis.

An IFN ELISPOT was performed, using a single immunodominant luciferase peptide to restimulate splenocytes (FIG. 3D). The ELISPOT assay revealed low-level IFN responses to this peptide. CMV-LUC-SV40-PRF vaccination showed a clear trend towards an increased response to this immunodominant peptide compared to CMV-LUC, while CMV-LUC-SV40-DTa decreased the response.

PRF Enhances the T Cell Mediated Immune Responses to HIV-1 GAG DNA Vaccines

To investigate the effect of PRF and DTa on the immune response to a viral antigen that contains multiple T cell epitopes, the luciferase reporter gene was replaced with a codon-optimised Clade B HIV-1 GAG gene. Mice received 3 doses of 50 µg CMV-GAG, CMV-GAG-SV40-PRF, CMV-GAG-SV40-DTA or CMV-GAG-2A-PRF DNA as noted above, and the immune responses were assayed 10 days post final vaccination. IFN ELISPOTs were performed using four overlapping peptide pools (30 15-mer peptides per pool) representing the complete GAG sequence, and a final pool containing only immunodominant peptides (which are otherwise present in pools 2 and 3). Mice vaccinated with CMV-GAG DNA showed responses ranging from 50-1200 mean SFU to all peptide pools (FIG. 4A-D). Mice vaccinated with CMV-GAG-SV40-PRF DNA showed a similar range of responses to pools 1-3 in control CMV-GAG mice, but presented a 2.5-fold higher response to peptide pool 4, compared to CMV-GAG mice (mean SFU 155 vs. 62, p=0.03) (FIG. 4D). As this pool contains none of the immunodominant GAG peptides, this represents a broadening of the immune response to non-dominant epitopes. In contrast, the CMV-GAG-SV40-DTa DNA vaccinated mice showed 5-fold lower IFN responses to peptide pool 3 (mean SFU 142 vs. 696, p=0.003) and to the immunodominant peptides in pool 5 (mean SFU 272 vs. 1270, p=0.001), compared to CMV-GAG mice (FIGS. 4C and E). These results are consistent with the results from CMV-LUC-SV40-DTa vaccination shown in FIG. 3 and confirm that co-expression of DTa with an antigen actually reduces the subsequent immune response. Surprisingly, mice vaccinated with the CMV-GAG-2A-PRF DNA vaccine showed no significant changes in IFN responses compared to mice vaccinated with CMV-GAG DNA.

Figure 5:
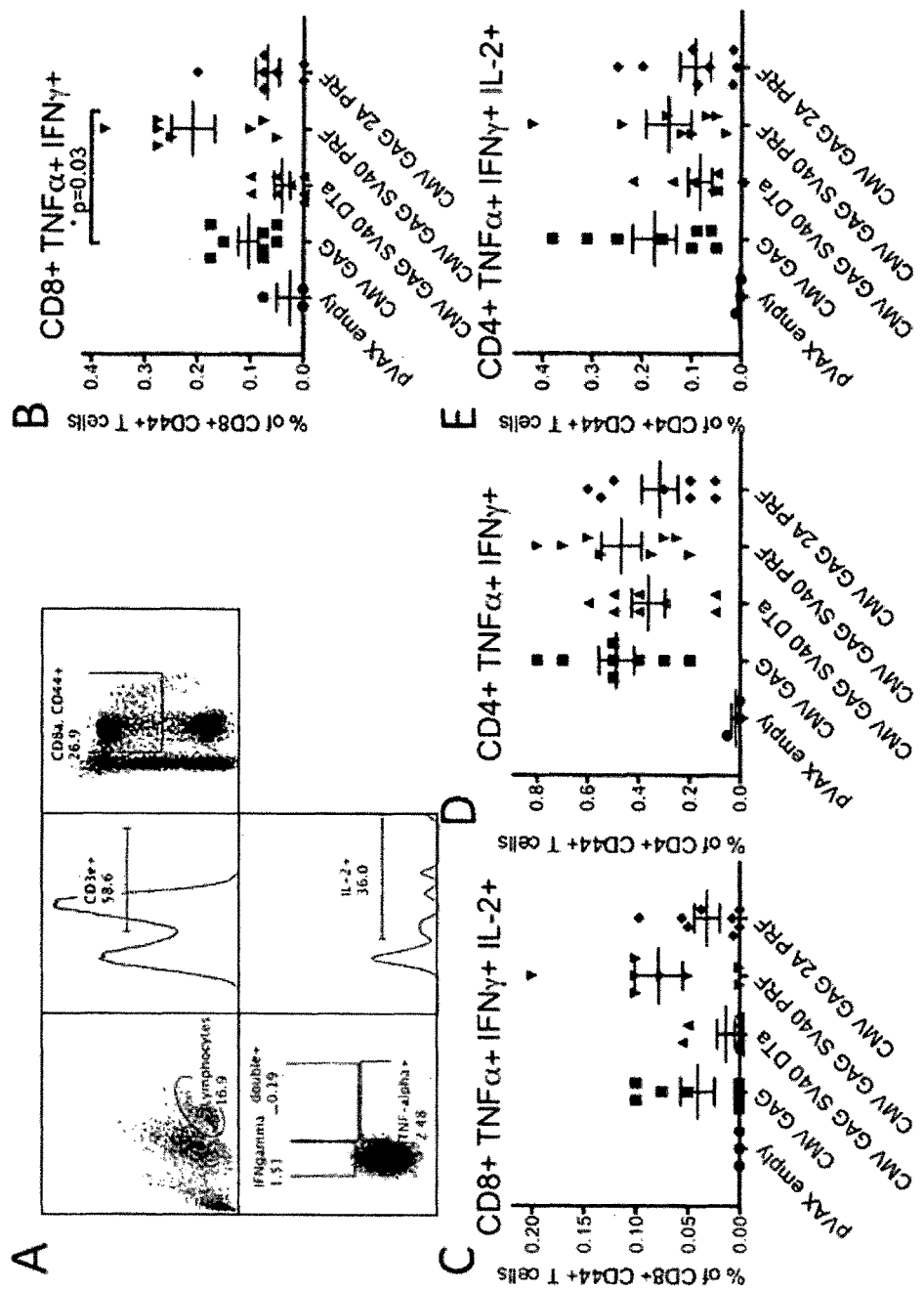
FIG. 5 shows multifunctional T cells detected by flow cytometry, according to Example 1. Intracellular cytokine staining for GAG-specific T cell responses after DNA vaccination, as described in the legend for FIG. 4. Splenocytes were re-stimulated for 12 hours with the immunodominant GAG peptide pool in the presence of Brefeldin A. (A) The gating strategy to identify IFN, TNF and IL-2 positive CD4 and CD8 CD44+ T cells. (B) The percentage of IFN and TNF-secreting CD8 T cells and (C) the percentage of IFN, TNF and IL-2-secreting CD8 T cells in response to GAG peptide stimulation. (D) Percentage of CD4 T cells secreting IFN and TNF, and (E) IFN, TNF and IL-2 in response to GAG peptides. Vaccinations were performed on groups of 8 female C57BL/6 mice. Graphs show mean percentage of cytokine secreting cells (+/−SEM).

Intracellular cytokine staining demonstrated that individual CD4 and CD8 T cells responded to vaccination by producing IFN, TNF and IL-2 (FIG. 5). Mice vaccinated with CMV-GAG-SV40-PRF DNA showed 2-fold higher levels of TNF and IFN-secreting CD8 T cells, compared to mice vaccinated with CMV-GAG DNA (mean percentage 0.21 vs. 0.1, p=0.03) (FIG. 5B). There was a trend showing an increase in rare, multifunctional CD8 T cells that secreted TNF, IFN and IL-2 simultaneously (mean percentage 0.078 vs. 0.04) in mice vaccinated with CMV-GAG-SV40-PRF when compared to CMV-GAG (FIG. 5C). All vaccinated groups (except mock-vaccinated) produced CD4 T cells that secreted multiple cytokines in response to GAG immunodominant peptides with no differences between groups (FIG. 5 D-E). Similarly, the CMV-GAG-2A-PRF DNA vaccine induced no significant changes in CD8 and/or CD4 T cell cytokine production compared to CMV-GAG DNA.

Thus, only PRF increased the immune response to the GAG peptide pools, and only when it was expressed from the weaker SV40 promoter (CMV-GAG-SV40-PRF). An increased level of expression of PRF from the CMV promoter (CMV-GAG-2A-PRF) had no effect on the immune response, and CMV-GAG-SV40-DTA DNA actively decreased the immune response, when compared to the control CMV-GAG DNA. Therefore more rapid killing of GAG antigen-positive cells over 7-14 days did not improve immune responses compared to slower killing over 28-35 days.

Figure 6:
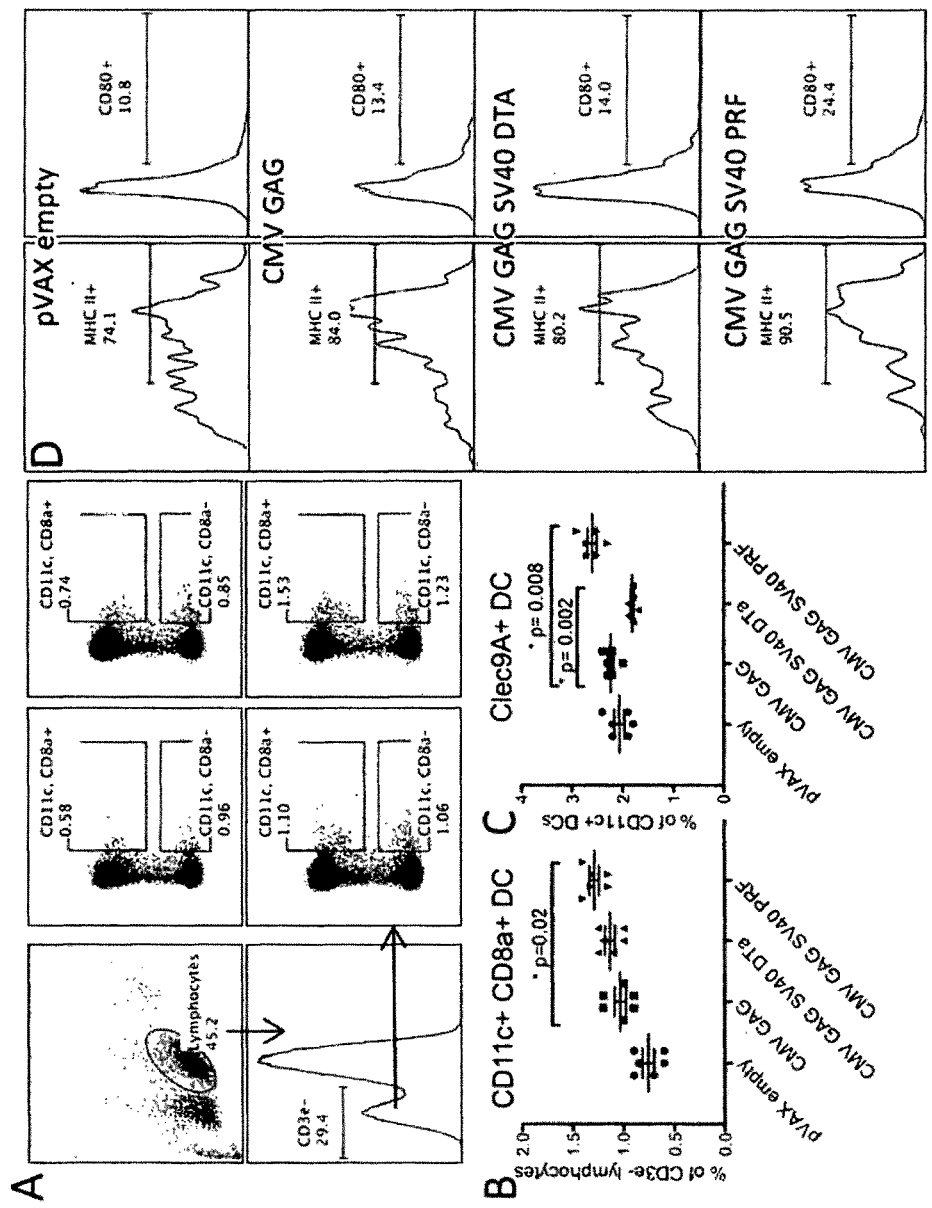
FIG. 6 shows detection of activated dendritic cells. Dendritic cells in the draining lymph node are activated after a single 50 μg DNA vaccination, according to Example 1. Auricular lymph nodes were harvested on days 3, 7, 10 and 14 post ID vaccination. (A) The gating strategy used to identify CD11c+ CD8a+ Clec9A+/− activated DC, showing representative plots from each group. pVAX empty and CMV-GAG upper middle and right panels, SV40-DTa and SV40-PRF lower middle and right panels. (B) Percentage of CD11c+ CD8a+ DC in the draining lymph node on day 14 post vaccination. (C) Percentage of Clec9A+ DC in the draining lymph nodes. (D) Histogram plots of the activation status of CD11c+ CD8+ DC as measured by MHCII and CD80 expression. DNA vaccinations were performed on groups of 4 female C57BL/6 mice. Graphs show mean percentage of cells (+/−SEM).

PRF Increases the Frequency of Cross-Presenting CD8a+ and Necrosis-Sensing Clec9A+ DC The data presented above show that expression of the cytolytic protein PRF and the apoptotic protein DTa resulted in opposite effects on the immune response to GAG. To determine whether PRF and DTa-induced cell death resulted in dendritic cell (DC) activation, the auricular draining lymph nodes were collected at different time points post vaccination. DC subpopulations were identified as CD3e−, CD11c+, and CD8a+/− or Clec9A+/− (FIG. 6). Mice vaccinated with CMV-GAG, CMV-GAG-SV40-PRF or CMV-GAG-SV40-DTa showed an increase in the frequency of CD11c+ DC in the lymph node and also in the expression of markers of DC activation, compared with the control group vaccinated with pVAX only. At day 14 post vaccination, a significant increase in the frequency of cross-presenting CD11c+ CD8a+ DCs was detected in the draining lymph node of mice vaccinated with CMV-GAG-SV40-PRF compared to mice vaccinated with CMV-GAG (mean percentage 1.3 vs. 1.0, p=0.02) (FIG. 6B).

Importantly, at this time-point there was also an increase in the frequency of Clec9A+ DCs in the CMV-GAG-SV40-PRF vaccinated mice compared to CMV-GAG vaccinated mice (mean percentage 2.6 vs. 2.2, p=0.008) (FIG. 6C). This DC subset is capable of sensing necrotic cells and targeting antigen for cross-presentation. Interestingly, there was a decrease in the frequency of Clec9A+ DCs in mice vaccinated with CMV-GAG-SV40-DTa compared to CMV-GAG (mean percentage 1.8 vs. 2.2, p=0.002), suggesting that, although DTa led to antigen-positive cell death, the mechanism did not affect CD8a+ DC, and reduced the frequency of Clec9A+ DC.

The activation status of the DC from the draining lymph node, as measured by MHCII and CD80 expression, was also determined (FIG. 6D). Vaccination with CMV-GAG-SV40-PRF, but not with CMV-GAG-SV40-DTa, induced the up-regulation of both MHCII and CD80 on CD11c+ CD8a+ DC above that observed after vaccination with CMV-GAG (90.5% vs. 84%, p=0.002, and 24.4% vs. 13.4%, p=0.002). The Clec9A+ DCs were already highly activated in all groups (including mock-vaccinated controls), as MHCII and CD80 were expressed on 90-100% and 60-70% of cells respectively, and further increases in activation after vaccination were not detected. Thus, DTa and PRF induced different effects on DC subpopulations after vaccination, and only PRF led to an increase in the frequency of cross-presenting and necrosis-sensing DC, as well as an increase in activation markers, consistent with necrosis-enhanced cross-presentation of antigen.

PRF DNA Vaccination Reduces the EcoHIV Viral Load after Challenge

Figure 7:
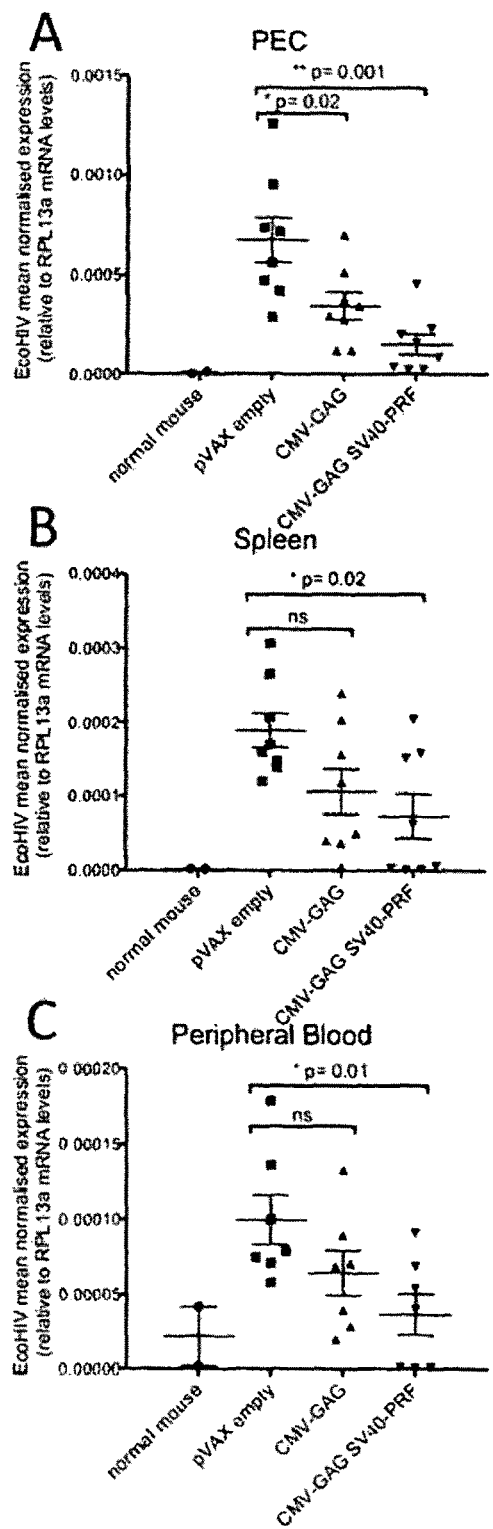
FIG. 7 shows CMV-GAG-SV40-PRF is an effective immunogen against EcoHIV challenge, according to Example 1. EcoHIV challenge after DNA vaccination with 2 doses of 50 μg CMV-GAG, CMV-GAG-SV40-PRF or pVAX empty, 3 weeks apart. The mice were challenged 10 days later with EcoHIV (1.5 μg p24/mouse) and the viral load determined 7 days later. EcoHIV mRNA levels in (A) peritoneal exudate cells, (B) spleen and (C) blood. Vaccinations were performed on groups of 8 female C57BU6 mice. The graphs show mean expression normalised to RPL13a (+/−SEM).

Significant changes in cytokine production by T cells and increased DC activation were observed after vaccination with DNA encoding HIV-1 GAG and the cytolytic protein, PRF. To determine whether these changes represent enhanced immunity to viral infection, vaccinated mice were challenged with EcoHIV, a chimeric HIV in which HIV gp120 has been replaced with gp80 from ecotropic murine leukemia virus. EcoHIV encodes all other HIV proteins, including GAG, from the HIV-1 Clade B NL4-3 strain. Mice received 2 doses of 50 µg CMV-GAG DNA or CMV-GAG-SV40-PRF DNA by the ID route and were then challenged 10 days later with EcoHIV at a dose of 1.5 µg p24 by the IP route, as described previously. Mice were culled 7 days after challenge and tissues were collected to determine the viral load (FIG. 7). Vaccination with CMV-GAG DNA reduced the viral load in the peritoneal exudate cells (PEC) below that detected in mock-vaccinated mice (2-fold reduction in normalised mRNA levels, p=0.02) while vaccination with CMV-GAG-SV40-PRF DNA resulted in a further decrease (5-fold reduction, p=0.001) (FIG. 7A). In the spleen, the CMV-GAG-SV40-PRF DNA, but not the CMV-GAG DNA, vaccination reduced the viral load (2.5-fold, p=0.02) compared to that observed in mock-vaccinated mice (FIG. 7B). Likewise, in the peripheral blood, the viral load was significantly reduced by CMV-GAG-SV40-PRF (2.5-fold, p=0.01) but not by CMV-GAG DNA vaccination (FIG. 7C). Thus, the immune response induced by DNA vaccination containing the cytolytic gene, PRF, resulted in improved control of viral replication at the site of infection, and systemically, in EcoHIV-challenged mice.

The embodiment of the invention described herein includes a method to target antigen for uptake by DC by utilising pathways involved in cellular necrosis, to increase the level of cross presentation of the antigen. The DNA vaccine described, which encodes an antigen of interest and the cytolytic protein PRF, induced necrosis in antigen-positive cells, enhanced DC activation and anti-viral T-cell mediated immunity, and provided increased levels of protection against viral challenge. This approach has advantages over more general mechanisms of inducing cell death at the site of vaccination, such as the use of Alum adjuvants or electroporation, as it limits tissue damage and more closely mimics the effects of lytic viruses, including live attenuated virus vaccines.

Figure 3:
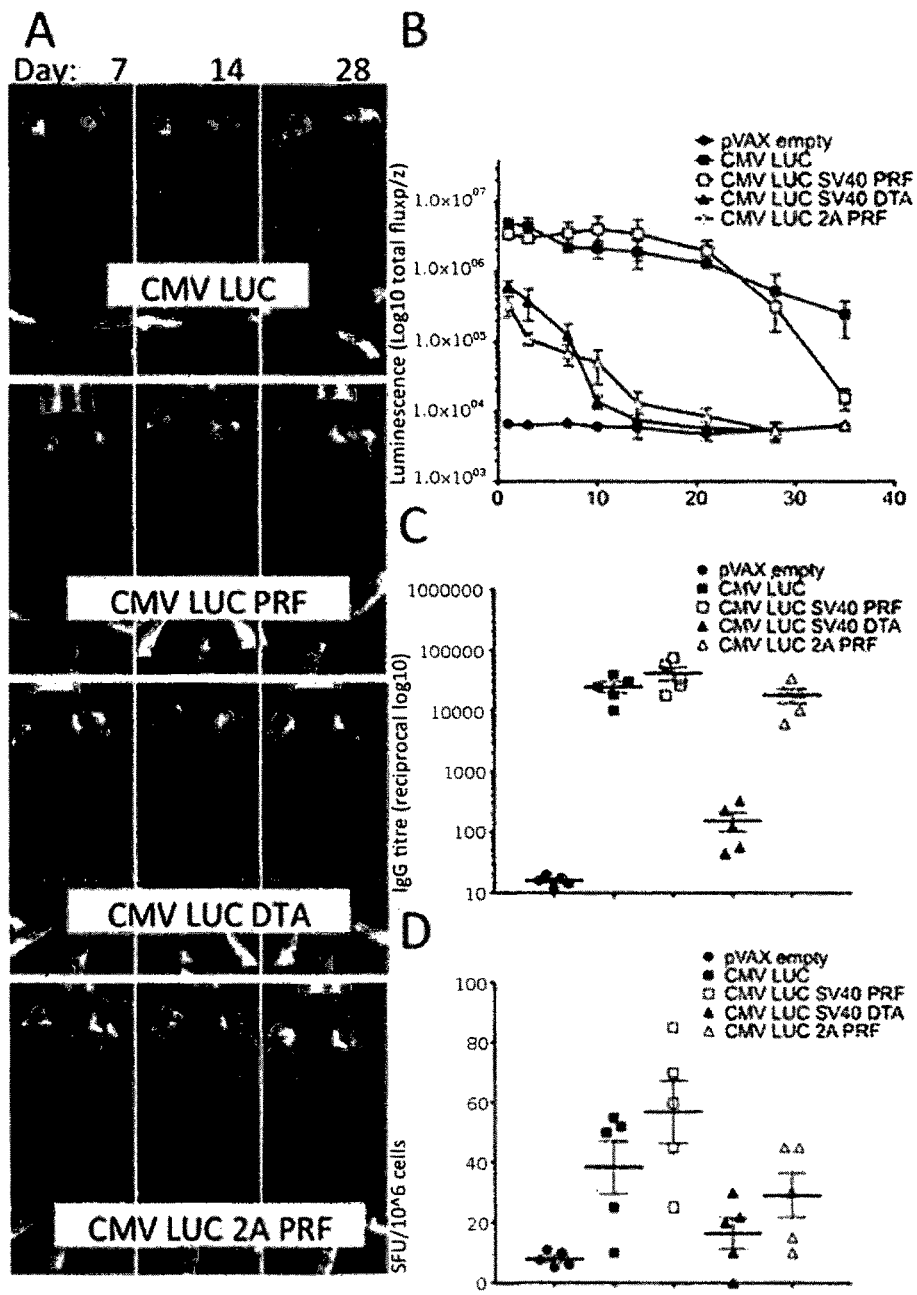
FIG. 3 shows in vivo imagining of luciferase for tracking of antigen expression from DNA vaccines in vivo, according to Example 1. (A) Representative IVIS images of luminescence in the mouse dermis on day 7, 14 and 28 after ID vaccination with 50 μg CMV-LUC+/−PRF or DTa. (B) The longitudinal expression of LUC after ID vaccination as determined by quantification of luminescence in vaccinated mice. (C) Detection of LUC-specific antibody by ELISA. Mice received three vaccinations of 50 μg CMV-LUC+/−DTa or PRF, and serum samples were taken on day 10 after the final dose. (D) IFN ELISPOT to detect LUC-specific T cell responses in splenocytes re-stimulated with an immunodominant LUC peptide. Spleens were harvested at day 10 after the final vaccination. Vaccinations were performed on groups of 5 female C57BL/6 mice. Graphs show mean+/−SEM.
Figure 4:
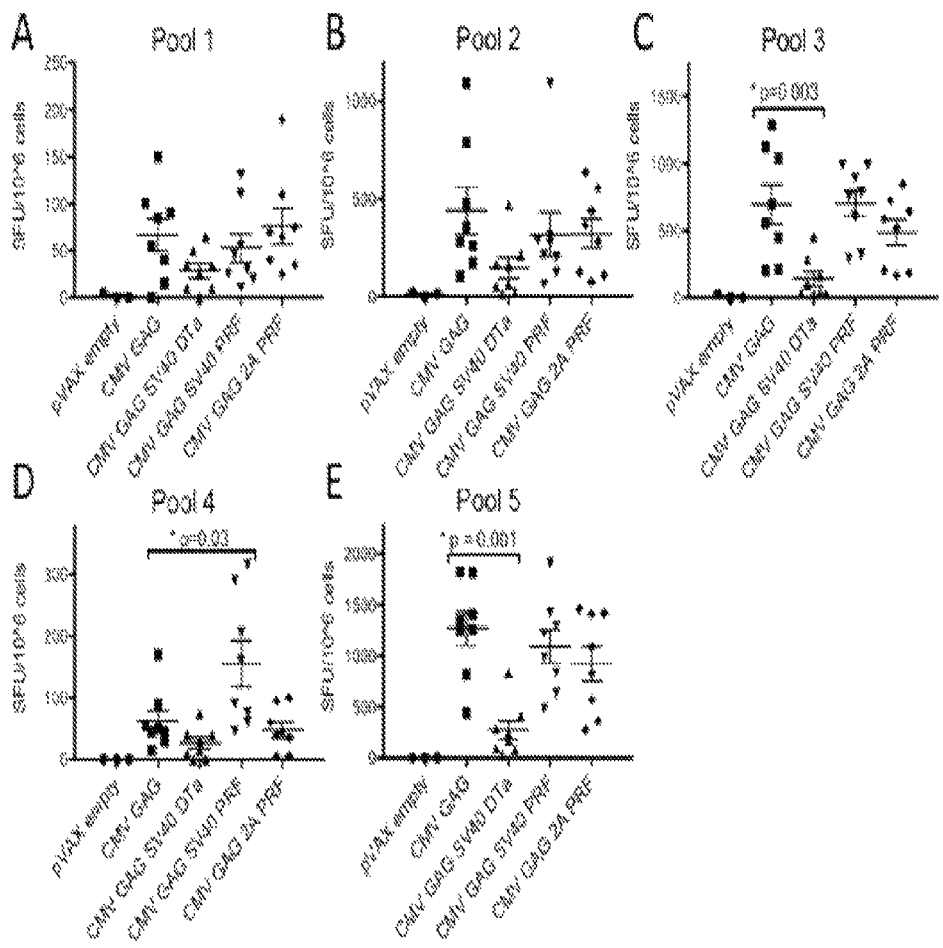
FIG. 4 shows IFN ELISPOT to detect GAG-specific T cell responses, according to Example 1. Mice were vaccinated ID with 50 μg DNA on 3 occasions, 4 weeks apart and spleens harvested on day 10 after the final vaccination. Splenocytes were restimulated with 4 different pools of overlapping peptides covering the complete GAG protein (pools 1-4 shown in A-D respectively), or a final pool of C57BU6 MHCI and II restricted immunodominant peptides (E). Vaccinations were performed on groups of 8 female C57BL/6 mice. Graphs show mean SFU per 10^6 splenocytes (+/−SEM).

Two candidate genes are described, DTa and PRF, which showed differing effects on the kinetics of antigen expression and the subsequent immune response. The necessity for a threshold level and a minimum period of antigen expression is highlighted in this study, as reduced antigen expression and more rapid cell death resulting from increased levels of expression of perforin (CMV-GAG-2A-PRF) failed to enhance the antigen-specific immune response (FIGS. 3 and 4). This fact could only be determined by using the technology of live imaging to track antigen expression. Other cytolytic proteins may also be useful in this system, particularly if their expression results in lytic cell death at a time-point after the threshold of the immunogenic antigen expression is achieved.

This approach induced no more tissue damage than expected from standard ID injection protocols, as cell death was restricted to cells that were previously transfected by the DNA vaccine. However, this approach resulted in an increased frequency of activated CD11c+ CD8a+ DC in the draining lymph nodes, a cell population that is believed to be essential in cross-presentation of antigen to naïve CD8 T cells (FIG. 6). The T cell-mediated immune response following vaccination was also enhanced by the co-expression of perforin, as determined by increased numbers of IFN-secretion by memory T cells in response to stimulation by GAG peptides (FIG. 4). The CMV-GAG vaccine induced strong immune responses when administered via the ID route, but the addition of perforin broadened the immune response by enhancing T cell responses to non-dominant epitopes. Perforin also increased the frequency of CD8 T cells capable of secreting multiple cytokines, a T cell subset shown to be important in control of HIV-1 infection (FIG. 5).

Conversely, DTa failed to activate DCs or enhance immune responses, but instead reduced the immune response to some GAG epitopes. This highlights the importance of the mechanism of cell death in this model. DTa inhibits protein synthesis and results in apoptosis, which is known to be less inflammatory than necrotic cell death. Viral antigen-positive cells that become apoptotic and are cleared before they undergo secondary necrosis are expected to substantially limit DC activation and cross-presentation. These results indicate that necrotic cell death, in human setting, may be equally beneficial compared to, if not better than, apoptotic cell death in immune activation.

A DNA vaccine is described herein encoding an antigen and a cytolytic protein which elicits a higher level of protective immunity as determined by viral challenge than a DNA vaccine which only encodes the antigen, not only at the site of infection in the peritoneal space, but also systemically in the spleen and peripheral blood.

These results confirm that inducing necrosis in viral antigen-positive cells results in increased dendritic cell activation without excessive inflammation, and enhances the type of immune response important to control infection.

EXAMPLE 2

Materials and Methods

Briefly, DNA encoding luciferase was used as proof of principle. TK/GCV was used to determine if co-expression of luciferase and TK, followed by administration of ganciclovir increased the efficacy of DNA vaccination in mice. Constitutive co-expression of luciferase and a toxic protein was carried out to detect any increase in the level of the immune response against luciferase. To ensure that the expression of a toxic protein was not premature, and result in early death of cells targeted by the vaccine, the expression of the toxin was placed under the control of the SV40 promoter that is weaker than the CMV immediate early promoter (termed CMV promoter in this document) used to drive expression of the luciferase (or other immunogenic protein).

Construction of the Luciferase/TK DNA Vaccine

The modified Luciferase gene was amplified from a plasmid, and was inserted into the pVAX backbone (Invitrogen) under the control of the CMV promoter and upstream of the BGH polyadenylation sequence. The pVAX plasmid was digested with NheI and EcoR1 restriction enzymes and the modified Luciferase 2 gene ligated into the digested pVAX with T4 DNA ligase (NEB). The DNA was transformed into electrocompetent DH5alpha *E. coli* and positive clones were selected on kannamycin agar plates. The presence of the insert was confirmed by re-digestion and DNA sequencing.

Figure 8:
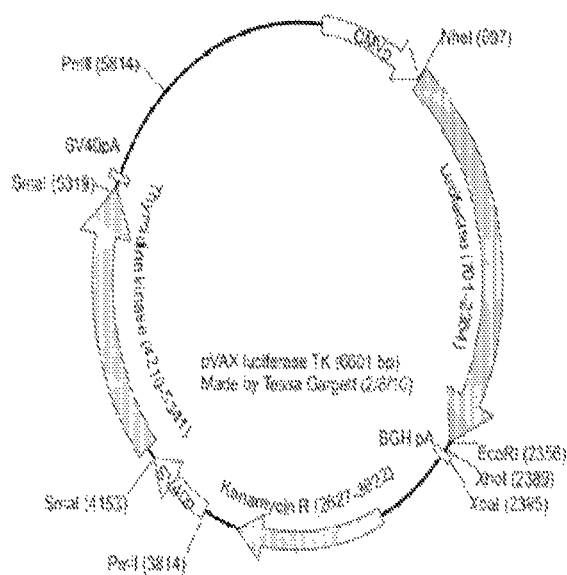
FIG. 8 shows a plasmid map of the pVAX luciferase-TK plasmid prepared for the bicistronic expression of luciferase and thymidine kinase (TK), according to Example 2.

The SV40 promoter, thymidine kinase (TK) gene and polyadenylation sequence were amplified from a plasmid. This plasmid contained the herpes simplex virus TK gene. The SV40 promoter, TK gene and SV40 poly (A)+ site were inserted into the pVAX-luciferase backbone by digestion with the restriction enzyme, PmlI, ligated into pVAX with T4 DNA ligase (NEB) and positive clones were selected and tested as described above (FIG. 8).

Construction of the Luciferase/NSP4 DNA Vaccine

The modified Luciferase gene was amplified from a plasmid and was inserted into the pVAX backbone (Invitrogen) under the control of the CMV promoter and upstream of the BGH polyadenylation sequence. The pVAX plasmid was digested with NheI and EcoR1 restriction enzymes and the modified Luciferase 2 gene ligated into the digested pVAX with T4 DNA ligase (NEB). The DNA was transformed into electrocompetent DH5alpha *E. Coli* and positive clones were selected on kannamycin agar plates. The presence of insert was confirmed by re-digestion and DNA sequencing.

The SV40 promoter and polyadenylation sequence were amplified from a plasmid. This plasmid was based on pcDNA3. The SV40 promoter and SV40 poly (A)+ site were inserted into the pVAX-luciferase backbone by digestion with the restriction enzyme, PmlI, ligated with T4 DNA ligase (NEB) and positive clones were selected and tested as described above.

The NSP4 gene was amplified by PCR from an expression construct, and inserted into the pVAX-luciferase plasmid under the control of the SV40 promoter and upstream of the SV40 polyadenylation sequence by digestion with SmaI restriction enzyme, the fragments ligated and selected as described above (FIG. 9).

Construction of the Luciferase/PRF DNA Vaccine

The modified Luciferase gene was amplified from a plasmid and was inserted into the pVAX backbone (Invitrogen) under the control of the CMV promoter and upstream of the BGH polyadenylation sequence. The pVAX plasmid was digested with NheI and EcoR1 restriction enzymes and the modified Luciferase 2 gene ligated into the digested pVAX with T4 DNA ligase (NEB). The DNA was transformed into electrocompetent DH5alpha *E. Coli* and positive clones were selected on kannamycin agar plates. The presence of insert was confirmed by re-digestion and DNA sequencing.

The SV40 promoter and polyadenylation sequence were amplified from a plasmid. This plasmid was based on pcDNA3. The SV40 promoter and SV40 poly (A)+ site were inserted into the pVAX-luciferase backbone by digestion with the restriction enzyme, PmlI, ligated with T4 DNA ligase (NEB) and positive clones were selected and tested as described above.

The PRF gene was amplified by PCR from an expression construct and inserted into the pVAX-luciferase plasmid under the control of the SV40 promoter and upstream of the SV40 polyadenylation sequence by digestion with SmaI restriction enzyme, the fragments ligated and selected as described above (FIG. 10).

Vaccination Schedule

Eight week old C57Bl/6 mice were pre-bled and vaccinated with 50 µg of DNA by the intradermal route (ear) on 2 occasions, 5 weeks apart with pVAXLUC alone, pVAX-LUC-TK+/−GCV, or pVAXLUC-NSP4. Luciferase expression was measured by luminescence every 7 days until luminescence decreased. Four weeks later, the mice were culled and blood collected to examine the humoral immune response to luciferase. In further experiments to analyse the antibody response, the mice were vaccinated via the intradermal route with 50 µg of pVAXLUC, pVAXLUC-TK+/−GCV, pVAXLUC-NSP4 or LUC-PRF on day 0, day 28 and day 56 and the antibody titer measured 10 days later. In experiments to analyse the cell mediated immune response, pVAXLUC, pVAXLUC-NSP4, pVAXLUC-TK+/−GCV or pVAXLUC-PRF, and pVAX, pVAXGagNSP4,or pVAX-GagPRF vaccinated mice received 3×50 µg DNA at 4 week intervals via the intradermal route and the immune response also examined by ELIspot or intracellular cytokine staining 10 days later.

Temporal Expression of Luciferase

Figure 11:
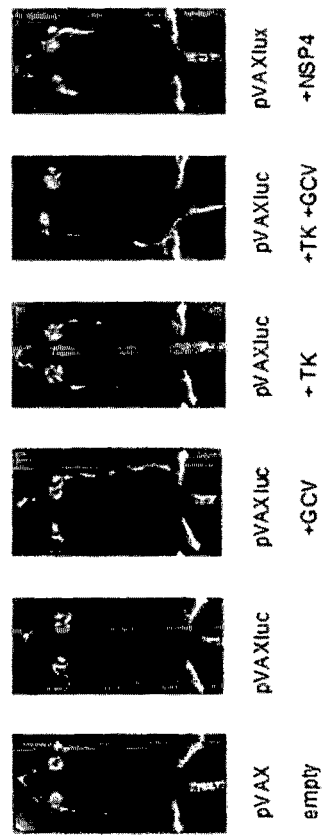
FIG. 11 shows photographs of luciferase expression in mice transfected with the plasmids of FIG. 9 or pVAX (not shown), the plasmids with which the mice were transfected are indicated below the photographs, according to Example 2.
Figure 12:
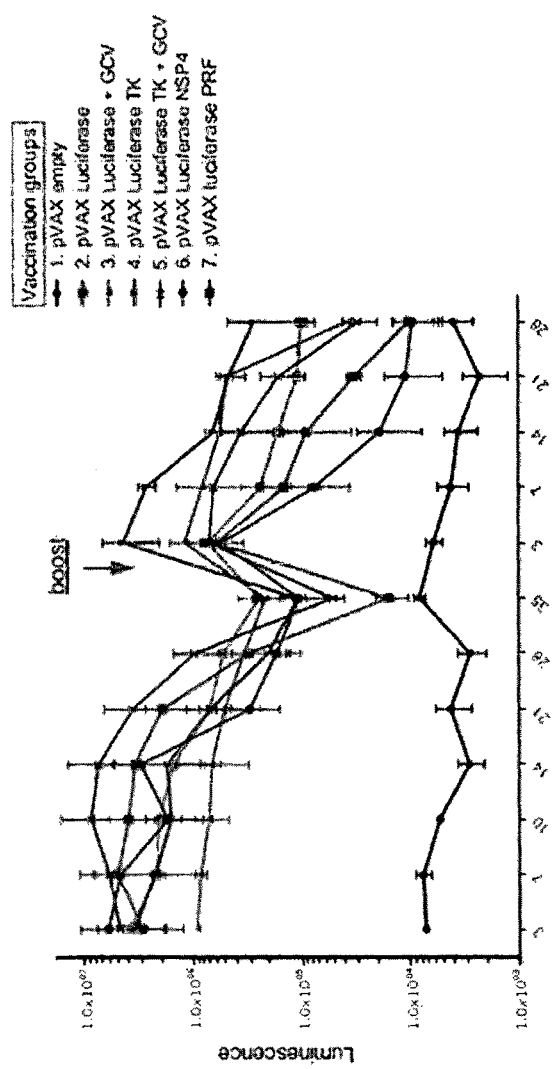
FIG. 12 shows a graph representing luminescence expression over time after intra-dermal DNA vaccination of mice, according to Example 2.

Luminescence was detected from day 1 using a Xenogen IVIS live imager. Mice were sedated and then injected with 150 µL D-luciferin by the intraperitoneal route. After 10 minutes incubation to allow the DNA vaccine-expressed luciferase to react with the luciferin, the mice were placed in the Xenogen IVIS and photographed. Luminescence was detected by Living Image software as photons per second (FIG. 11). Luminescence is a direct measure of recent luciferase expression as luciferase has a half-life of only 3 hours. Thus, luciferase expression (FIG. 12) continued for at least 4 weeks and slowly decreased until on day 35 it was 1-2 log fold lower than on day 3.

No difference was seen in luminescence levels between the luciferase controls (pVAXluc, pVAXluc +GCV, pVAXluc +TK), or luciferase with adjuvant (pVAXluc +TK +GCV or +NSP4 or +PRF) groups after the initial DNA vaccine prime (day 0). All groups showed high levels of luciferase expression between days 3 and 21, with a slow reduction in expression between day 21 and day 35 at which point it was 1-2 log fold lower than on day 3.

After the DNA vaccine boost, the pVAXluc +NSP4 and pVAXluc +PRF groups showed a more rapid reduction in luciferase expression over time, compared to the other groups. (FIG. 12) Additional experiments showed that luminescence disappeared completely between days 35 and 49, depending on the initial level of expression.

Anti-Luciferase Antibody Titres in Vaccinated Mice

Figure 13:
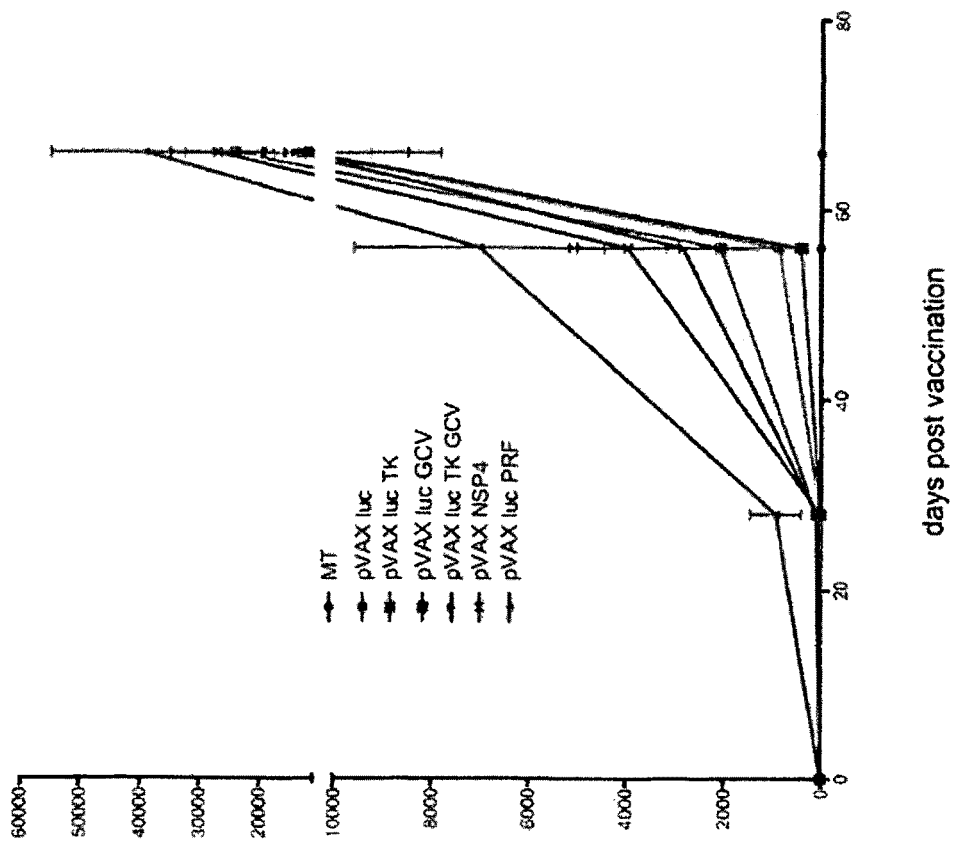
FIG. 13 shows a graph representing luciferase specific antibody detected in mice after vaccination with the plasmids of FIG. 8, 9 or 10, according to Example 2.
Figure 14:
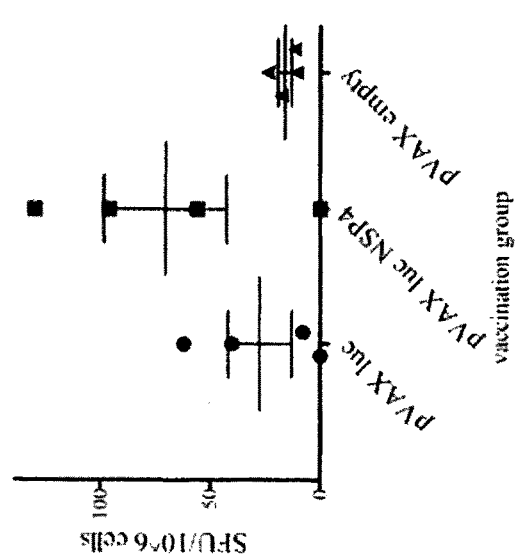
FIG. 14 shows a graph representing anti-luciferase cell mediated immunity detected in mice after vaccination with the plasmids of FIG. 9, according to Example 2.

Recombinant firefly luciferase protein was used to coat ELISA plates, and serial dilutions of mouse serum were incubated at 37° C. for one hour. Anti-luciferase IgG was then detected with anti-mouse IgG conjugated with horseradish peroxidase (HRP). After incubation with orthophenylene diamine (OPD) substrate, the colour change in the substrate was measured by a spectrophotometer. Initial experiments in which mice were vaccinated with 50 µg DNA on 2 occasions showed that the titre of anti-LUC, detected by Elisa was 1/256 for the LUC and 1/4096 for the LUC+NSP4 DNA. Similar anti-LUC antibody titres were generated with TK/GCV treatment, but co-expression of TK without the later administration of GCV had no effect on anti-LUC titres. The anti-luciferase antibody titre was then measured in mice vaccinated with pVAXLUC, pVAXLUC (with the later administration of GCV, as a control) or pVAXLUC +TK (without the later administration of GCV) and was approximately 1/10,000. In mice vaccinated with pVAXLUC +TK (plus the later administration of GCV) or with pVAXLUC +NSP4 the anti-luciferase antibody titre was approximately 1/20,000 while vaccination with pVAXLUC +PRF resulted in an anti-luciferase antibody titer of approximately 1/40,000 (FIG. 13). Importantly, the antibody titre rose much more rapidly in the pVAXLUC +NSP4 and pVAXLUC +PRF vaccinated mice (FIG. 13).

Cell Mediated Responses to Luciferase in Vaccinated Mice

The cell mediated responses to luciferase were measured by ELIspot. Splenocytes were harvested from the mice, 7 days post final vaccination and stimulated with a peptide derived from luciferase. The results of this experiment showed that pVAXLuc +NSP4 vaccination resulted in a 3-fold increase in the frequency of IFN-expressing cells. Similarly, vaccination with pVAXLuc +PRF resulted in a 2-fold increase in frequency of IFN positive cells over vaccination with pVAXLuc along, and in the frequency of multifunctional T cells (FIGS. 14, 15, 18-20).

The results set out herein show that the use of suicide gene therapy can increase the immune response against a specific immunogen encoded by a DNA vaccine. This strategy can be applied equally to immunogens encoded by replication-defective recombinant vaccine vectors or even to replication-competent vaccine vectors both of which may normally be non-cytolytic.

The results set out herein also show that constitutive expression of a toxic protein simultaneously with the immunogen resulted in increased levels of immunity most likely as a result of increased cross presentation. Thus, there is no need for the subsequent administration of reagents such as a prodrug or a compound which can activate an inducible promoter, so that it is no longer necessary to administer ganciclovir to patients for example. Although the use of zinc to activate a metallothionein promoter may be effective in animals, it is unlikely to be equally effective in humans, in whom zinc is a crucial element that is continually present.

An effective vaccine will, by necessity, need to induce an inflammatory response that is unlikely to be achieved by suicide genes which induce apoptosis.

EXAMPLE 3

The following data illustrate another embodiment of the invention in which a mouse cell line, DC 2.4, was transfected with RNA encoding the HCV NS3 protein. The transfected cells were made necrotic by heat treatment at 63° C. for 30 min, to produce a syngeneic vaccine of the invention.

Necrotic, Viral Antigen Positive Cells are Highly Immunogenic

Figure 16:
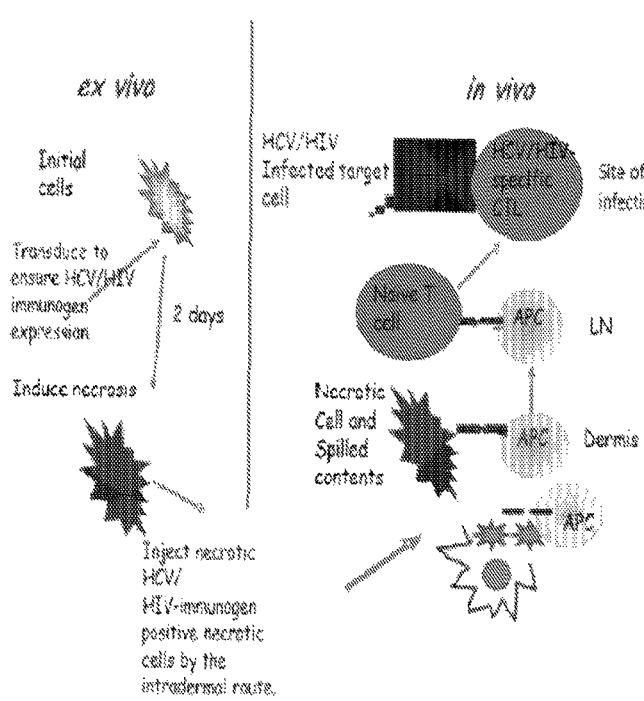
FIG. 16 shows a diagrammatic representation of the processes of necrosis of a HCV/HIV immunogen expressing cell ex vivo, the APC phagocytosing the antigen in vivo, presentation of the antigen by the APC to a T cell, and recognition of an infected cell by the activated T cell, according to Example 3.
Figure 15:
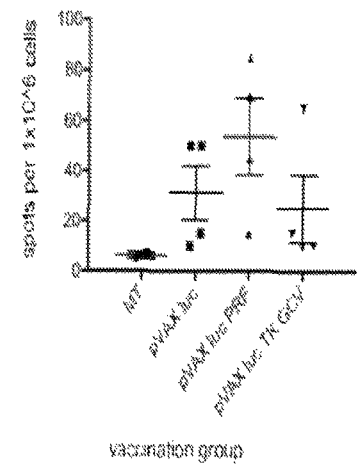
FIG. 15 shows a graph representing anti-luciferase cell mediated immunity detected in mice after vaccination with the plasmids of FIGS. 8 and 10, according to Example 2.
Figure 17:
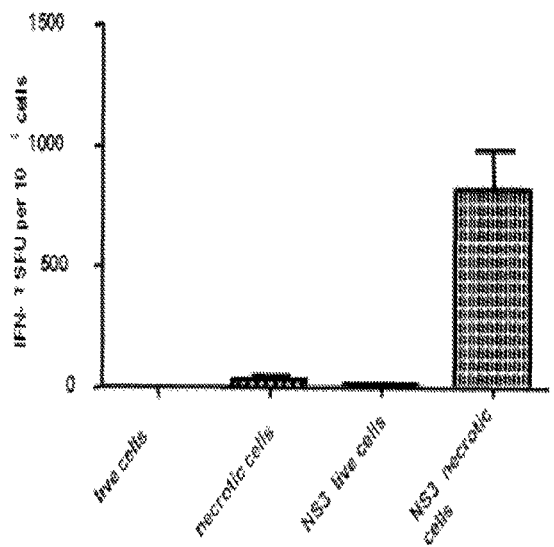
FIG. 17 shows ELIspot analysis of peptide-stimulated splenocytes representing the poorly immunogenic HCV NS3 protein harvested from mice vaccinated with the necrotic HCV NS3-positive cell line, compared to vaccination with the same live cell line. The HCV NS3-positive, necrotic cells illicit cell mediated immunity more effectively than viable cells. DC 2.4 cells were transfected with RNA encoding the HCV NS3 protein. A proportion was made necrotic. C57Bl/6 mice were vaccinated by the subcutaneous route as follows; G1, $10^6$ untransfected, live cells G2, $10^6$ NS3 untransfected, necrotic cells; G3; $10^6$ NS# transfected, live cells; G4, $10^6$ NS3 transfected, necrotic cells. Splenocytes were stimulated with NS3 peptides in an ELIspot assay, according to Example 3.

Preclinical studies of a necrotic whole cell vaccine were performed. A schematic diagram of the strategy is shown in FIG. 16. A mouse cell line, DC2.4, was transfected with RNA encoding the HCV NS3 protein (This RNA sequence was published by R Trowbridge and E J Gowans (Trowbridge R and Gowans E J (1998). *Molecular cloning of an Australian isolate of hepatitis C virus*. Arch. Virol 143:501-511) and the sequence deposited in Genebank under accession number AJ000009) and 48 hours later these cells were induced to become necrotic by heating the cells to 63° C. for 30 minutes. Subcutaneous vaccination with these cells in groups of 6 mice induced far higher CMI responses (80-100 fold in different experiments, as determined by ELIspot analysis of peptide-stimulated splenocytes representing the poorly immunogenic HCV NS3 protein), compared to vaccination with the same live cell line (FIG. 17). In these experiments, the mice received approximately 100 ng of the NS3 protein by comparison of the intensity of the band detected in Western blot with that of commercially available purified NS3.

Furthermore, the responses elicited by the necrotic cells were much higher than detected with other (canonical) vaccination regimens, such as DNA vaccination, that typically generate ~100 spot forming units/$10^6$ cells.

EXAMPLE 4

Figure 18:
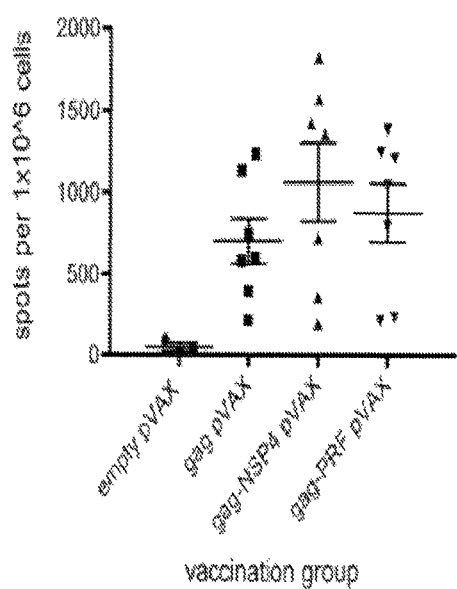
FIG. 18 shows the frequency of murine splenocytes, stimulated ex vivo with immunodominant gag peptides after vaccination with pVAXgag, pVAXgag +NSP4 or pVAXgag +PRF as determined by ELIspot, according to Example 4.

In a similar manner described in FIGS. 3 and 4, the gag sequence from the HIV genome was inserted into pVAX upstream of the NSP4 and PRF cistrons respectively, to result in DNA vaccines pVAXgag +NSP4 and pVAXgag +PRF. C57Bl/6 mice were vaccinated with 50 µg of these DNA vaccines by the intradermal route described above, on 3 occasions, 4 weeks apart. These results showed that the pVAXgag +NSP4 induced approximately a 1.5-fold increase in IFN secreting T splenocytes while pVAXgag +PRF induced a 1.3-fold increase over pVAXgag alone when the splenocytes were stimulated with recognised gag immunodominant peptides in an ELIspot assay (FIG. 18).

To analyse these responses in greater detail, CD8$^+$ and CD8$^-$ memory cells (CD44$^+$) were stimulated ex vivo with the immunodominant gag peptides and the expression of IFN, TNF and IL-2 examined by intracellular cytokine staining followed by flow cytometry. The expression of multiple cytokines in individual cells was suggested to represent a prerequisite for a successful vaccine able to protect against challenge (R Seder, P A Darrah and M Roederer (2008) T-cell quality in memory and protection: implications for vaccine design. Nat Rev 8: 247-258). The results of these experiments showed that the frequency of CD8+ memory cells with the ability to synthesize all three cytokines in individual cells was increased by 1.7-fold by pVAXgag +NSP4 and by 2.7-fold by pVAXgag +PRF (FIG. 19).

Likewise, although CD8+ T cells are often recognized as the cells which kill virus-infected cells, CD4+ cells which express multiple cytokines are necessary for T cell help. Consequently, CD8−, CD44+ memory T cells from the vaccinated mice were also examined by multicolour flow cytometry to analyse the synthesis of IFN, TNF and IL-2 in individual cells. The results showed that, although pVAX +NSP4 showed no increase in the frequency of these multifunctional T cells after peptide stimulation, T cells from mice vaccinated with pVAXgag +PRF showed a 3-fold increase in this cell population (FIG. 20).

EXAMPLE 5

Materials and Methods

Preparation of Stable DC2.4 Cell Line Expressing Codon Optimised NS3 g1B

Third-generation lentiviral vectors containing the human hepatitis B virus posttranscriptional regulatory element (PRE) and the HIV central polypurine tract (cPPT) element (described in Barry et al, 2001 and Brown et al, 2010) were used for all experiments. For NS3 g1b overexpression, the backbone was reengineered to contain the elongation factor (EF)-1 promoter (plvEIG), a Gateway cloning site (att, CAT ccdB att), and an internal ribosome entry site (IRES) to drive the marker gene encoding green fluorescent protein (GFP). To generate the HCV NS3 delivery vector, this backbone was engineered to contain a Gateway cassette (att, CAT ccdB att) upstream of the Rev-responsive element into which the NS3 cassette was recombined. HCV NS3 g1b was inserted under the control of the EF-1 promoter, and the marker gene (GFP) was expressed from the IRES. To generate NS3 lentiviral stocks, HEK293T cells were seeded at a density of $6 \times 10^6$ cells in 18 ml of medium in a 75-cm$^2$ tissue culture flask. Cells were transfected with 12.5 g of NS3 transfer vector (plvEIG), 7.5 g of Gag/Pol (8.2), 6.25 g of Rev (pRSV-Rev), and 3.75 g of Env (pCMV-VSV-G), using Lipofectamine LTX reagent (Invitrogen) and Opti-MEM (Invitrogen) reduced serum medium, in accordance with the standard protocol. The next day, the medium was replaced with 10 ml of fresh RPMI and 48 hr later supernatant was collected, filtered (pore size, 0.45 m), and used immediately or stored frozen (−70° C.)

For the transduction of the murine DC2.4 cell line, cells were seeded at a density of $2 \times 10^5$ cells per well in a 6-well plate. Medium was replaced with 3 ml of viral supernatant (unconcentrated) containing Polybrene at a final concentration of 8 g/ml. NS3-CFP-positive cells were sorted by flow cytometry (FACSAria; BD Biosciences, San Jose, Calif.) until purity reached 96%.

Stimulation of Necrosis Stable DC2.4 Cell Line Expressing Codon Optimised NS3 g1B NS3 DC2.4 cells were resuspended in PBS. The cells were heated to 63° C. for 30 min to induce necrosis. Necrosis was confirmed by trypan blue staining and flow cytometry.

Flow Cytometric Detection of Necrotic Cells

Necrotic NS3 DC 2.4 cells were assayed by flow cytometry (FACSCanto, BD Biosciences, San Jose, Calif.). Necrosis was confirmed by checking FFC and SSC characteristics of DC2.4.

Results

Flow Cytometric Detection of Necrotic Cells

Figure 21:
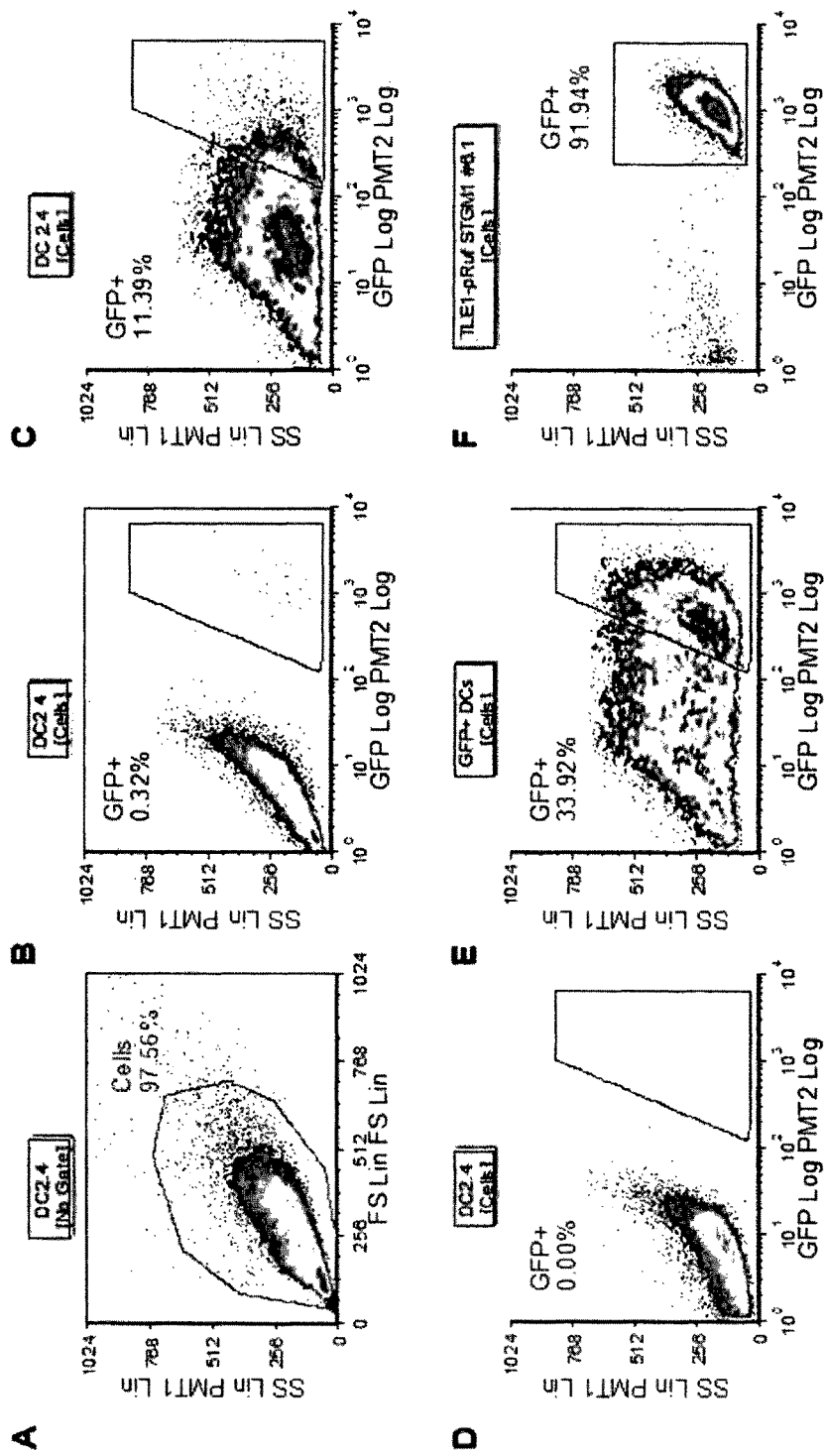
FIG. 21 shows flow cytometry scatter plots of the stable DC2.4 cell line expressing codon optimised NS3 g1b used in necrotic cell vaccinations according to Example 5.

A stable DC2.4 cell line was prepared expressing codon optimized NS3 g1b. 97.56% of the sample of stable DC2.4 cells expressing codon optimized NS3 g1B were collected (FIG. 21A). This population of GFP positive transduced cells were collected 7-8 days post-transduction using standard flow cytometric sorting techniques. After the fourth sort, the purity of the GFP positive cells was improved to 93-95% (FIG. 21B-F).

Figure 22:
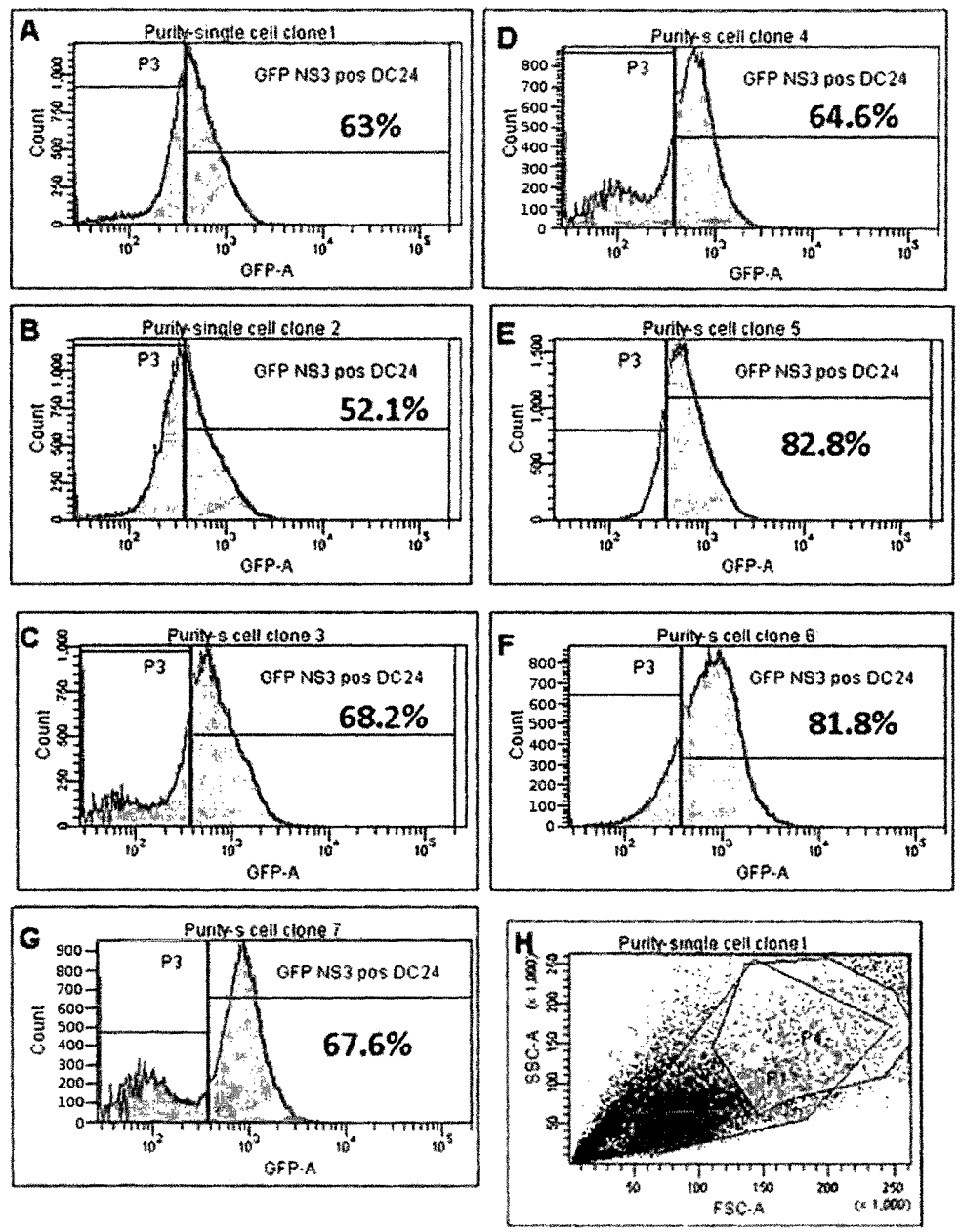
FIG. 22 shows the percentage of GFP positive cells in each of the single clones of the stable DC2.4 cell line expressing codon optimised NS3 g1b used in necrotic cell vaccinations according to Example 5.

Seven stable DC2.4 cell line clones were prepared. The percentage of GFP positive cells of each cloned cell line varied between 52.1% to 82.8% (FIG. 22A-G), as detected using the flow cytometric techniques described above, the gating parameters for which are illustrated in FIG. 22H.

Kinetics of Cell Activation Following a Single Dose of Necrotic or Live Vaccination A single dose of $10^6$ cells, representing live or necrotic cells of the stable NS3 g1b expressing DC2.4 cell line prepared, was administered to mice, and samples taken on days 0, 2, 3, 5 and 7. Samples from draining LN (localised) and spleen (systemic) were taken and assayed for i) T cell activation (CD3/CD4/CD8/CD25/CD69); ii) DC activation (CD11c/CD8/MHCII/CD80/CD86); iii) Clec9A DCs (Clec9A/CD11c/CD8/MHCII/CD4); iv) GFP expression in draining LN post vaccination; and v) cell numbers in draining LN.

Figure 23:
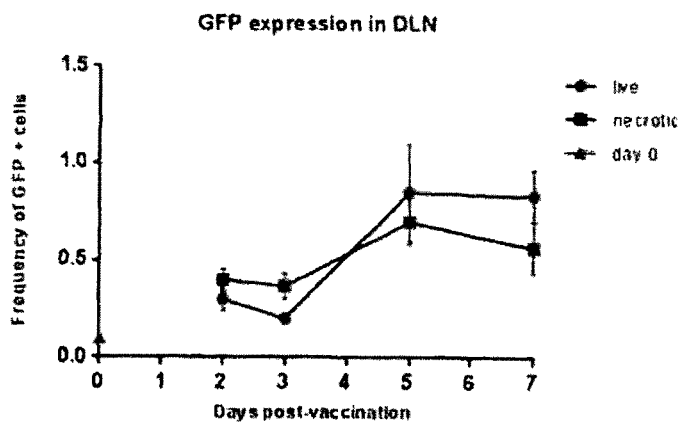
FIG. 23 shows the GFP expression in DLN obtained from vaccinated mice after vaccination according to Example 5.
Figure 24:
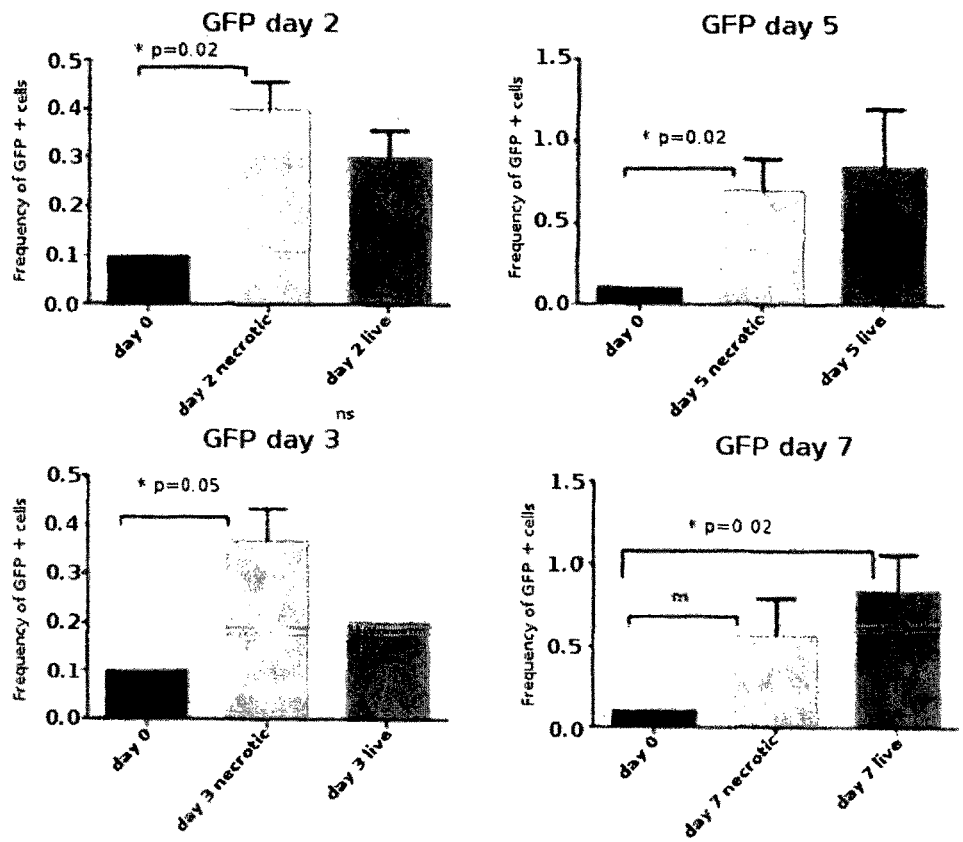
FIG. 24 shows the frequency of GFP positive cells, in DLN obtained from vaccinated mice 2, 3, 5 and 7 days after vaccination with NS3 positive, live or necrotic DC2.4 cells according to Example 5.

FIG. 23 shows the frequency of GFP positive cells at days 2, 3, 5, and 7 post-vaccination. FIG. 24A-D shows GFP expression in DLN at days 2, 3, 5, and 7. The frequency of necrotic GFP positive cells in DLN was found to be significantly increased after 2, 3, and 5 days. After 7 days, the frequency of live GFP positive cells was significantly increased.

$CD11c^{high}$ Cells in DLN Post Single Dose of Necrotic or Live Vaccine.

Figures 25, 26:
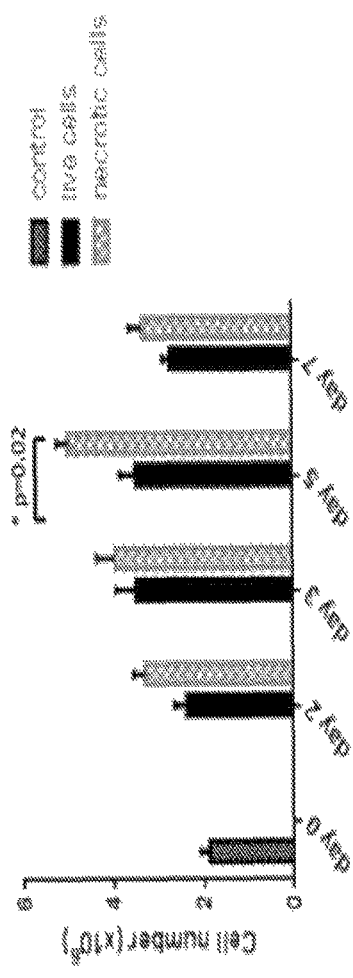
FIG. 25 shows the total numbers of lymphocytes in DLN obtained from vaccinated mice 2, 3, 5 and 7 days after vaccination according to Example 5.
FIG. 26 shows the frequency of CD11c$^{high}$ DCs in DLN, relative to frequency and total cell number, obtained from vaccinated mice 2, 3, 5 and 7 days after vaccination according to Example 5.
Figure 27:
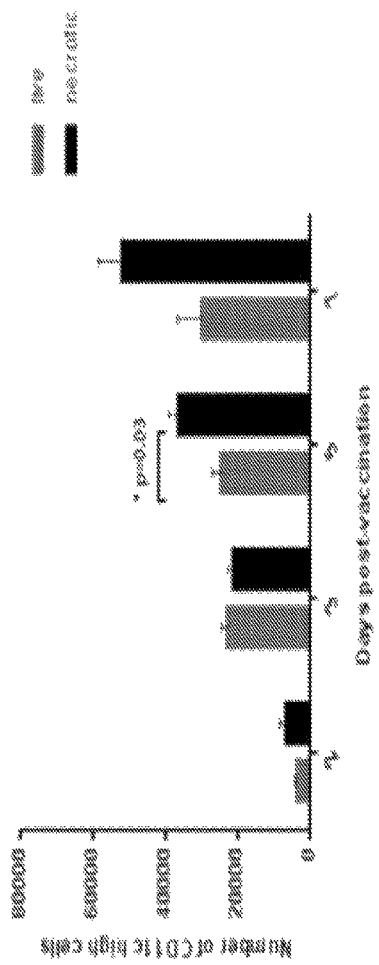
FIG. 27 shows the number of CD11c$^{high}$ DCs in DLN obtained from mice vaccinated with live or necrotic cells on 2, 3, 5 and 7 days after vaccination according to Example 5.

As shown in FIG. 25, the number of necrotic cells in LN was significantly increased relative to the number of live cells 5 days post vaccination. However, the number of necrotic $CD11c^{high}$ cells in DLN was highest 7 days post vaccination (FIG. 26). The relative frequency of necrotic $CD11c^{high}$ cells to live cells relative to frequency and total cell number total cells was significantly increased 5 days post vaccination (FIG. 27).

Figure 28:
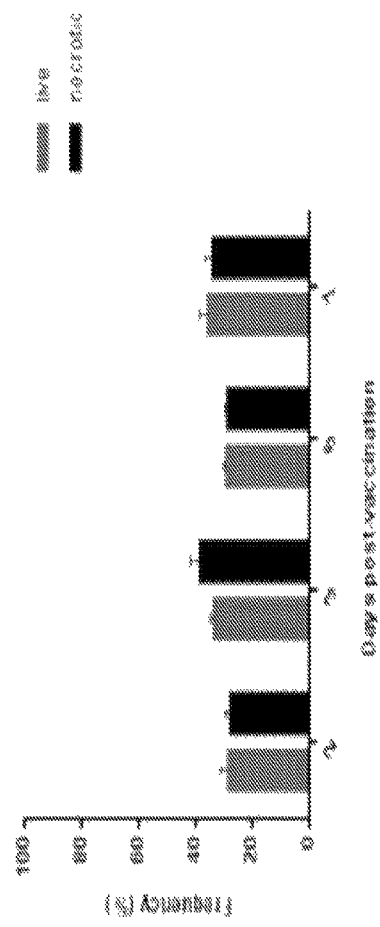
FIG. 28 shows the frequency of CD11c$^{high}$ CD8 DCs in DLN obtained from mice vaccinated with live or necrotic cells on 2, 3, 5 and 7 days after vaccination according to Example 5.
Figure 29:
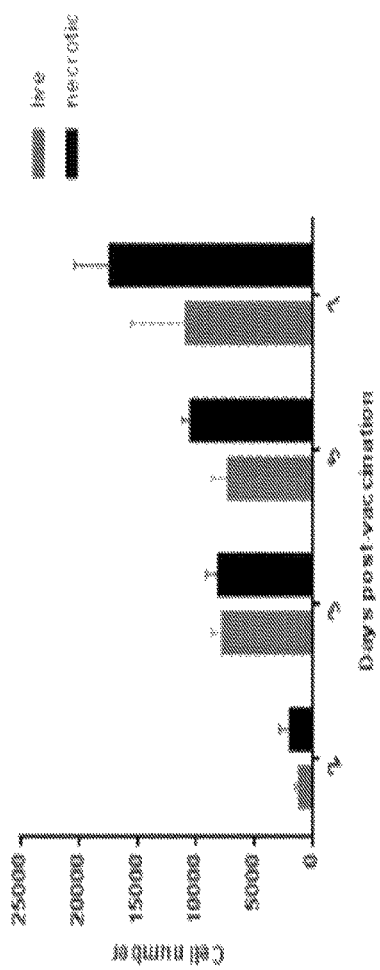
FIG. 29 shows the cell number of CD11c$^{high}$ CD8 DCs in DLN obtained from mice vaccinated with live or necrotic cells on 2, 3, 5 and 7 days after vaccination according to Example 5.

The frequency of necrotic $CD11c^{high}$ CD8 cells in DLN did not significantly change over time (FIG. 28). However, the number of necrotic $CD11c^{high}$ CD8 cells in DLN was highest 7 days post vaccination (FIG. 29).

Figure 30:
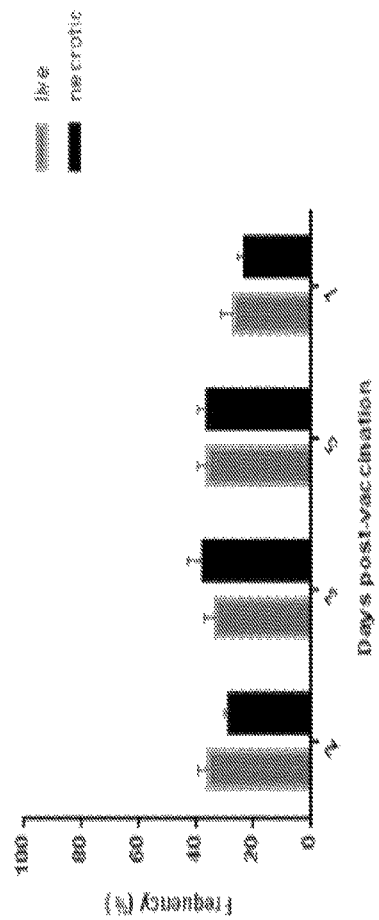
FIG. 30 shows the frequency of Clec9A$^+$ CD11c$^{high}$ CD8 DCs in DLN obtained from mice vaccinated with live or necrotic cells on 2, 3, 5 and 7 days after vaccination according to Example 5.
Figure 31:
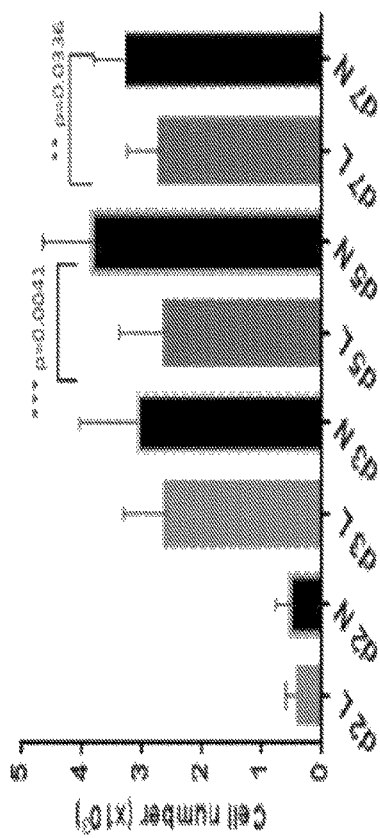
FIG. 31 shows the cell number of Clec9A+ CD11c$^{high}$ CD8 DCs in DLN obtained from mice vaccinated with live or necrotic cells on 2, 3, 5 and 7 days after vaccination according to Example 5. Grey bars represent mice vaccinated with live cells while black bars represent mice vaccinated with necrotic cells.

The frequency of necrotic $CD11c^{high}$ CD8+ Clec9A+ cells in DLN did not significantly change over time (FIG. 30). However, the number of necrotic $CD11c^{high}$ CD8+ Clec9A+ cells in DLN was significantly higher than live cells 5 days and 7 days post vaccination (FIG. 31).

Figure 32:
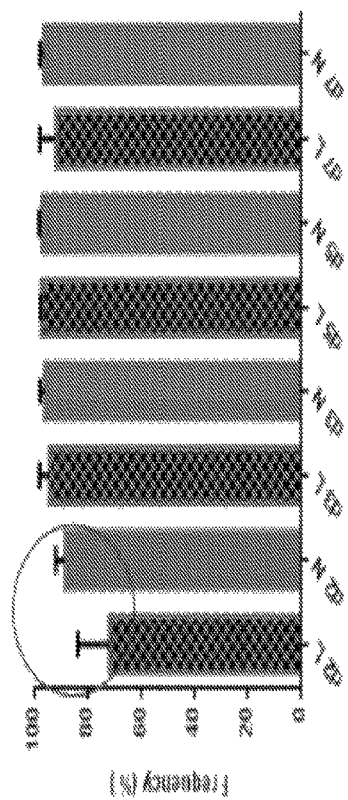
FIG. 32 shows the frequency of Clec9A CD11c$^{high}$ CD8 DCs in DLN obtained from mice vaccinated with live or necrotic cells on 2, 3, 5 and 7 days after vaccination according to Example 5.
Figure 33:
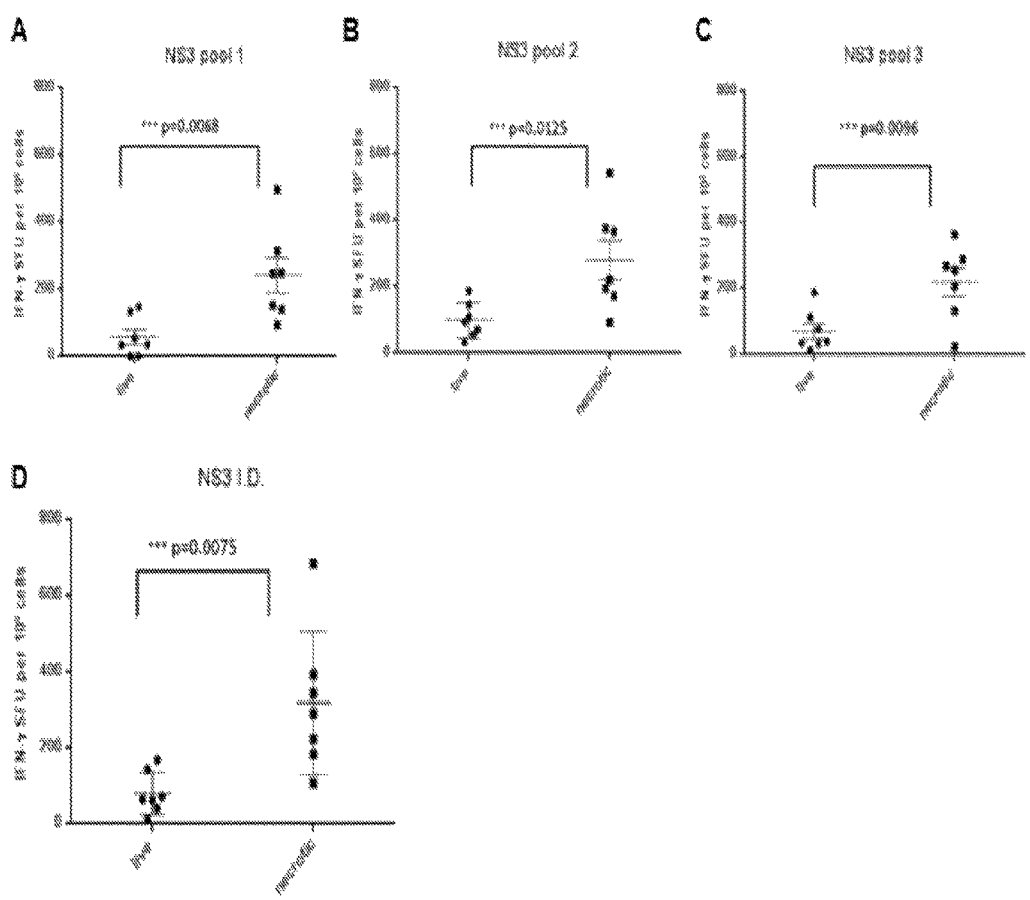
FIG. 33 shows an ELISPOT of mouse splenocytes stimulated ex vivo with NS3 peptide pools after prime and boost according to Example 5.
Figure 34:
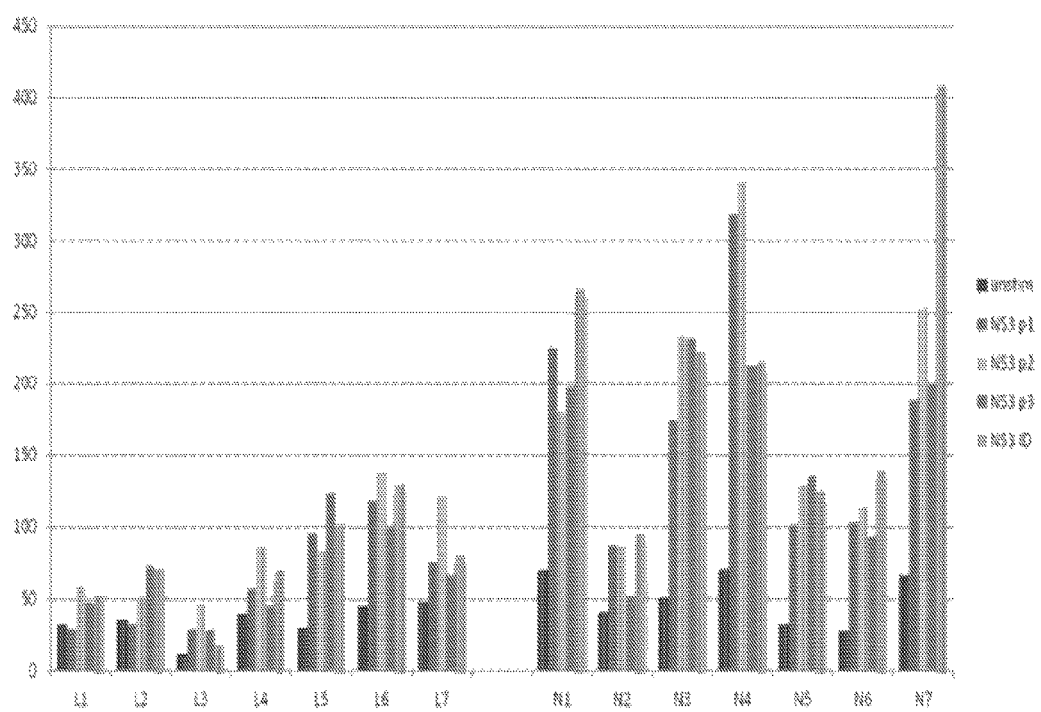
FIG. 34 shows ELISPOT data of splenocytes from individual mice after prime and boost according to Example 5.
Figure 35:
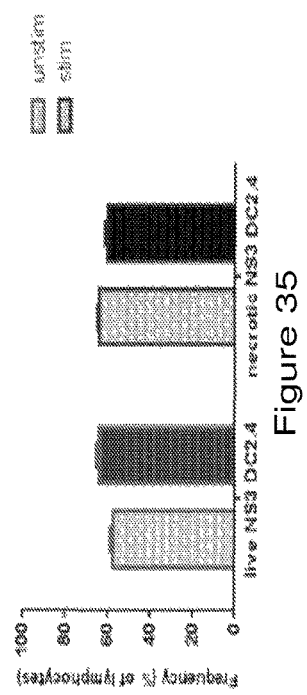
FIG. 35 shows the frequency of CD8+ CD44+ DCs in DLN obtained from vaccinated mice after vaccination according to Example 5.

The frequency of necrotic $CD11c^{high}$ CD8+ MHCII+ Clec9A+ cells in DLN significantly higher than live cells 2 days post vaccination (FIG. 32).

NS3 Cells in DLN Post Boost Dose of Necrotic or Live Vaccine.

Mice were vaccinated with $10^6$ cells prime, then a boost was similarly administered 7 days later. Samples were taken 14 days after the boost was administered and 3 pools of NS3 cells collected.

As shown in FIGS. 33A-D and FIG. 34, the number of interferon-gamma secreting cells was significantly greater in mice vaccinated with the necrotic NS3 cells in all three pools, compared with mice vaccinated with the viable NS3 cells, indicating greater IFNg responses for all pools in mice vaccinated with necrotic cells.

Figure 36:
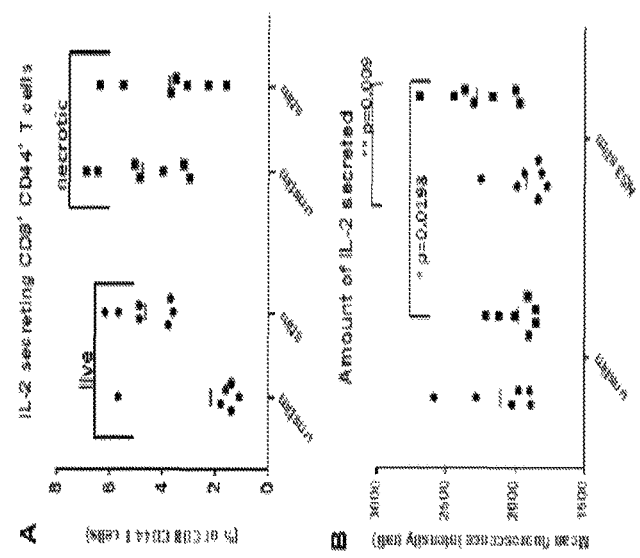
FIG. 36 shows the frequency of IL-2 secreting CD8+ CD44+ T cells (upper panel), and the mean fluorescent intensity of cells induced to express IL-2 (lower panel) after prime and boost according to Example 5, after stimulation or no stimulation in vitro with HCV NS3 peptides.
Figure 37:
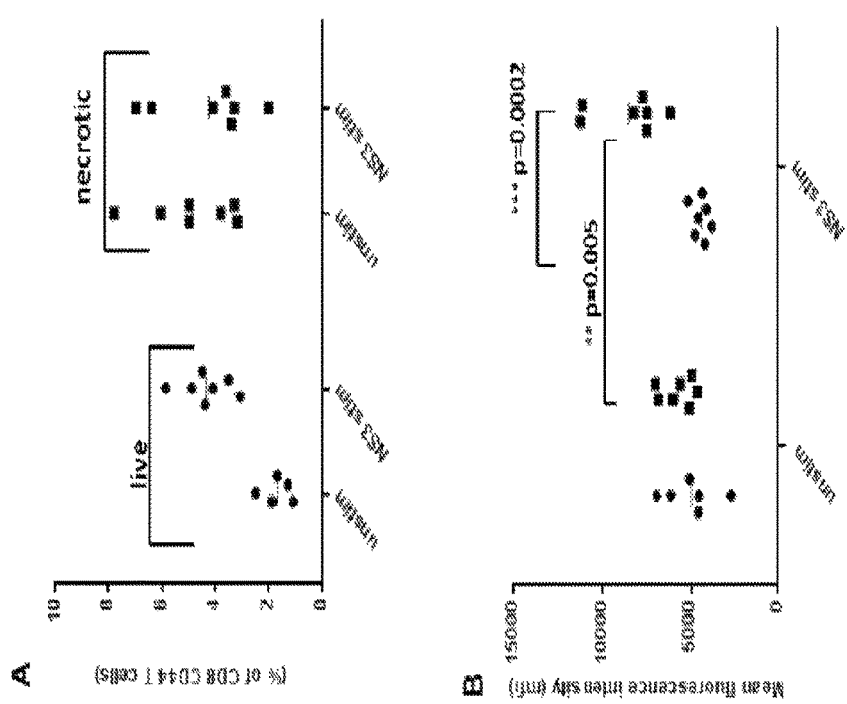
FIG. 37 shows the frequency of TNF secreting CD8+ CD44+ T cells (upper panel), and the mean fluorescent intensity of cells induced to express TNF (lower panel) after prime and boost according to Example 5, after stimulation or no stimulation in vitro with HCV NS3 peptides.
Figure 38:
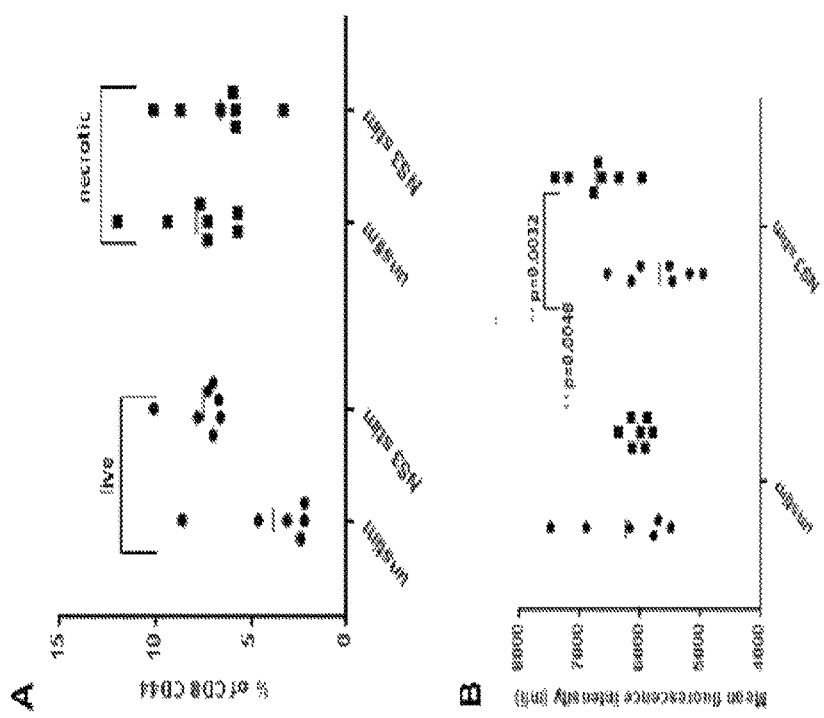
FIG. 38 shows the frequency of IFNg secreting CD8+ CD44+ T cells (upper panel) and the mean fluorescent intensity of cells induced to express IFNg (lower panel) after prime and boost according to Example 5, after stimulation or no stimulation in vitro with HCV NS3 peptides.

The amount of IL-2, TNF, and IFNg secreted by NS3 stimulated cells was significantly increased in mice vaccinated with the NS3 positive necrotic cells compared with the NS3 positive viable cells (FIGS. 36-38).

EXAMPLE 6

Materials and Methods

To examine the potential of vaccination with HCV antigen-positive, necrotic dendritic cells on the outcome of HCV infection, a number of HCV-positive human individuals who had previously failed conventional interferon-based therapy were vaccinated. Baseline blood samples were taken. Four weeks prior to vaccination with the HCV antigen-positive, necrotic dendritic cells, each patient was treated with interferon- for a total of 4 weeks. One week prior to the vaccination with the cells, a blood sample was taken from the patient and monocyte-derived dendritic cells (Mo-DC) were prepared from each patient essentially as we described previously (Gowans E J, Roberts S, Jones K, Dinatale I, Latour P A, Chua B, Eriksson E M Y, Chin R, Li S, Wall D M, Sparrow R L, Moloney J, Loudovaris M, Ffrench R, Prince H M, Hart D, Zeng W, Torresi J, Brown L E, Jackson D C (2010). *A phase I clinical trial of dendritic cell immunotherapy in HCV-infected individuals*. J Hepatology. 53(4): 599-607), a process that took 5 days. Essentially, peripheral blood specimens were collected in 9 ml lithium heparin vacutainer tubes (Becton Dickinson). For every 15 ml of blood an equal volume of RPMI (R-) (Invitrogen) was mixed by swirling into a 50 ml Falcon centrifuge tube. Ficoll-paque solution was then underlaid beneath the 30 ml of diluted blood using a syringe and cannula. Tubes were placed in a centrifuge with aerosol containment, and centrifuged at 400 g for 30 min at 22° C.

The cloudy mononuclear cell interface was aspirated using a syringe/cannula. The cells were then transferred into a separate fresh sterile 50 ml tube (Falcon) and made up to a volume of 45 ml using RPMI to wash cells. The cells were then centrifuged at 400 g for 8 min at room temperature. The supernatant was discarded and the cells from each tube were pooled into a 50 ml centrifuge tube and resuspended in in MACS buffer (PBS, 2 mM EDTA, 1% BSA) at a concentration of $2.5 \times 10^8$ cells/ml. CD14 Microbeads (Miltenyi Biotec) were then added to the cells at 20 µl per $1 \times 10^7$ cells. This mixture was incubated at 4° C. for 15 min and then washed with MACS buffer. The cells were then applied to an LS+ MACS column (Miltenyi) in a magnetic field supplied by a MACS magnet. CD14 negative cells were allowed to pass through the column to waste. The column was then removed from the magnet, and CD14 positive cells eluted from the column by applying 10 ml of MACS buffer using the plunger supplied in the kit. The CD14 positive monocytes were then washed with MACS buffer and resuspended in Aim-V media (Invitrogen) at concentration of $1 \times 10^6$ cells per ml, with 1000 U/ml of GM-CSF (Berlex) and IL-4 (R&D Systems). The cells were then incubated for 5 days at 37° C. to obtain immature monocyte derived DC (Mo-DC). The MO-DC were then infected with a recombinant human adenovirus which encodes the HCV proteins, E1, E2 and NS3, from a genotype 1b virus (Trowbridge and Gowans, 1998) and incubated at 37° C. for 48 hours to ensure HCV antigen expression. The cells were then incubated at 63° C. for 30 minutes to induce necrosis. For patients who received multiple doses of HCV antigen-positive Mo-DC, the live antigen positive cells were frozen in liquid nitrogen, thawed on the day of vaccination and then made necrotic as described above.

As this was a dose escalation trial, successive patients received increasing doses of necrotic cells, ranging from $1 \times 10^4$ to $1 \times 10^7$ cells, in phosphate buffered saline (PBS) on 1, 2 or 3 occasions by the intradermal route. Blood samples were taken at regular intervals after vaccination, and the HCV-specific cell mediated immune response measured by ELIspot analysis of PBMC stimulated ex vivo with peptide pools which collectively represented the complete HCV polyprotein or proteins contained in the vaccine. The viral load was also measured by quantitative RT-PCR. The design of the trial and details of the dose and dosing schedule are shown schematically in FIG. 39.

Results

Figure 40:
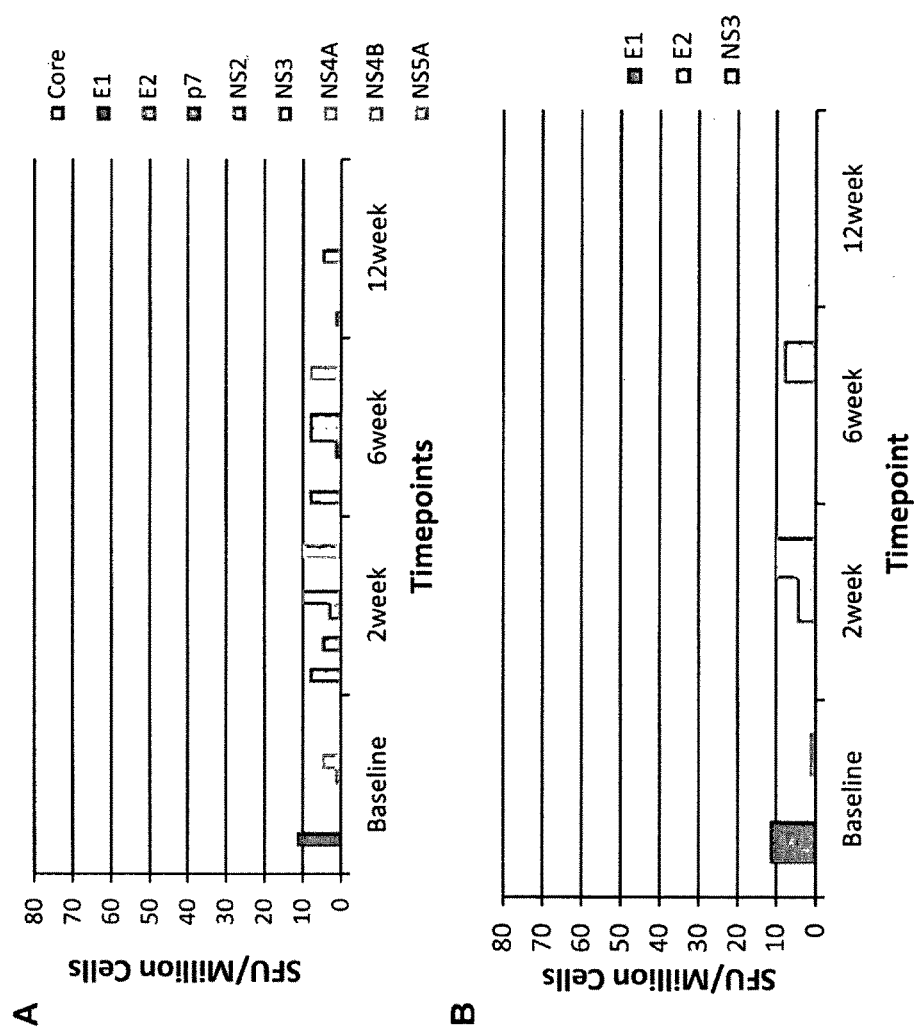
FIG. 40 shows graphs depicting the IFN-g ELISPOT response of patient 1 to (A) HCV peptide pools representing the complete HCV polyprotein and (B) peptides representing proteins in the vaccine according to Example 6.
Figure 41:
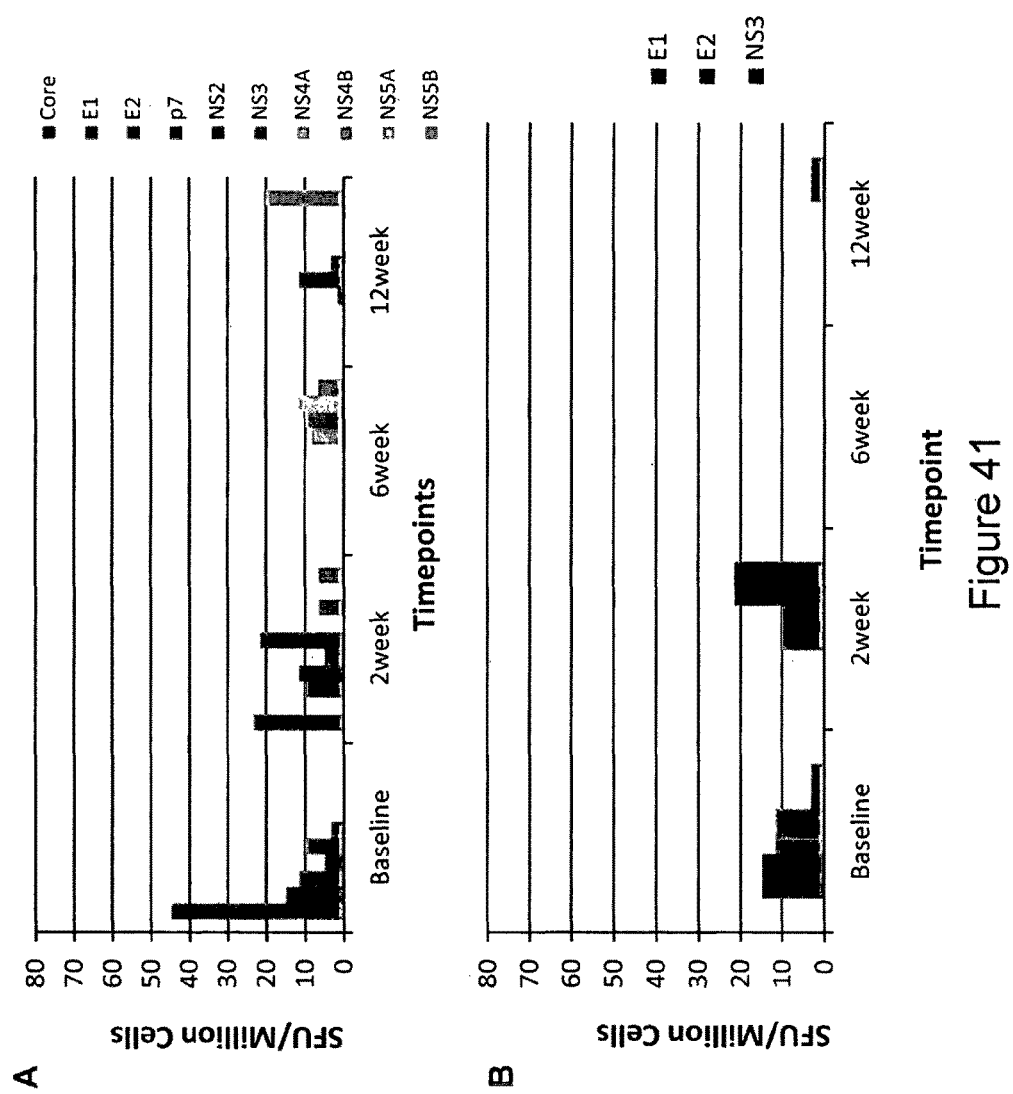
FIG. 41 shows graphs depicting the IFN-g ELISPOT response of patient 2 to (A) HCV peptide pools representing the complete HCV polyprotein and (B) peptides representing proteins in the vaccine according to Example 6.
Figure 42:
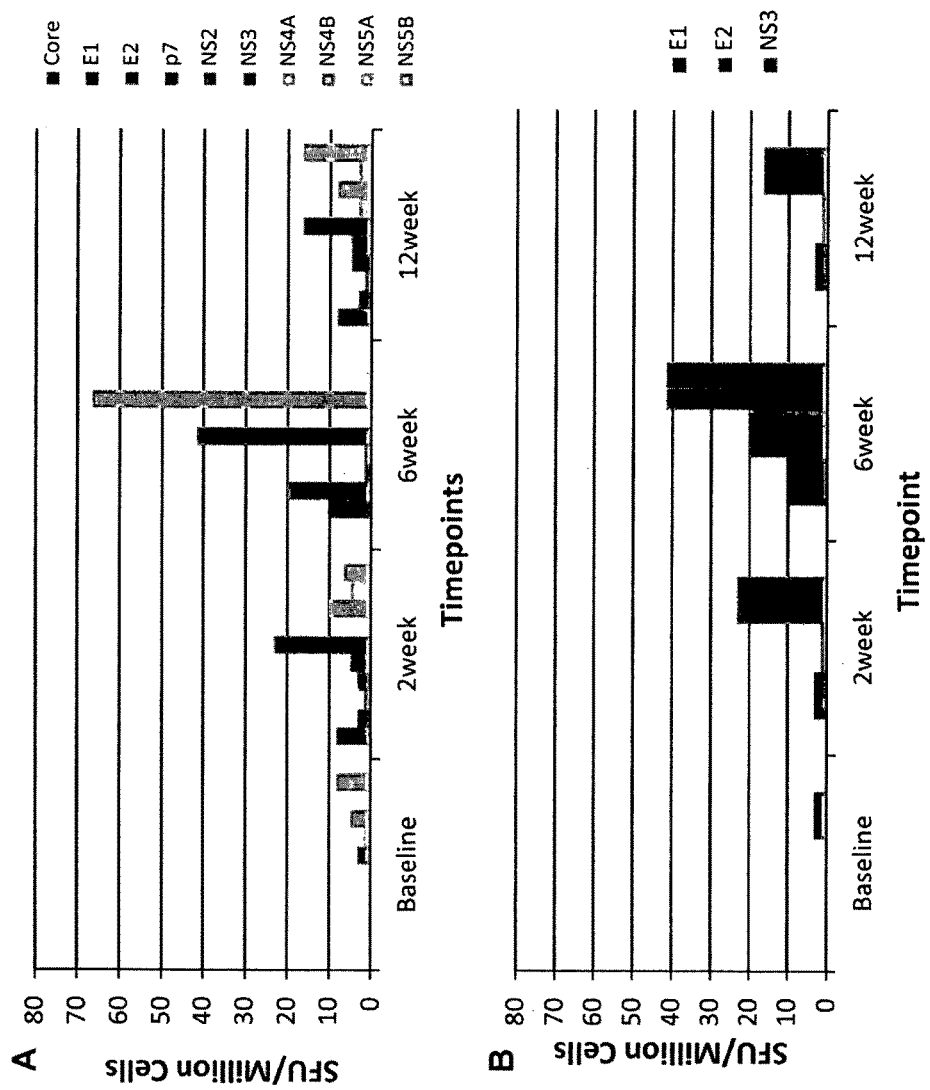
FIG. 42 shows graphs depicting the IFN-g ELISPOT response of patient 3 to (A) HCV peptide pools representing the complete HCV polyprotein and (B) peptides representing proteins in the vaccine according to Example 6.
Figure 43:
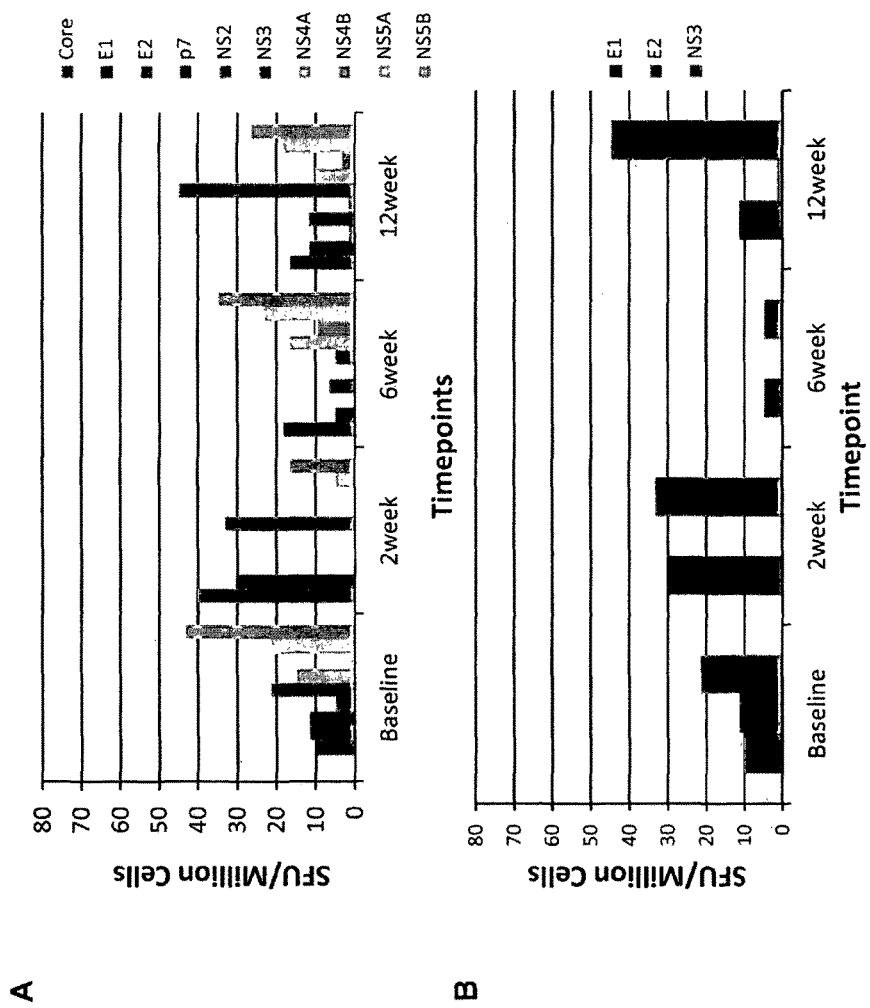
FIG. 43 shows graphs depicting the IFN-g ELISPOT response of patient 4 to (A) HCV peptide pools representing the complete HCV polyprotein and (B) peptides representing proteins in the vaccine according to Example 6.
Figure 44:
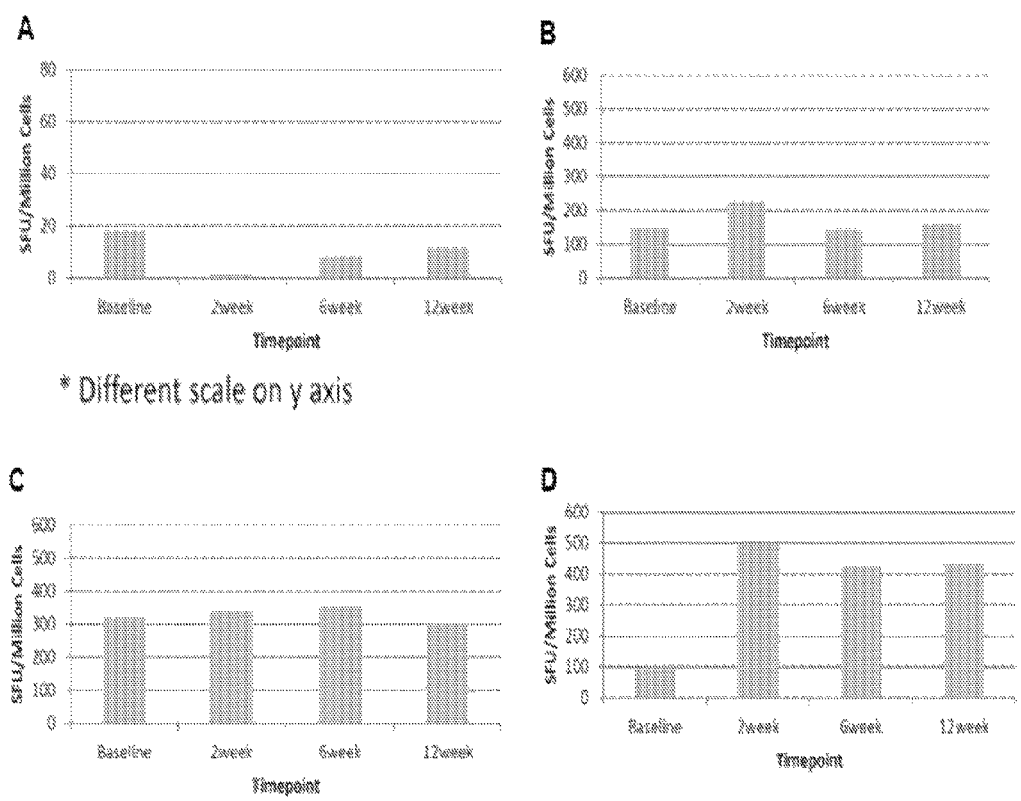
FIG. 44 shows graphs depicting the IFN-g ELISPOT response of patients 1 to 4 (A-D) to CEF peptide pools according to Example 6.
Figure 45:
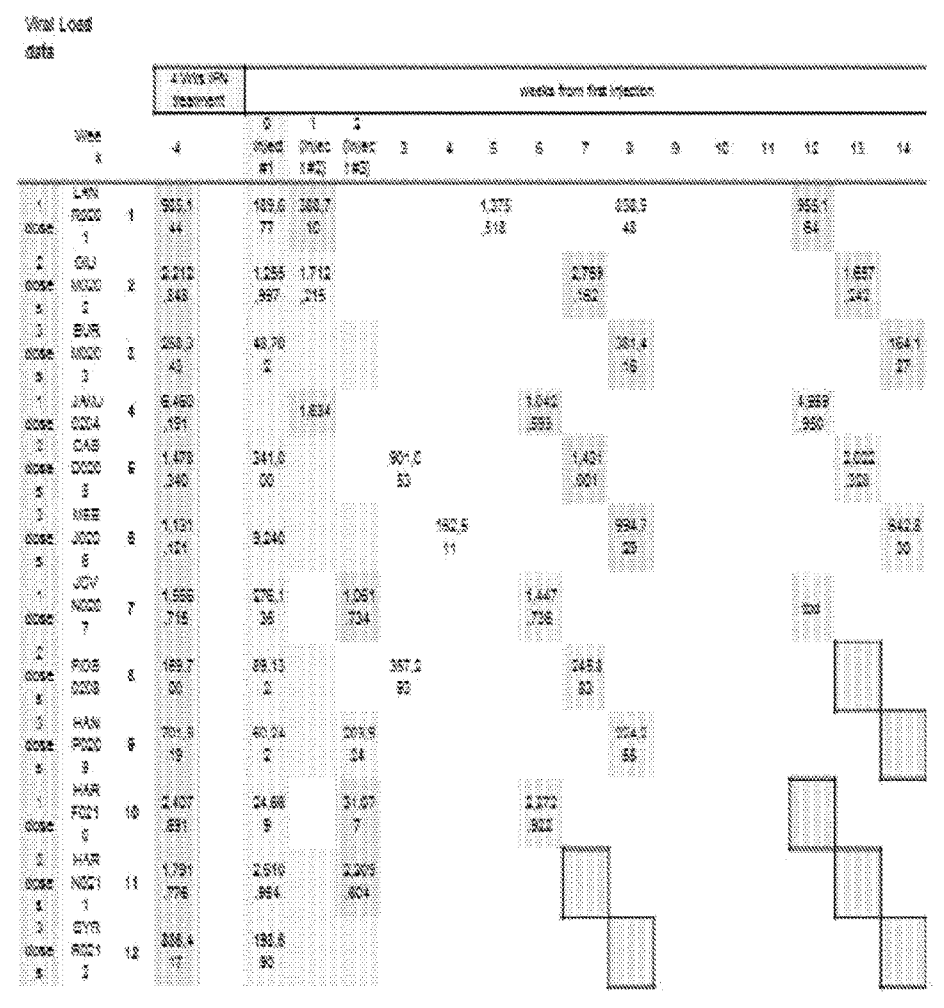
Figures 47, 48:
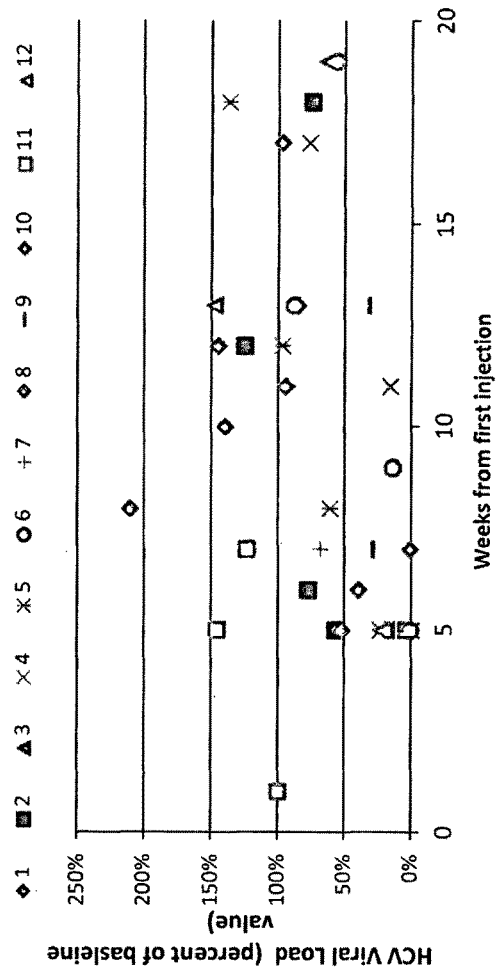
FIG. 47 shows a graph of the change in viral load in the patients vaccinated in the clinical trial according to Example 6.
FIG. 48 shows a table of the percentage viral load data for the patients vaccinated in the clinical trial according to Example 6.
Figure 49:
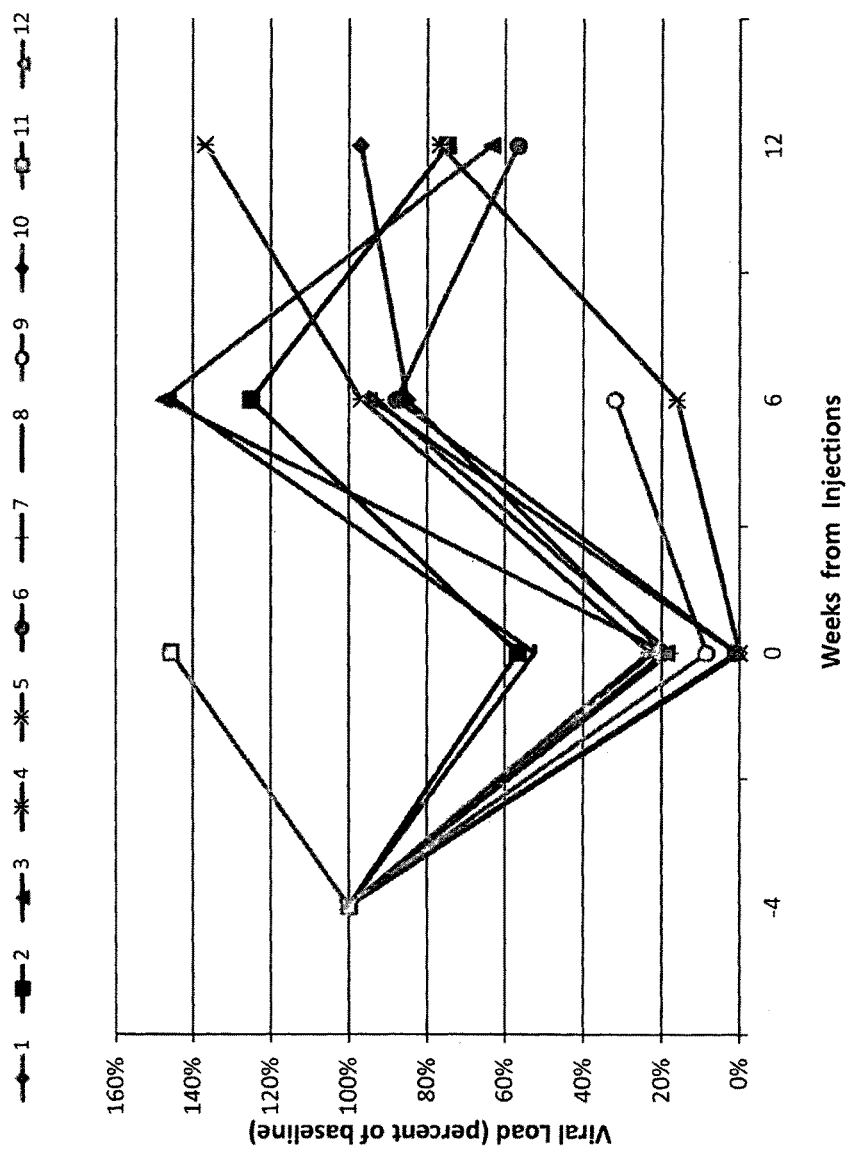
FIG. 49 shows a graph of the percentage change in viral load for the patients vaccinated in the clinical trial according to Example 6.

Although this Phase I trial was primarily designed to test safety, ELIspot and qRT-PCR were performed to examine any changes in the HCV cell mediated immunity and viral load as a measure of efficacy. None of the patients showed any adverse events. As patients #1 and #2 only received $1 \times 10^4$ and $2 \times 10^4$ cells respectively, these patient failed to show any increase in the HCV cell mediated immunity (FIGS. 40 and 41, upper and lower panels respectively) although there was a suggestion of a NS3-specific response in patient #2. Furthermore, although patients #3 and #4 showed some responses to a broad range of peptides, there was a clear increase in the HCV cell mediated immunity to peptides contained in the vaccine (FIGS. 42 and 43). As the clinical trial is still ongoing, no additional ELIspot data are available. To confirm that the ELIspot protocol was reproducible, ELIspot responses to the CEF peptides (peptides to CMV, EBV and influenza virus) showed minimal fluctuations, although there was a substantial increase in patient #4, from baseline to week 2 that may reflect a non-specific response to the vaccination (shown in FIG. 44). The viral load data were generated by the local pathology provider and are still not complete at this stage of the clinical trial. Most patients responded to the interferon induction and the raw data are shown in FIGS. 45 and 46 while the interpretation of the data are shown in various graphs (FIGS. 46-48). The data show that after vaccination, patients #6 and #3 showed viral loads that were 57% and 64% of baseline, while patients #2 and #4 showed viral loads of 75% and 77% of baseline. Patients #1 and #5 showed no responses to the vaccination, and indeed patient #5 showed a rebound greater than baseline (FIG. 49).

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The invention claimed is:

1. A method of inducing or enhancing an immune response against an immunogen in a subject, the method comprising:
   a) administering to the subject a first nucleic acid sequence encoding an immunogenic polypeptide linked to a first promoter and a second nucleic acid sequence encoding a cell death inducing polypeptide linked to a second promoter, wherein the cell death inducing polypeptide is perforin and wherein the first promoter has a greater relative efficacy than the second promoter, and
   b) expressing in a target cell in the subject the immunogenic polypeptide from the first nucleic acid sequence and the cell death inducing polypeptide from the second nucleic acid sequence, thereby inducing necrosis of the target cell and a pro-inflammatory immune response.

2. The method of claim 1, wherein the target cell is a somatic cell.

3. The method of claim 1, wherein the target cell is an antigen presenting cell.

4. The method of claim 1, wherein step b) further includes the step of presenting the expressed immunogenic polypeptide on the surface of the target cell.

5. The method of claim 1, wherein the immunogenic polypeptide is a viral peptide.

6. The method of claim 5, wherein the immunogenic polypeptide is a human immunodeficiency virus (HIV) or a hepatitis C virus (HCV) protein.

7. The method of claim 1, wherein the first promoter is a CMV promoter; and the second promoter is a SV40 promoter.

8. The method of claim 1, wherein the expression level of perforin is lower relative to the expression level of the immunogenic polypeptide.

9. The method of claim 8, wherein the expression level of perforin is at least 10-fold lower than the expression level of the immunogenic polypeptide.

10. The method of claim 3, wherein the step of administering the cell first and second nucleic acid sequence to the subject, thereby inducing a pro-inflammatory immune response, is carried out by processing of the immunogenic polypeptide by the antigen presenting cell via the class II pathway, such that the processed immunogenic polypeptide is detectable by nave $CD4^+$ T cells.

11. The method of claim 3, wherein the step of administering the first and second nucleic acid sequence to the subject, thereby inducing a pro-inflammatory immune response, is carried out by processing of the immunogenic polypeptide by the antigen presenting cell via the class I pathway, such that the processed immunogenic polypeptide is detectable by nave $CD8^+$ T cells.

* * * * *

UNITED STATES PATENT AND TRADEMARK OFFICE
CERTIFICATE OF CORRECTION

PATENT NO. : 10,052,377 B2
APPLICATION NO. : 15/397214
DATED : August 21, 2018
INVENTOR(S) : Eric James Gowans Page 1 of 1

It is certified that error appears in the above-identified patent and that said Letters Patent is hereby corrected as shown below:

In the Claims

Column 53, Line 19, "cell" should be deleted.

Signed and Sealed this
Twenty-fifth Day of September, 2018

Andrei Iancu
*Director of the United States Patent and Trademark Office*